(12) United States Patent
Reddy et al.

(10) Patent No.: US 9,060,990 B2
(45) Date of Patent: Jun. 23, 2015

(54) MAREK'S DISEASE VIRUS VACCINE COMPOSITIONS AND METHODS OF USING THEREOF

(75) Inventors: Sanjay Reddy, College Station, TX (US); Blanca Lupiani, College Station, TX (US)

(73) Assignee: The Texas A&M University System, College Station, TX (US)

( * ) Notice: Subject to any disclaimer, the term of this patent is extended or adjusted under 35 U.S.C. 154(b) by 831 days.

(21) Appl. No.: 12/502,822

(22) Filed: Jul. 14, 2009

(65) Prior Publication Data

US 2010/0233206 A1    Sep. 16, 2010

Related U.S. Application Data

(60) Provisional application No. 61/082,022, filed on Jul. 18, 2008.

(51) Int. Cl.
*A61K 39/255* (2006.01)
*C07K 14/005* (2006.01)
*C12N 7/00* (2006.01)
*A61K 39/00* (2006.01)

(52) U.S. Cl.
CPC ....... *A61K 39/255* (2013.01); *A61K 2039/5254* (2013.01); *C07K 14/005* (2013.01); *C12N 7/00* (2013.01); *C12N 2710/16321* (2013.01); *C12N 2710/16322* (2013.01); *C12N 2710/16334* (2013.01)

(58) Field of Classification Search
None
See application file for complete search history.

(56) References Cited

U.S. PATENT DOCUMENTS

| | | | |
|---|---|---|---|
| 3,642,574 A | 2/1972 | Okazaki et al. | |
| 4,160,024 A | 7/1979 | Schat et al. | |
| 4,895,717 A | 1/1990 | Witter | |
| 5,698,155 A | 12/1997 | Grosswald et al. | |
| 7,214,524 B1 * | 5/2007 | Reddy et al. | 435/235.1 |

OTHER PUBLICATIONS

Brown et al (PNAS 103:1687-1692, 2006).*
Spatz et al (Journal of General Virology 88:1080-1096, 2007).*
Qian et al (Journal of Virology 69:4037-4044, 1995).*
Jones et al (PNAS 89:4042-4046, 1992).*
Okada et al (Journal of General Virology 88:2111-2120, 2007).*
Liu et al (Virus Genes 21:51-64, 2000).*
Petherbridge et al (Journal of Virology 77:8712-8718, 2003).*
Benton, W. J., and Cover, M. S., Avian Diseases 1, 320-327 (1957).
Calnek, B. W., Pathogenesis of Marek's disease virus infection, Current Top Microbiology Immunology, 255, 25-55, (2001).
de Boer et al., Avian Diseases 30, 276-283, (1986).
de Boer et al., Advances in Marek's Disease Research, pp. 405-413, (1988).
Lee et al., Recombinant Maerk's disearse virus (MDV) lacking the Meq oncogene confers protection against challenge with a very virulent plus strin of MDV, Vaccine 26, 1887-1892, (2008).
Lupiani et al., Proceedings of the National Academy of Sciences USA 101, 11815-11820, (2004).
Marek, J., Multiple Nervenentztindüng (Polyneuritis) bei Hühnern, Dtsch. Tierärztl. Wochenschr 15, 417-421, (1907)*.
Nielsen et al., Anticancer Drug Design 8, 53-63, (1993).
Reddy S. M., Lupiani, B., Gimeno, I. M., Silva, R. F., Lee, L. F., and Witter, R. L. Rescue of a pathogenic Marek's disease virus with overlapping cosmid DNAs: use of a pp38 mutant to validate the technology for the study of gene function, Proceedings of the National Academy of Sciences U S A 99, 7054-7059, (2002).
Rispens et al., Control of Marek's disease in the Netherlands. I. Isolation of an avirulent Marek's disease virus (strain CVI 988) and its use in laboratory vaccination trials, Avian Diseases 16, 108-125, (1972).
Rispens, B. H., van Vloten, H., Mastenbroek, N., Maas, J. L., and Schat, K. A., Control of Marek's disease in the Netherlands. II. Field trials on vaccination with an avirulent strain (CVI 988) of Marek's disease virus, Avian Diseases 16, 126-138, (1972).
Schat et al., Journal National Cancer Institute 60, 1075-1082 (1978).
Schat et al., Avian Pathology 11, 593-606 (1982).
Spatz et al., Polymorphisms in the repeat long regions of oncogenic and attenuated pathotypes of Marek's disease virus 1, Virus Genes, 35:41-53, (2007).
Tulman, E. R., Afonso, C. L., Lu, Z., Zsak, L., Rock, D. L., and Kutish, G. F., The genome of a very virulent Marek's disease virus, Journal Virology 74, 7980-7988, (2000).
Witter et al., American Journal Veterinarian Research 31, 525-538, (1970).
Witter, Avian Pathology 11, 49-62, (1982).
Witter et al., Avian Pathology 13, 75-92, (1984).
Witter, Avian Diseases 31, 752-765, (1987).
Witter et al., Avian Diseases 35, 877-891, (1991).
Witter et al., The Fourth International Symposium on Marek's Disease, pp. 315-319, (1992).
Witter, R. L., Protective efficacy of Marek's disease vaccines, Current Top Microbiology Immunology 255, 57-90, (2001).
Witter et al., Serotype 1 Viruses Modified by Backpassage or Insertional Mutagenesis: Approaching the Threshold of Vaccine Efficacy in Marek's Disease, Avian Diseases, 48(4);768-782, (2004).

* cited by examiner

*Primary Examiner* — Mary E Mosher
(74) *Attorney, Agent, or Firm* — Medlen & Carroll, LLP

(57) ABSTRACT

Marek's disease virus (MDV), the etiologic agent of Marek's disease, is a potent oncogenic herpesvirus. MDV is highly contagious and elicits a rapid on

FIGURE 6

| Group | 15x7 (Ab -) | 15x7 (Ab +) |
|---|---|---|
| Control | 0/10 | 0/10 |
| CVI988 | 0/10 | 0/10 |
| rMd5 | 17/17 | 17/17 |
| rMd5-CVI-LMeq | 2/17 | 0/17 |
| rMd5-CVI-Meq | 2/17 | 0/17 |

FIGURE 7

| Group | MDV maternal antibody + | |
|---|---|---|
| | Replicate 1 | Replicate 2 |
| Control | 10/10 | 10/10 |
| CVI988 | 5/17 | 7/17 |
| rMd5-CVI-LMeq | 0/17 | 0/17 |
| rMd5-CVI-Meq | 0/17 | 0/17 |

FIGURE 8

| Region | rMd5 | Published Md5 |
|---|---|---|
| a-like sequences | 1-1142 | 1-1281 |
| TLR | 1143-13893 | 1282-14028 |
| UL | 13894-127438 | 14029-127591 |
| IRL | 127439-140181 | 127592-140338 |
| a-like sequences | 140182-141564 | 140339-141526 |
| IRS | 141565-153836 | 141527-153798 |
| US | 153837-164683 | 153799-164645 |
| TRS | 164684-176955 | 164646-176918 |
| a-like sequences | 176956-178316 | 176919-177874 |

FIGURE 9

| Pathogenesis and protection studies of rMd5/CVI-Meq, rMd5/CVI-LMeq and their cell culture (duck or chicken embryo fibroblasts) adapted derivatives in chickens. | | | | |
|---|---|---|---|---|
| Group | Cells used for adaptation | MD[1] | | PI[2] |
| | | Pathogenesis SPF (Ab-)[3] | Protection Hyline (Ab+)[4] | |
| rMd5/CVI-LMeq P0 | | 7 (54)[5] | 2 (13) | 87 |
| rMd5/CVI-LMeq P20D | DEF | 7 (58) | 3 (20) | 80 |
| rMd5/CVI-LMeq P30D | | 4 (31) | 0 (0) | 100 |
| rMd5/CVI-LMeq P20C | CEF | 5 (42) | 1 (7) | 93 |
| rMd5/CVI-LMeq P30C | | 2 (17) | 1 (7) | 93 |
| rMd5/CVI-Meq P0 | | 4 (31) | 1 (7) | 93 |
| rMd5/CVI-Meq P20D | DEF | 0 (0) | 0 (0) | 100 |
| rMd5/CVI-Meq P30D | | 0 (0) | 2 (13) | 87 |
| rMd5/CVI-Meq P20C | CEF | 2 (17) | 4 (26) | 74 |
| rMd5/CVI-Meq P30C | | 0 (0) | 2 (13) | 87 |
| CVI988 | | ND[4] | 2 (13) | 87 |
| Neg Control (no virus) | | 0 (0) | 0 (0) | NA[7] |
| Pos Control (no vaccine/challenged) | | ND | 15 (100) | NA |

[1] MD: Marek's disease gross lesions
[2] PI: Protection index
[3] MDV maternal antibody negative specific pathogen free chickens infected at day of age
[4] Commercial male MDV maternal antibody positive chickens from Hyline International vaccinated at day of age and challenged at day six of age with 648A, a very virulent plus strain of MDV
[5] Number of birds with MD (%)
[6] ND: Not determined
[7] NA: Not applicable

FIGURE 12

FIGURE 14
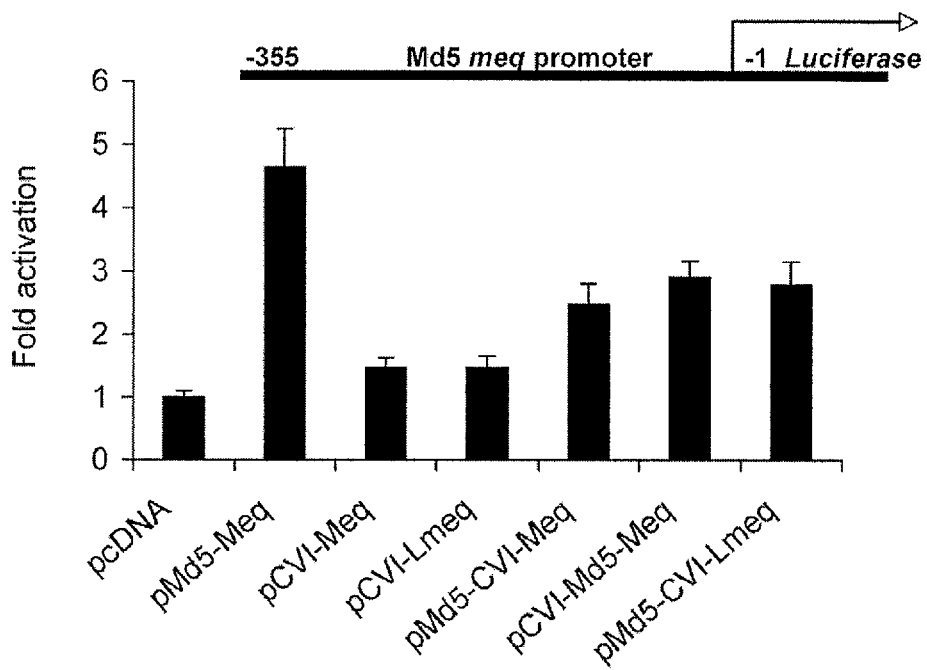
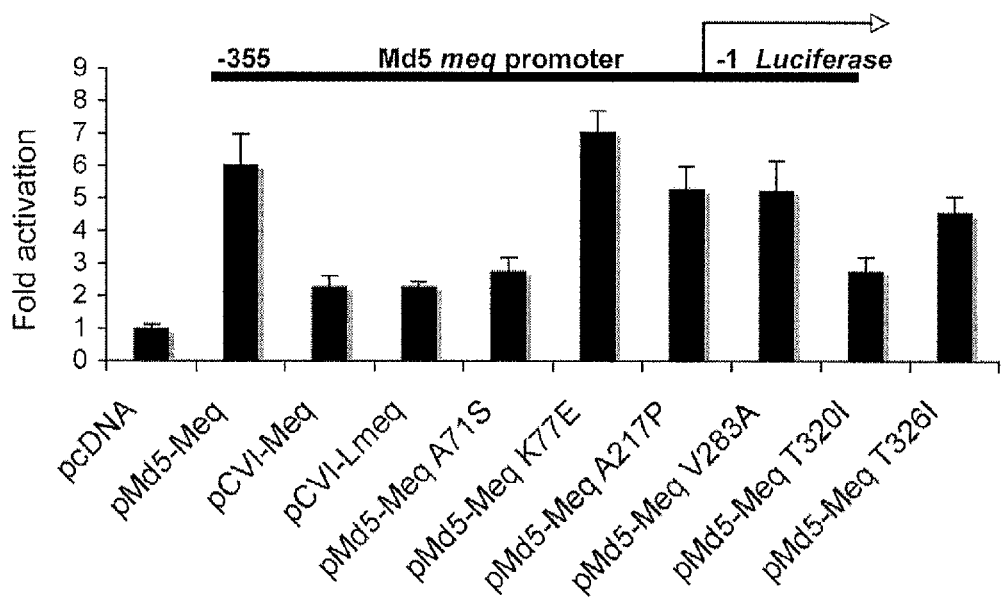

Experimental groups:

| Control |
| CVI988/Rispens |
| rMd5 |
| rMd5- CVI Meq |
| rMd5- CVI-L Meq |

Day 1
Virus Inoculation
➡
Day 6
Spleen, bursa thymus collected for IHC
➡
Day 38
Blood collected for reactivation assay
➡
Day 56
Termination
Blood collected from contacts

| Group | Maternal MDV Antibodies | |
|---|---|---|
| | Negative | Positive |
| Control | 0/8 | 0/10 |
| CVI98/Rispens | 0/8 | 0/10 |
| rMd5 | 15/15 | 17/17 |
| rMd5-CVI Meq | 1/15 | 0/17 |
| rMd5-CVI-L Meq | 3/15 | 0/17 |

FIG 21A

Meq-Fos (MF) protein sequence encoded by rMd5-MF (SEQ ID NO: 7)

MSQEPEPGAMPYSPADDPSPLDLSLGSTSRRKKKRKSHDIPNSPSKHPFPDGLSEEE
KQKLERRRKRNRDAARRRRRKQTDYVDKLQAETDQLEEEKSALQAEIANLLKE
KEKLRVQLACHEPVCPMAVPLTVTLGLLTTPHDPVPEPPICTPPPPSPDEPNAPHC
SGSQPPICTPPPPDTEELCAQLCSTPPPPISTPHIIYAPGPSPLQPPICTPAPPDAEELC
AQLCSTPPPPICTPHSLFCPPQPPSPEGIFPALCPVTEPCTPPSPGTVYAQLCPVGQV
PLFTPSPPHPAPEPERLYARLTEDPEQDSLYSGQIYTQFPSDTQSTVWWFPGDGRP

FIG 21B

CVI Meq protein sequence encoded by rMd5-CVI Meq (SEQ ID NO: 8)

MSQEPEPGAMPYSPADDPSPLDLSLGSTSRRKKKRKSHDIPNSPSKHPFPDGLSEEE
KQKLERRRKRNRDASRRRRREQTDYVDKLHEACEELQRANEHLRKEIRDLRTEC
TSLRVQLACHEPVCPMAVPLTVTLGLLTTPHDPVPEPPICTPPPPSPDEPNAPHCS
GSQPPICTPPPPDTEELCAQLCSTPPPISTPHIIYAPGPSPLQPPICTPPPPDAEELCAQ
LCSTPPPPICTPHSLFCPPQPPSPEGIFPALCPVTEPCTPPSPGTVYAQLCPVGQAPL
FTPSPPHPAPEPERLYARLTEDPEQDSLYSGQIYIQFPSDIQSTVWWFPGDGRP

FIG 21C

CVI-L Meq protein sequence encoded by rMd5-CVI-L Meq (SEQ ID NO: 9)

MSQEPEPGAMPYSPADDPSPLDLSLGSTSRRKKKRKSHDIPNSPSKHPFPDGLSEEE
KQKLERRRKRNRDASRRRRREQTDYVDKLHEACEELQRANEHLRKEIRDLRTEC
TSLRVQLACHEPVCPMAVPLTVTLGLLTTPHDPVPEPPICTPPPPSPDEPNAPHCS
GSQPPICTPPPPDTEELCAQLCSTPPPISTPHIIYAPGPSPLQPPICTPPPPDAEELCAQ
LCSTPPPPISTPHIFYAPGLCSTPPPPISTPHIIYAPGPSPLQPPICTPPPPDAEELCAQL
CSTPPPPICTPHSLFCPPQPPSPEGIFPALCPVTEPCTPPSPGTVYAQLCPVGQAPLF
TPSPPHPAPEPERLYARLTEDPEQDSLYSGQIYIQFPSDIQSTVWWFPGDGRP

FIG 21D

Md5/CVI Meq protein sequence encoded by rMd5 Md5/CVI Meq (SEQ ID NO: 10)

MSQEPEPGAMPYSPADDPSPLDLSLGSTSRRKKKRKSHDIPNSPSKHPFPDGLSEEE
KQKLERRRKRNRDAARRRRRKQTDYVDKLHEACEELQRANEHLRKEIRDLRTE
CTSLRVQLACHEPVCPMAVPLTVTLGLLTTPHDPVPEPPICTPPPPSPDEPNAPHCS
GSQPPICTPPPPDTEELCAQLCSTPPPPISTPHIIYAPGPSPLQPPICTPPPPDAEELCA
QLCSTPPPPICTPHSLFCPPQPPSPEGIFPALCPVTEPCTPPSPGTVYAQLCPVGQAP
LFTPSPPHPAPEPERLYARLTEDPEQDSLYSGQIYIQFPSDIQSTVWWFPGDGRP

FIG 21E

CVI/Md5 Meq protein sequence encoded by rMd5 CVI/Md5 Meq (SEQ ID NO: 11)

MSQEPEPGAMPYSPADDPSPLDLSLGSTSRRKKKRKSHDIPNSPSKHPFPDGLSEEE
KQKLERRRKRNRDASRRRRREQTDYVDKLHEACEELQRANEHLRKEIRDLRTEC
TSLRVQLACHEPVCPMAVPLTVTLGLLTTPHDPVPEPPICTPPPPSPDEPNAPHCS
GSQPPICTPPPPDTEELCAQLCSTPPPPISTPHIIYAPGPSPLQPPICTPAPPDAEELCA
QLCSTPPPPICTPHSLFCPPQPPSPEGIFPALCPVTEPCTPPSPGTVYAQLCPVGQVP
LFTPSPPHPAPEPERLYARLTEDPEQDSLYSGQIYTQFPSDTQSTVWWFPGDGRP

FIG 22A

Md5 T28A protein sequence encoded by rMd5 T28A Meq (SEQ ID NO: 12)

MSQEPEPGAMPYSPADDPSPLDLSLGS<u>A</u>SRRKKRKSHDIPNSPSKHPFPDGLSEEE
KQKLERRRKRNRDAARRRRRKQTDYVDKLHEACEELQRANEHLRKEIRDLRTE
CTSLRVQLACHEPVCPMAVPLTVTLGLLTTPHDPVPEPPICTPPPPSPDEPNAPHCS
GSQPPICTPPPPDTEELCAQLCSTPPPPISTPHIIYAPGPSPLQPPICTPAPPDAEELCA
QLCSTPPPPICTPHSLFCPPQPPSPEGIFPALCPVTEPCTPPSPGTVYAQLCPVGQVP
LFTPSPPHPAPEPERLYARLTEDPEQDSLYSGQIYTQFPSDTQSTVWWFPGDGRP

FIG 22B

Md5 S42A protein sequence encoded by rMd5 S42A Meq (SEQ ID NO: 13)

MSQEPEPGAMPYSPADDPSPLDLSLGSTSRRKKRKSHDIPN<u>A</u>PSKHPFPDGLSEEE
KQKLERRRKRNRDAARRRRRKQTDYVDKLHEACEELQRANEHLRKEIRDLRTE
CTSLRVQLACHEPVCPMAVPLTVTLGLLTTPHDPVPEPPICTPPPPSPDEPNAPHCS
GSQPPICTPPPPDTEELCAQLCSTPPPPISTPHIIYAPGPSPLQPPICTPAPPDAEELCA
QLCSTPPPPICTPHSLFCPPQPPSPEGIFPALCPVTEPCTPPSPGTVYAQLCPVGQVP
LFTPSPPHPAPEPERLYARLTEDPEQDSLYSGQIYTQFPSDTQSTVWWFPGDGRP

FIG 22C

Md5 S42D protein sequence encoded by rMd5 S42D Meq (SEQ ID NO: 14)

MSQEPEPGAMPYSPADDPSPLDLSLGSTSRRKKRKSHDIPN<u>D</u>PSKHPFPDGLSEEE
KQKLERRRKRNRDAARRRRRKQTDYVDKLHEACEELQRANEHLRKEIRDLRTE
CTSLRVQLACHEPVCPMAVPLTVTLGLLTTPHDPVPEPPICTPPPPSPDEPNAPHCS
GSQPPICTPPPPDTEELCAQLCSTPPPPISTPHIIYAPGPSPLQPPICTPAPPDAEELCA
QLCSTPPPPICTPHSLFCPPQPPSPEGIFPALCPVTEPCTPPSPGTVYAQLCPVGQVP
LFTPSPPHPAPEPERLYARLTEDPEQDSLYSGQIYTQFPSDTQSTVWWFPGDGRP

FIG 22D

Meq A71S protein sequence encoded by rMd5 A71S Meq (SEQ ID NO: 15)

MSQEPEPGAMPYSPADDPSPLDLSLGSTSRRKKRKSHDIPNSPSKHPFPDGLSEEE
KQKLERRRKRNRDA<u>S</u>RRRRRKQTDYVDKLHEACEELQRANEHLRKEIRDLRTE
CTSLRVQLACHEPVCPMAVPLTVTLGLLTTPHDPVPEPPICTPPPPSPDEPNAPHCS
GSQPPICTPPPPDTEELCAQLCSTPPPPISTPHIIYAPGPSPLQPPICTPAPPDAEELCA
QLCSTPPPPICTPHSLFCPPQPPSPEGIFPALCPVTEPCTPPSPGTVYAQLCPVGQVP
LFTPSPPHPAPEPERLYARLTEDPEQDSLYSGQIYTQFPSDTQSTVWWFPGDGRP

FIG 22E

Meq A71D protein sequence encoded by rMd5 A71D Meq (SEQ ID NO: 16)

MSQEPEPGAMPYSPADDPSPLDLSLGSTSRRKKRKSHDIPNSPSKHPFPDGLSEEE
KQKLERRRKRNRDA<u>D</u>RRRRRKQTDYVDKLHEACEELQRANEHLRKEIRDLRTE
CTSLRVQLACHEPVCPMAVPLTVTLGLLTTPHDPVPEPPICTPPPPSPDEPNAPHCS
GSQPPICTPPPPDTEELCAQLCSTPPPPISTPHIIYAPGPSPLQPPICTPAPPDAEELCA
QLCSTPPPPICTPHSLFCPPQPPSPEGIFPALCPVTEPCTPPSPGTVYAQLCPVGQVP
LFTPSPPHPAPEPERLYARLTEDPEQDSLYSGQIYTQFPSDTQSTVWWFPGDGRP

FIG 22F

Meq A71E-R72P protein sequence encoded by rMd5 A71E-R72P Meq (SEQ ID NO: 17)

MSQEPEPGAMPYSPADDPSPLDLSLGSTSRRKKRKSHDIPNSPSKHPFPDGLSEEE
KQKLERRRKRNRDA<u>EP</u>RRRRKQTDYVDKLHEACEELQRANEHLRKEIRDLRTE
CTSLRVQLACHEPVCPMAVPLTVTLGLLTTPHDPVPEPPICTPPPPSPDEPNAPHCS
GSQPPICTPPPPDTEELCAQLCSTPPPPISTPHIIYAPGPSPLQPPICTPAPPDAEELCA
QLCSTPPPPICTPHSLFCPPQPPSPEGIFPALCPVTEPCTPPSPGTVYAQLCPVGQVP
LFTPSPPHPAPEPERLYARLTEDPEQDSLYSGQIYTQFPSDTQSTVWWFPGDGRP

FIG 22G

Meq T79A protein sequence encoded by rMd5 T79A Meq (SEQ ID NO: 18)

MSQEPEPGAMPYSPADDPSPLDLSLGSTSRRKKRKSHDIPNSPSKHPFPDGLSEEE
KQKLERRRKRNRDAARRRRRKQADYVDKLHEACEELQRANEHLRKEIRDLRTE
CTSLRVQLACHEPVCPMAVPLTVTLGLLTTPHDPVPEPPICTPPPPSPDEPNAPHCS
GSQPPICTPPPPDTEELCAQLCSTPPPPISTPHIIYAPGPSPLQPPICTPAPPDAEELCA
QLCSTPPPPICTPHSLFCPPQPPSPEGIFPALCPVTEPCTPPSPGTVYAQLCPVGQVP
LFTPSPPHPAPEPERLYARLTEDPEQDSLYSGQIYTQFPSDTQSTVWWFPGDGRP

FIG 23

BamHI sequence, with deletion of the vIL8 gene from ClaI-NcoI (2807-3606) (SEQ ID NO: 19):

GATCCGATCCCGCAGACCCCGGCCCACAGGAAGGGGCGGGGCACGTGCATG
GGGCGTGGCGGGAGATGAATGACCGCGGAGTTCCAAACTCCCGCACCGGCCC
CTCTCTGCTCGCTCTCCTCCCCGCCGCCAATAGCTACGCGGCAGCGTACAGCC
CGGCCAATAGGCGCGCGGTGGGCGTAGGCGGAGGAAGCTACAAGAGCCCCA
CGCGGGGTTCCCCCGGCACACGTGGCGGGTGGAAGGCTCCGCTGTGTCTAAC
CCTAATCGGAGGTATTGATGGTACTGTCGCCGCGCTCCCTCCGCCCGCTGTTT
ACTCGCTGACTTTCAGCGGGCTAGGGGAGCCGCCCCAGGGGGCGCCGCGGCG
GGGAGGGGGTGGGGCGGACGCGGGAGAAAGGACCGAAAGGGGCTCCACGG
CAAACAAAAAAAAACGTCAGCGAGGGGTCCTCTCGCCCCATCCGCCCTGGG
GTCCTCGCCCGCAGGCCGCGGTCGGCCGGCACCCGCCATTGCCGCCGCGAAG
AGTTCGCCTCTGTCAGCCTCGGCGGCGCCCGGGAGATGCGGCGCGCGGCCCC
GCGCCCCAGCAGAGCAACACGGGAGCGGCGCCCCGGGGCAACCCCCGCG
CCCCCCTGCGCCGTGGGGCGCGCGGACGGCGTCGCTCCCACACGCGCGGCCC
CGCGCGCACGACCGTTGGAGCCGTTGAGCCGCGCGCGGGGCTCTGTGAGTAG
ACCGAACGGGCCCCCGCGGAGGTGGGCGCTCGAGCCCGGTCCCTGCGCAGG
TGGTGCCCGCTGGGCGCCGCTCGGGGCTACCGGGGTCCGTCCGCGGCCGTGC
CGGGCGCCCAGGCGCCGAGTCCTGGCCTGGACGTGTGGCGGTGCGCAGCGCG
GAGCCCTGTCCCGGCAGGAGCCGTCCTCTGCCTCGGCACGCTCCGCAATAAG
CGTGGGCAAACGTGTGGGCCGTGCAGGGCATGAGCGTGCACAAAGACGTGG
CCCTGGGGCTTGGGCTGAGCGCAGTGCGATGCCCCGGGTCATCACCCGTCC
CGCAGATCCCCGTGCACGGGGTCAGTGCCATCTTGTGGTCTCGGCTTTCTTTT
TTCCCCCTTTTGCACGAAGAGTCAGTGAACTTGGGGTACTTAATCGTGCTTTA
ATTGCGCGATGGAGAACCGTTGCTAGAATATGTGGGGATAGAGAAGTCCGAT
ACCCTCAGAAATGTGCGAGTCCTGCGGGTAGAATCGGCGCAGCACTGAATAA
ACCCGCGGGGCCCTAAAACCTCTCGCGGCCGACAGACAGTTGTACACCTGCC
TGCATTACTACATCCAGTTCGTAGACCGTATCCCTGCTCCATCCAATAGCTAC

FIG 23 CONT

ATTATCGCATGGAACCGTACCCGTAATGCCTCGGGCGATTTCCCTGTTATTGG
GTCTCCACCAACACGTGATATTGGAGACCCCCAACTTAAAATTCCACGACCG
TGAGATGCATTTTGTTTATTGAAAATTTCCATTCGATGGGGCATAAACTATAG
CATCGAAACACTAAAATGAACAGGAGTTTGCATCAAAAGGTGATAATACTGG
AACACAAGACTATGAGGACCCTTAAATGTATATGAGAAAATTCCCACGACCC
CTGCATAGCAGAAAACCAGGACCACAATAAATTTTGCAGTACGCATGCGCCC
TCTACACACGACCCGCATGCGCTGACCACTTACTGCAGTACGCATGCGCCCTC
TACACACAAAACGCATGCGCAGTCCAAAACGCATGCGCAGACCGCTTACGGC
AGTACGCATGCGCCCTCTACACACAAAACGCATGCGCAGACCAATTACCCAA
AACAAGCATGCGCCGTAAGTATGGTTATCTGCGCATGCCTGGTTTTCGACACA
CGCGCATGCGCAGATACACTCCACCGTACGCATGCGCGTCATGCATAACTGG
CGCATGCGTGAACGCCTTACCCGAACCAGCCCTGCGCGCTTGCGCTATATAC
GCCCTGCGCACTCATCGCGCATGCGCACAGACGTTCAAATAATGGCGGACAT
TTCCGTCAACAAACGCACTAAGGTAAAAAAAAAAACCACGAACCGTTAGTTT
TTAGGAGCTACGATTTAATTTTCATGCTCTGCTTTATCAAGACTCGAAATGCG
TTACAGCTTCCCCCCGTACCGGCACCGACAGTTCTTTACGTAAGCCCTTCCCG
TTCACTCTTTCACGCGCGGCACTATCGGTACAACAGTGGCACACATCAAACA
AAGTAAAAGGGGAAGGGAATTGAATTTCTACAAAAGATCTAAATTTTACGTA
ATGGATC

FIG 24

MDV sequences (896-5084) with deletion of the BamHI region (1451-4544), that results in the deletion of vTR and vIL8 genes (SEQ ID NO: 20):

TGAACCCTAACCCTAACCCTAACCCTAACCCTAACCCTAACCCTAACCCTAAC
CCTAACCCTAACCCCCCAAATTTTCACCCCCCCTCACCCCCATCCAAAATAAG
CCAAATATAATGTAGAGGATGGGAGAATCCGGGGGCGATAAGACACTTTCCC
ACTCATACTGAAGATGTCTTAACCGTGAACCTAGTCTCGATCCCGAGCTCAAA
GCACGGAAATCCACACTGGAACCGGCACATACCACCTGTGATGTGACGCAAA
CTTGGATTATGCAAGTGGTGACTCCGTGGTGTGAAATTAGACCCCCCCTGTTT
CTCGACCCCCCACCCTAACCCTAACCCTAACCCTAACCCTAACCCTAACCCCC
AAAAACCTCTCGCGGCCGACAGGCAGTTGTACACCTGCCTGCACTACTACAT
CCGGTCCGTAGACCACATCCCTGCTCCATCCAATAACTCGAACGCTCTTCCTA
TAGGTAGATACAGGACATGTTTTAACGAGGTTCTGCGCTAAATCCAGGGCGG
GAAAGCTCAGCCCGCATCTCGCAGCCCCCGGATCCCGTCCCGATCGTCCCCTC
ACACGTGGCACTGCCGCGTAAACAATGCCACATCGTAGAGAAAGCATAAGG
GGGAGGCCATCGGGAGATTATCCCGAGAATTCAAACTATTCTTGTAATGTCG
TACGAGCCTCGTTCCGTTCGCTCTTTCATGCGCAGCATTACCGGTGTAAATGT
AATAATGCCGCACAGTGAACAAGCAAAAGGGGAAGAGAGTCTCCGGATAGC
CGTTACAATCCAGTAACGACTTAACGCAGATTACTCCTGCATAAGCGTCTCTG
CGATGAGGTATTTTCCATATGTTCCTGGAGGTCCGTGCCTGTATATTCGTTAA
TGTCGACATCTGCCTATGTGCCTGTGTATCGGTGCATAGGAGTATGTCTGTGC
ATCCCTGTATATATTATCTGTGCATATTTGCATAATTCATAAACGAATATTTA
ATTACAGTAGTGTTGCGCGAGCCCCGATCCATTGATCTGCTCACGACTGTAGC
ACTTAGAATCGCACAGTGCACAGCCAGTGAGCTGGCCACAGGAGAG

FIG 25

EcoQ fragment from the CVI988 strain coding for the long form of Meq gene (SEQ ID NO: 21):

AATTCAAACTATTCTTGTAATGTCGTACGAGCCTCGTTCCGTTCGCTCTTTCAT
GCGCAGCATTACCGGTGTAAATGTAATAATGCCGCACAGTGAACAAGCAAAA
GGGGAAGAGAGTCTCCGGATAGCCGTTACAATCCAGTAACGACTTAACGCAG
ATTACTCCTGCATAAGCGTCTCTGCGATGAGGTATTTTCCATATGTTCCTGGA
GGTCCGTGCCTGTATATTCGTTAATGTCGACATCTGCCTATGTGCCTGTGTAT
CGGTGCATAGGAGTATGTCTGTGCATCCCTGTATATATTATCTGTGCATATTT
GCATAATTCATAAACGAATATTTAATTACAGTAGTGTTGCGCGAGCCCCGATC
CATTGATCTGCTCACGACTGTAGCACTTAGAATCGCACAGTGCACAGCCAGT
GAGCTGGCCACAGGAGAGGGACATAGGCCTGATTGCTGGGACGCGGATGAG
AGATCAATCGTGTTGTTCCTTACGATAACCTAATCAGCACCACCGAATTATAC
GAGACTGCATTAACTCACATCTGCTAAAGGTTTCGCTTATTCCTTTTACATCC
GAATGTCCATCCTGTTATCTTTAATATTCCTTAATGTGCGATGTCCATATCCCT
TCTAAAAAAAAAAACAGCCAGGCATAGTTTTTGAGCCTGGAAAACTTACCGC
AGGCTTCATAGAAGCCATATCCCGAATAATACTCCATATACCCCCCCCCTTC
CCCAACCGTTCTGTATAGAACGAGAATTTGCCATTTAAGCAGTCTGGGGCCG
AGAGATGTTGCCCCAGAAGTTTTCCACATAGCTAAGTTTATCTCATACTTCGG
AACTCCTGGAGCCAACAAATCCCCTGACCATGTAACTCAAAATAGTTCTTCC
GAGTCTAAGCTACACGGTAAGGAAAATTTGTTACCCCAGAGGATTTTTTTATG
TCAGTAAATCGATAAATAATGCCTTTAACCCTTTCCTTTATGTTGATCTTCCCG
AAACTATGAAAACTATTATATATAACTAGGGGAGAAGAAACATGGGGCATA
GACGATGTGCTGCTGAGAGTCACAATGCGGATCATCAGGGTCTCCCGTCACC
TGGAAACCACCAGACCGTAGACTGAATATCCGAGGGAAACTGAATATAAATC
TGGCCCGAATACAAGGAATCCTGTTCGGGATCCTCGGTAAGACGAGCATAAA
GCCTCTCCGGCTCCGGAGCCGGATGTGGGGGAGATGGGGTAAAAAGGGGAG

FIG 25 CONT

CCTGGCCAACAGGACAAAGCTGAGCGTAAACCGtCCCCGGCGATGGAGGGGT
ACACGGCTCGGTAACAGGACACAATGCAGGGAAGATGCCCTCCGGAGATGG
AGGCTGGGGAGGGCAGAAGAGGGAATGGGGAGTACAGATGGGAGGTGGTGG
GGTCGAGCAGAGCTGGGCGCAAAGCTCCTCCGCATCGGGAGGAGGGGGGGT
ACAGATAGGAGGTTGGAGGGGGGAAGGCCCCGGAGCGTAGATAATATGGGG
AGTAGAGATGGGAGGTGGTGGGGTCGAGCAGAGCCCCGGAGCGTAGAAAAT
ATGGGGAGTAGAGATGGGAGGTGGTGGGGTCGAGCAGAGCTGGGCGCAAAG
CTCCTCCGCATCGGGAGGAGGGGGGGTACAGATAGGAGGTTGGAGGGGGGA
AGGCCCCGGAGCGTAGATAATATGGGGAGTAGAGATGGGAGGTGGGGTCGA
GCAGAGCTGGGCGCAAAGTTCCTCCGTATCGGGAGGAGGGGGGGTACAGAT
AGGAGGTTGGGAACCGGAGCAATGTGGAGCGTTAGGTTCATCCGGTGAGGG
AGGTGGAGGAGTGCAAATGGGAGGTTCAGGAACGGGATCGTGCGGGTGGT
AAGCAGTCCAAGGGTCACCGTTAGGGGTACCGCCATAGGGCAAACTGGCTCA
TGACAAGCCAACTGTACACGCAGGGACGTGCACTCAGTCCTTAGATCTCGAA
TTTCCTTACGTAGGTGTTCATTGGCCCTCTGCAGCTCTTCACATGCTTCATGGA
GTTTGTCTACATAGTCCGTCTGCTCCCTGCGTCTTCTCCGAGAGGCGTCACGA
TTCCTTTTTCTCCTCCTTTCCAGCTTCTGTTTCTCCTCCTCAGATAGGCCGTCA
GGGAAGGGGTGTTTGGAGGGGCTGTTGGGGATGTCGTGACTTTTCCTTTTTTT
CCGTCTCGAAGTCGACCCGAGAGAAAGATCGAGGGGGGACGGATCGTCAGC
GGGACTGTAGGGCATAGCGCCCGGCTCTGGCTCCTGAGACATCTCTTTACAC
CTGTACCGTGCCCGCCTTCTCCCTGGTATACACCTGCAAGAGACGCCTGCCTA
GGAATCAGTGTGCGGAATTTATTCTTAACATTCCAGCACCAACCTCCCCGAAC
CAAAATAATAATTAAAAAAGCAACACCCACAGACCCGAAAGTATTGAAGAA
TTACACGTTCGCGAACGGTCACAATTCACCTGTCATTTATAAAGGAGCAATA
GTTTATTTAAGAGGTAGGTATAAATCGATCATTTCCCCCCCCCCCCCCGTCT
CCGTATCACTCCCGAACCATTAGATATCAGTCGATCCAGCCCCCACGTCATG
CATGACTATCGTCTTTATATCACCGAATT

FIG 26

EcoQ fragment from the CVI988 strain coding for the regular form of Meq gene (SEQ ID NO: 22):

AATTCAAACTATTCTTGTAATGTCGTACGAGCCTCGTTCCGTTCGCTCTTTCAT
GCGCAGCATTACCGGTGTAAATGTAATAATGCCGCACAGTGAACAAGCAAAA
GGGGAAGAGAGTCTCCGGATAGCCGTTACAATCCAGTAACGACTTAACGCAG
ATTACTCCTGCATAAGCGTCTCTGCGATGAGGTATTTTCCATATGTTCCTGGA
GGTCCGTGCCTGTATATTCGTTAATGTCGACATCTGCCTATGTGCCTGTGTAT
CGGTGCATAGGAGTATGTCTGTGCATCCCTGTATATATTATCTGTGCATATTT
GCATAATTCATAAACGAATATTTAATTACAGTAGTGTTGCGCGAGCCCCGATC
CATTGATCTGCTCACGACTGTAGCACTTAGAATCGCACAGTGCACAGCCAGT
GAGCTGGCCACAGGAGAGGGACATAGGCCCGATTGCTGGGACCCGGATGAG
AGATCAATCGTGTTGTTCCTTACGATAACCTAATCAGCACCACCGAATTATAC
GAGACTGCATTAACTCACATCTGCTAAAGGTTTCGCTTATTCCTTTTACATCC
GAATGTCCATCCTGTTATCTTCAATATTCCTTAATGTGCGATGTCCATATCCCT
TCTAAAAAAAAAAACAGCCAGGCATAGTTTTTGAGCCTGGAAAACTTACCGC
AGGCTTCATAGAAGCCATATCCCGAATAATACTCCATATACCCCCCCCCCTT
CCCCAACCGTTCTGTATAGAACGAGAATTTGCCATTTAAGCAGTCTGGGGCC
GAGAGATGTTGCCCCAGAAGTTTTCCACATAGCTAAGTTTATCTCATACTTCG
GAACTCCTGGAGCCAACAAATCCCCTGACCATGTAACTCAAAATAGTTCTTC
CGAGTCTAAGCTACACGGTAAGGAAAATTTGTTACCCCAGAGGATTTTTTAT
GTCAGTAAATCGATAAATAATGCCTTTAACCCTTTCCTTTATGTTGATCTTCCC
GAAACTATGAAAACTATTATATATAACTAGGGGAGAAGAAACATGGGGCAT
AGACGATGTGCTGCTGAGAGTCACAATGCGGATCATCAGGGTCTCCCGTCAC
CTGGAAACCACCAGACCGTAGACTGAATATCCGAGGGAAACTGAATATAAAT
CTGGCCCGAATACAAGGAATCCTGTTCGGGATCCTCGGTAAGACGAGCATAA
AGCCTCTCCGGCTCCGGAGCCGGATGTGGGGGAGATGGGGTAAAAAGGGGA

FIG 26 CONT

GCCTGGCCAACAGGACAAAGCTGAGCGTAAACCGTCCCCGGCGATGGAGGG
GTACACGGCTCGGTAACAGGACACAATGCAGGGAAGATGCCCTCCGGAGAT
GGAGGCTGGGGAGGGCAGAAGAGGGAATGGGGAGTACAGATGGGAGGTGGT
GGGGTCGAGCAGAGCTGGGCGCAAAGCTCCTCCGCATCGGGAGGAGGGGGG
GTACAGATAGGAGGTTGGAGGGGGGAAGGCCCCGGAGCGTAGATAATATGG
GGAGTAGAGATGGGAGGTGGGGTCGAGCAGAGCTGGGCGCAAAGTTCCTCC
GTATCGGGAGGAGGGGGGGTACAGATAGGAGGTTGGGAACCGGAGCAATGT
GGAGCGTTAGGTTCATCCGGTGAGGGAGGTGGAGGAGTGCAAATGGGAGGT
TCAGGAACGGGATCGTGCGGGGTGGTAAGCAGTCCAAGGGTCACCGTTAGGG
GTACCGCCATAGGGCAAACTGGCTCATGACAAGCCAACTGTACACGCAGGGA
CGTGCACTCAGTCCTTAGATCTCGAATTTCCTTACGTAGGTGTTCATTGGCCC
TCTGCAGCTCTTCACATGCTTCATGGAGTTTGTCTACATAGTCCGTCTGCTCCC
TGCGTCTTCTCCGAGAGGCGTCACGATTCCTTTTCTCCTCCTTTCCAGCTTCT
GTTTCTCCTCCTCAGATAGGCCGTCAGGGAAGGGGTGTTTGGAGGGGCTGTT
GGGGATGTCGTGACTTTTCCTTTTTTCCGTCTCGAAGTCGACCCGAGAGAAA
GATCGAGGGGGGACGGATCGTCAGCGGGACTGTAGGGCATAGCGCCCGGCT
CTGGCTCCTGAGACATCTCTTTACACCTGTACCGTGCCCGCCTTCTCCCTGGT
ATACACCTGCAAGAGACGCCTGCCTAGGAATCAGTGTGCGGAATTTATTCTT
AACATTCCAGCACCAACCTCCCCGAACCAAAATAATAATTAAAAAAGCAACA
CCCACAGACCCGAAAGTATTGAAGAATTACACGTTCGCGAACGGTCACAATT
CACCTGTCATTTTATAAGGAGCAATAGTTTATTTAAGAGGTAGGTATAAATC
GATCATTTCCCCCCCCCCCGTCTCCGTATCACTCCCGAACCATTAGATATC
AGTCGATCCAGCCCCCACGTCATGCATGACTATCGTCTTTATATCACCGAAT
T

MAREK'S DISEASE VIRUS VACCINE COMPOSITIONS AND METHODS OF USING THEREOF

CROSS-REFERENCE TO RELATED APPLICATIONS

This application claims the benefit of Provisional Application Ser. No. 61/082,022, filed Jul. 18, 2008

STATEMENT OF GOVERNMENT SUPPORT

This invention was made in part with government support under grant number 2004-35204-14840, from the USDA-CREES-NRI. As such, the United States government has certain rights to the invention.

FIELD OF THE INVENTION

The present invention relates to the field of poultry health. In particular, the present invention relates to methods and compositions for the prevention of Marek's disease. In some embodiments, the invention relates to the prevention and treatment of Marek's disease by administering vaccine compounds as disclosed herein. In further embodiments, the invention relates to methods and compositions comprising the synthesis and use of vaccines that are generated by introducing mutations into the Meq gene of the Marek's disease virus.

BACKGROUND OF THE INVENTION

Marek's disease virus (MDV) is a pathogenic agent capable of inducing cancer in chickens and represents a major obstacle in commercial poultry. Marek's disease (MD) is a lymphoproliferative and neuropathic disease of chickens, caused by a highly contagious, cell-associated, oncogenic herpesvirus called Marek's disease virus (MDV) (Calnek, B. W. (2001) Pathogenesis of Marek's disease virus infection, Curr Top Microbiol Immunol 255, 25-55.). MD was originally described as 'polyneuritis' affecting the peripheral nerves in roosters (Marek, J. (1907) Multiple Nervenentziindung (Polyneuritis) bei Hühnern, Dtsch. Tierärztl. Wochenschr 15, 417-421.). In the 1950s visceral forms of the disease referred to as 'acute lymphomatosis', was recognized in the USA particularly in broilers (Benton, W. J., and Cover, M. S. (1957) The increased incidence of visceral lymphomatosis in broiler and replacement birds, Avian Dis 1, 320-327.). This form of the disease increased in severity with the rapid expansion of the vertically integrated poultry operations after World War II. In the 1970, prior to use of MDV vaccines, the losses from carcass condemnation of broilers accounted for about $200 millions per annum, representing condemnation of 1.5% of broilers examined. After the introduction of vaccines, the broiler condemnation rates have steadily declined to less than 0.01% today (Witter, R. L. (2001) Protective efficacy of Marek's disease vaccines, Curr Top Microbiol Immunol 255, 57-90.). However, MD still remains an economical important disease because of vaccination breaks and emergence of more virulent strains. While currently employed immunization methods demonstrate some efficacy against the disease, the virus typically persists in chicken houses and continues to evolve, oftentimes breaking through vaccinal immunity. The Meq oncogene, which resides in MDV, represents an attractive target for vaccinal control and prevention of Marek's disease, as deletion of Meq results in total loss of MDV oncogenic potential as provided for in U.S. Pat. No. 7,214,524 to Reddy et al., hereby incorporated by reference. However, previously disclosed Meq deleted vaccines were shown to have variable protection in chickens challenged with highly virulent MDV strains and they appear to cause immunosuppression as seen by immune organ atrophy in vaccinated chickens. Thus, there is a need for improved vaccines directed against Marek's disease in poultry.

SUMMARY OF THE INVENTION

The present invention relates to the field of poultry health. In particular, the present invention relates to methods and compositions for the prevention of Marek's disease. In some embodiments, the invention relates to the prevention and treatment of Marek's disease by administering vaccine compounds and/or formulations as disclosed herein. In further embodiments, the invention relates to methods and compositions comprising the synthesis and use of vaccines that are generated by introducing mutations into the Meq gene of the Marek's disease virus. Without intending to be limited by any mechanism, the presence of Meq may be necessary for efficient entry into latency and therefore required in safe and effective vaccines. Modifications of the MDV genes may form attenuated MDV able to confer superior protection without causing lymphoid organ atrophy and are capable of inducing protective immunity against emerging more virulent viruses.

In further embodiments, the invention relates to methods and compositions for the synthesis (e.g. construction) and use of vaccines that are generated by introducing mutations into a) the Meq gene, an MDV oncogene, and, optionally, b) at least one gene involved in replication in lymphocytes of the Marek's disease virus. It is believed such vaccines will provide protection against virulent strains, and yet not cause lymphoid organ atrophy.

In some embodiments, the invention relates to a method of immunizing subjects against Marek's disease comprising: providing a subject (e.g. a subject at risk for or exhibiting symptoms associated with Marek's disease), and a composition comprising a modified strain of Marek's disease virus (e.g. with mutations in the Meq gene such as those described herein) and administering said composition to said subject. In further embodiments, said composition further comprises (optionally) an adjuvant and/or a pharmaceutically acceptable carrier. In still further embodiments, said subject is a bird, such as a chicken. In additional embodiments, the mode of said administration is selected from the group consisting of optical, oral, parenteral, mucosol, buccal, cloacal, vaginal, rectal, sublingual, inhalation, insufflation, intravenous, intrathecal, subcutaneous and intramuscular.

In one embodiment, the present invention comprises a vaccine comprising Marek's disease virus nucleic acid having at least one mutation (e.g. in the Meq gene). In one embodiment, the nucleic acid encodes an Meq protein. In one embodiment, the nucleic acid comprises a cosmid. In one embodiment, the cosmid is selected from the group comprising SN5, P89, SN16, A6 and B40. In one embodiment, the Marek's disease virus comprises a strain Md5. In one embodiment, the cosmid comprises a mutation, thereby generating a mutated nucleic acid (e.g. encoding an altered protein). In one embodiment, the mutation may be selected from the group comprising a phosphorylation site, a basic region, a leucine zipper region, or a transactivation domain. In one embodiment, mutated nucleic acid encodes an Meq CVI/Md5 protein mutant having point mutations selected from the group comprising A71S and K77E. In one embodiment, a mutated nucleic acid encodes an Meq Md5/CVI protein mutant having point mutations selected from the group consisting of A217P, V283A, T320I and T326I. In one embodiment, a mutated nucleic acid encodes an Md5-CVIL protein mutant having point mutations selected from the group comprising A217P, V283A, T320I and T326I. In one embodiment, a mutated nucleic acid encodes an Md5-CVIL mutant having an insertion mutation comprising amino acid positions 194-253.

In one embodiment, the present invention contemplates an Md5 virus comprising Meq mutations. In one embodiment, the Meq mutations are directed at a DNA binding domain. In one embodiment, the DNA binding domain mutations are selected from the group comprising A71S, A71D, and/or R72P. In one embodiment, the Meq mutations are directed at phosphorylation sites. In one embodiment, the phosphorylation site mutations are selected from the group comprising T28A, S42A, S42D, and/or T79A. In one embodiment, the Meq mutations are directed at the leucine zipper domain. In one embodiment, the Meq-Md5 leucine zipper domain is replaced with a Fos leucine zipper domain.

In one embodiment, the present invention contemplates a chimeric Meq protein. In one embodiment, the chimeric protein comprises an Md5-CVI chimeric Meq protein. In one embodiment, the chimeric protein comprises an EcoQ fragment. In one embodiment, the EcoQ fragment is derived from CVI988 and includes, but is not limited to EcoQ-CVIL and/or EcoQ-CVI.

In some embodiments, the invention relates to a vaccine comprising: at least one modified Marek's disease virus, and (optionally) an adjuvant and/or a pharmaceutically acceptable carrier. In further embodiments, said modified Marek's disease virus is selected from the group consisting of rMd5-CVIL, rMd5-CVI, rMd5-CVI/Md5, rMd5-Md5/CVI, rMd5-MF, rMd5-MeqT29A, rMd5-MeqS42A, rMd5-MeqS42D, rMd5-MeqT79A, rMd5-MeqA71S, rMd5-MeqA71D, rMd5-MeqA71E/R72P. In still further embodiments, said modified Marek's disease virus further comprises the amino acid sequences of SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15 and SEQ ID NO:16.

In one embodiment, the present invention contemplates a transfected cell comprising an Md5 nucleic acid. In one embodiment, the transfected cell comprises a fibriblast, such as a primary duck embryonic fibroblast cell. In one embodiment, the Md5 nucleic acid comprises a cosmid selected from the group comprising P89, SN16, B40, SN5, A6, SN16, SN5-mutant, or A6-mutant. In one embodiment, the Md5 nucleic acid comprises an inserted nucleic acid sequence encoding a fusion protein selected from the group comprising SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15 and SEQ ID NO:16.

In one embodiment, the present invention contemplates a transfected cell comprising an Md5 nucleic acid. In one embodiment, the transfected cell comprises a fibroblast, such as a primary duck embryonic fibroblast cell. In one embodiment, the Md5 nucleic acid comprises a cosmid selected from the group comprising P89, SN16, B40, SN5, A6, SN16, SN5-mutant, or A6-mutant. In one embodiment, the Md5 nucleic acid is derived from a plurality of overlapping cosmids selected from the group comprising P89, SN16, B40, SN5, A6, SN16, SN5-mutant, or A6-mutant. While not intending to limit the invention by the method in which mutations are introduced, in one embodiment, the Md5 nucleic acid comprises an inserted nucleic acid sequence comprising the Meq gene from CVI988 (e.g. as a replacement for the Meq gene of Md5) and deletion in the vIL8 and/or vTR genes. In one embodiment, the Md5 nucleic acid comprises an inserted nucleic acid sequence with the containing the Meq gene from CVI988 and deletion in the vIL8 and vTR genes comprising SEQ ID NO:20 disclosed in FIG. 24. In one embodiment, the Md5 nucleic acid comprises an inserted nucleic acid sequence with the containing the Meq gene from CVI988 and deletion in the vIL8 and vTR genes comprising SEQ ID NO:20 disclosed in FIG. 24 and nucleic acid sequence encoding a fusion protein selected from the group comprising SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15 and SEQ ID NO:16.

In one embodiment, the present invention contemplates a transfected cell comprising an Md5 nucleic acid. In one embodiment, the transfected cell comprises a fibroblast, such as a primary duck embryonic fibroblast cell. In one embodiment, the Md5 nucleic acid comprises a cosmid selected from the group comprising P89, SN16, B40, SN5, A6, SN16, SN5-mutant, or A6-mutant. Again, while not intending to limit the invention by the method in which mutations are introduced, in one embodiment, the Md5 nucleic acid comprises an inserted nucleic acid sequence with the containing the Meq gene from CVI988 (e.g. as a replacement for the Meq gene of Md5) and deletion in the vIL8 gene. In one embodiment, the Md5 nucleic acid comprises an inserted nucleic acid sequence with the containing the Meq gene from CVI988 and deletion in the vIL8 gene comprising SEQ ID NO: 19 disclosed in FIG. 21. In one embodiment, the Md5 nucleic acid comprises an inserted nucleic acid sequence with the containing the Meq gene from CVI988 and deletion in the vIL8 gene comprising SEQ ID NO: 19 disclosed in FIG. 21 and nucleic acid sequence encoding a fusion protein selected from the group comprising SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15 and SEQ ID NO:16.

In one embodiment, the present invention contemplates a transfected cell comprising an Md5 nucleic acid. In one embodiment, the transfected cell comprises a fibroblast such as a primary duck embryonic fibroblast cell. In one embodiment, the Md5 nucleic acid comprises a cosmid selected from the group comprising P89, SN16, B40, SN5, A6, SN16, SN5-mutant, or A6-mutant. In one embodiment, the Md5 nucleic acid comprises an inserted nucleic acid sequence with the containing the Meq gene from CVI988 and deletion in the vTR gene. In one embodiment, the Md5 nucleic acid comprises an inserted nucleic acid sequence with the containing the Meq gene from CVI988 and deletion in the vTR gene and nucleic acid sequence encoding a fusion protein selected from the group comprising SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15 and SEQ ID NO:16.

In one embodiment, the present invention contemplates a transfected cell comprising an Md5 nucleic acid. In one embodiment, the transfected cell comprises a fibroblast such as a primary duck embryonic fibroblast cell. In one embodiment, the Md5 nucleic acid comprises a cosmid selected from the group comprising P89, SN16, B40, SN5, A6, SN16, SN5-mutant, or A6-mutant. In one embodiment, the Md5 nucleic acid comprises an inserted nucleic acid sequence encoding a fusion protein with point mutations in the DNA binding domain of Meq at positions 71 and 72 including at least one of the following: A71S, A71S, A71D and R72P.

In one embodiment, the Md5 nucleic acid comprises an inserted nucleic acid sequence encoding a fusion protein with point mutations phosphorylations sites found at position 28, 42 and 79 in the Meq gene of Md5 including at least one of the following: T28A, S42A, S42D and T79A.

A variety of methods exist for introducing mutations. Without intending to limit the invention to any particular technique, in one embodiment, the Md5 nucleic acid comprises an inserted nucleic acid sequence encoding a fusion protein with point mutations in the DNA binding domain of Meq at positions 71 and 72 including at least one of the following: A71S, A71S, A71D and R72P and phosphorylations sites found at position 28, 42 and 79 in the Meq gene of Md5 including at least one of the following: T28A, S42A, S42D and T79A.

In one embodiment, the Md5 nucleic acid comprises an inserted nucleic acid sequence encoding a fusion protein with point mutations in the DNA binding domain of Meq at positions 71 and 72 including at least one of the following: A71S, A71S, A71D and R72P; and phosphorylations sites found at position 28, 42 and 79 in the Meq gene of Md5 including at least one of the following: T28A, S42A, S42D and T79A; and deletion in the vTR gene.

In one embodiment, the Md5 nucleic acid comprises an inserted nucleic acid sequence encoding a fusion protein with point mutations in the DNA binding domain of Meq at positions 71 and 72 including at least one of the following: A71S, A71S, A71D and R72P; and phosphorylations sites found at position 28, 42 and 79 in the Meq gene of Md5 including at least one of the following: T28A, S42A, S42D and T79A; and deletion in the vIL8 and vTR genes.

In one embodiment, the present invention contemplates a method of immunizing subjects against Marek's disease virus comprising: a) providing: i) a subject (e.g. one at risk for or exhibiting symptoms associated with Marek's disease), and ii) a composition comprising a modified strain of Marek's disease virus, said modified strain comprising a mutated Meq gene (e.g. the rMd5 virus with a mutated Meq gene); b) administering said composition to said subject (thereby generating protective immunity against virulent strains). In one embodiment, said composition further comprises a pharmaceutically acceptable carrier and/or adjuvant. In one embodiment, said subject is a bird, such as a chicken. In one embodiment, the mode of said administration is selected from the group consisting of optical, oral, parenteral, mucosol, buccal, vaginal, rectal, sublingual, inhalation, insufflation, intravenous, intrathecal, subcutaneous and intramuscular.

The present invention also contemplates methods of constructing recombinant viruses, comprising a) providing overlapping cosmids, and b) manipulating said overlapping cosmids so as to generate a recombinant Marek virus strain. In one embodiment, the strain is Md5 and the cosmids are selected from the group comprising P89, SN16, B40, SN5, A6, SN16, SN5-mutant, or A6-mutant. In one embodiment, the method further comprises replacing a wild-type Meq gene with a mutated Meq gene.

The present invention also contemplates, in one embodiment, a vaccine comprising: a) at least one modified Marek's disease virus comprising a mutated Meq gene, and (optionally) b) a pharmaceutically acceptable carrier and/or adjuvant. In one embodiment, said modified Marek's disease virus is selected from the group consisting of rMd5-CVIL, rMd5-CVI, rMd5-CVI/Md5, rMd5-Md5/CVI, rMd5-MF, rMd5-MeqT29A, rMd5-MeqS42A, rMd5-MeqS42D, rMd5-MeqT79A, rMd5-MeqA71S, rMd5-MeqA71D, rMd5-MeqA71E/R72P. In one embodiment, said modified Marek's disease virus further comprises the amino acid sequences of SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15 and SEQ ID NO:16. In one embodiment, said modified Marek's disease virus further comprises a mutation in at least one gene involved in replication in lymphocytes. In one embodiment, said virus is the rMd5 virus, wherein the rMd5 nucleic acid comprises an inserted nucleic acid sequence comprising the Meq gene from CVI988. In one embodiment, said mutation in at least one gene involved in replication in lymphocytes is selected from a deletion in the vIL8 gene and a deletion in the vTR gene. In one embodiment, said mutation in at least one gene involved in replication in lymphocytes is a deletion in the vIL8 gene. In one embodiment, said mutation is a deletion of the vIL8 gene comprises the nucleic acid sequences of SEQ ID NO:19. In one embodiment, said mutation in at least one gene involved in replication in lymphocytes is selected from a deletion in the vTR gene. In one embodiment, said mutation is a deletion of the vIL8 gene and the vTR gene further comprises the nucleic acid sequences of SEQ ID NO:20.

The present invention also contemplates, in one embodiment, a method of altering (e.g. altering pathogenicity or other aspects) a recombinant Marek's disease virus comprising: a) providing: i) fibroblasts; and ii) a composition comprising a modified strain of Marek's disease virus, said modified strain comprising a mutated Meq gene; and b) passaging said modified strain in said fibroblasts so as to reduce the pathogenicity of said modified strain. Altering pathogenicity can be readily measured in vivo by comparing passaged virus with unpassaged virus in susceptible animals (e.g. antibody negative chickens), followed by enumeration of lesions. In one embodiment, such a comparison reveals a 20% or more reduction in lesions or animals with lesions (and preferably a 30%-40% reduction, or more, in lesions or animals with lesions). In one embodiment, said fibroblasts are selected from the group of chicken fibroblasts and duck fibroblasts. In one embodiment, said passaging is performed at least 20 times. In one embodiment, said modified Marek's disease virus is selected from the group consisting of rMd5-CVIL, rMd5-CVI, rMd5-CVI/Md5, rMd5-Md5/CVI, rMd5-MF, rMd5-MeqT29A, rMd5-MeqS42A, rMd5-MeqS42D, rMd5-MeqT79A, rMd5-MeqA71S, rMd5-MeqA71D, rMd5-MeqA71E/R72P.

As noted above, in one embodiment, the present invention contemplates passaging a virus construct comprising a mutation in the Meq gene. In a preferred embodiment, the virus is passaged more than 10 times, preferably more than 20 times, more preferably at least 30 times (and up to 50 or even 100 times).

BRIEF DESCRIPTION OF THE DRAWINGS

For a more complete understanding of the features and advantages of the present invention, reference is now made to the detailed description of the invention along with the accompanying figures.

The patent or application file contains at least one figure executed in color. Copies of this patent or patent application publication with figure will be provided by the Office upon request and payment of the necessary fee.

FIG. 6 shows Marek's disease gross lesions in 15×7 chickens infected with CVI988, rMd5, rMd5-CVI-LMeq and rMd5-CVI-Meq viruses.

FIG. 7 shows the protective efficacy of CVI988, rMd5-CVI-LMeq and rMd5-CVI-Meq against vv+ 648A virus challenge.

FIG. 8 shows a comparison of length of genomic regions of recombinant rMd5 generated from cosmid clones and published Md5 sequence.

FIG. 9 shows pathogenesis and protection studies of rMd5/CVI-Meq, rMd5/CVI-LMeq and their cell culture (duck or chicken embryo fibroblasts) adapted derivatives in chickens.

Figure 12:
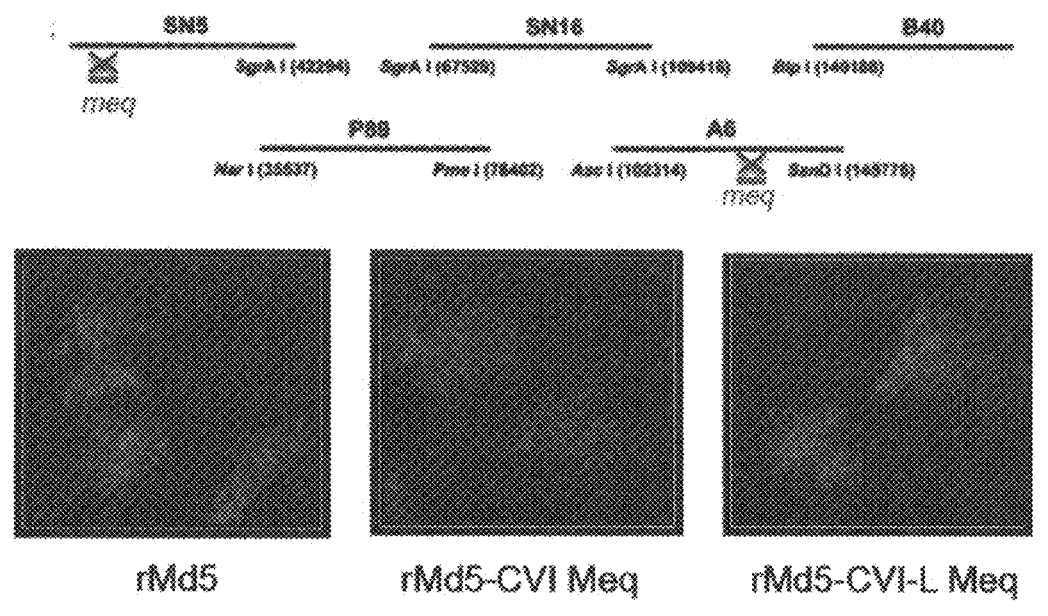

FIG. 12 shows the generation of rMd5 viruses containing the CVI meq (rMd5-CVI Meq) and CVI-L meq genes (rMd5-CVI-L Meq). Top panel: schematic representation of the Md5 cosmids indicating the location of the meq gene. Bottom panel: Immunofluorescence analysis of DEF cells infected with recombinant parental virus, rMd5, rMd5-CVI Meq and rMd5-CVI-L Meq. Immunofluorescence was carried out using a mouse monoclonal antibody specific for the MDV early protein pp 38. Reactivity with the pp 38 monoclonal antibody was visualized using a goat anti-mouse labeled with Texas Red and a fluorescence microscope.

FIG. 14 shows transactivation of the meq promoter by chimeric Meq proteins (A) and Meq single amino acid mutants (B). DF-1 cells were co-transfected with either 250 ng of pGL3-meq promoter and 500 ng of one of Chimeric Meq expressing vectors (A) or Meq single amino acid mutants (B). Twenty-four hours after the transfection, cells were collected and analyzed for luciferase activity. Values were reported as fold activation relative to the luciferase activity of vector. The experiment was done three times in triplicate. Error bars indicate SEM.

Figure 15:
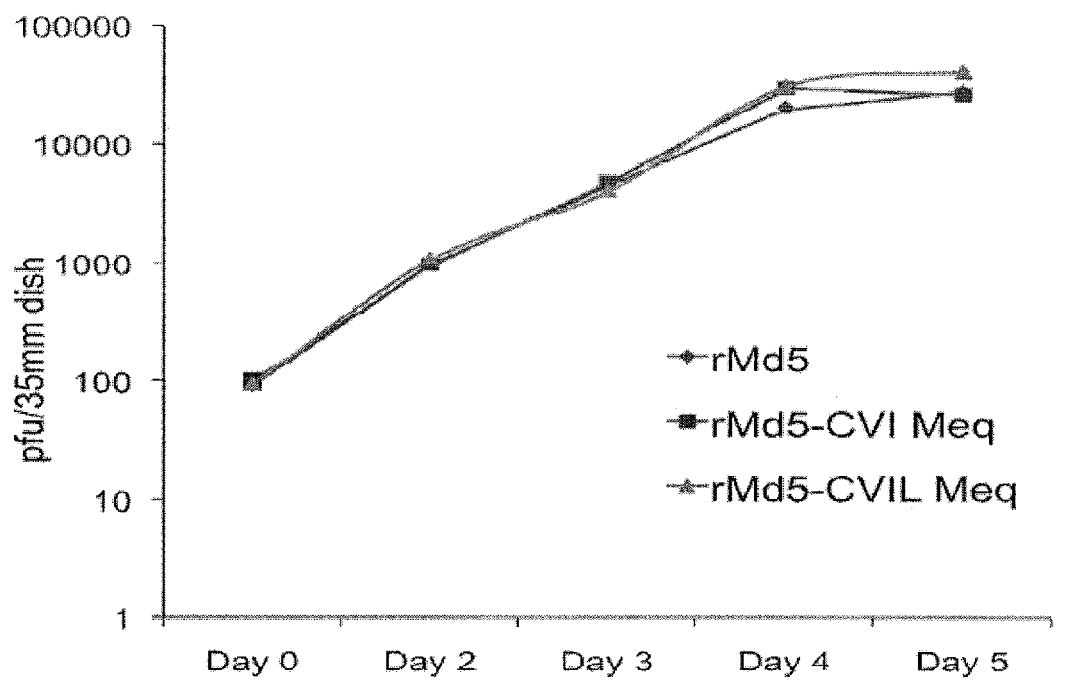

FIG. 15 shows the in vitro growth properties of rMd5, rMd5-CVI Meq and rMd5-CVI-L Meq. To compare the growth characteristics of rMd5, rMd5-CVI Meq and rMd5-CVI-L Meq, DEF were seeded on 35 mm plates and inoculated with 100 plaque-forming units (pfu) of each virus. On days 2, 3, 4 and 5 after inoculation, the infected cells were trypsinized, serial dilutions inoculated onto DEF monolayers, seeded on 35 mm plates, and plaques at the different dilutions counted 7 days later. Day 0 indicates the titer of the virus in the inoculum. The experiment was performed in duplicate. No differences in in vitro growth properties were observed among any of the viruses tested.

FIG. 16 shows in vivo characterization of rMd5, rMd5-CVI Meq and rMd5-CVI-L Meq viruses. To study the role of the CVI Meq and CVI-L Meq in oncogenesis, SPF day old chicks (15 per group) were inoculated subcutaneously with 2,000 pfu of one of the following viruses: CVI988/Rispens, rMd5, rMd5-CVI Meq or rMd5-CVI-L Meq and reared in modified horsfall-breuer isolation units for 8 weeks. Weekly mortality was recorded and all chickens were necropsied at time of death or at termination of the experiment and evaluated for MDV-specific gross and microscopic tumors in the viscera and nerves. To study the role of CVI Meq and CVI-L Meq on viral replication, at day 6 post-injection (PI), 3 chickens from each group were euthanized and lymphoid organs were collected for IHC analysis. To study the role of CVI Meq and CVI-L Meq in virus latency and reactivation, blood samples, from randomly selected chickens, were collected in heparin at day 38 PI, and examined by reactivation assays. To study the role of CVI Meq and CVI-L Meq on horizontal transmission, 3 uninoculated day-old chicks were included in each of test groups and served as contacts. At 8 weeks post inoculation buffy coats were obtained from heparinized blood by centrifugation at 500×g and the presence of virus in contact birds determined by immunofluorescence and PCR.

Figure 17:
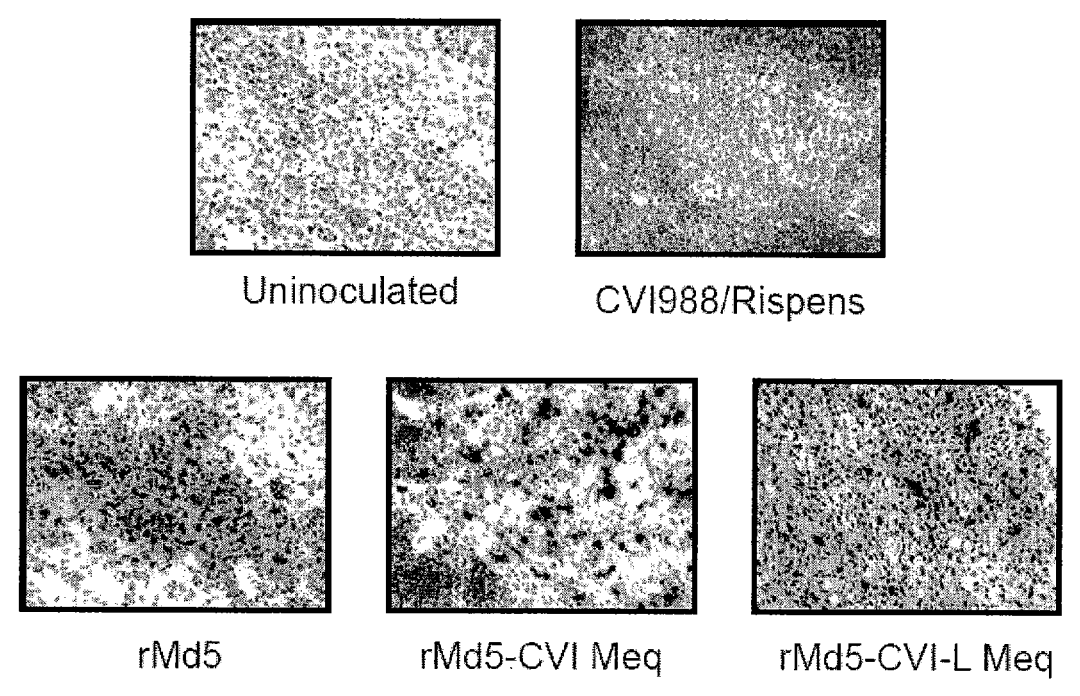

FIG. 17 shows the infection of thymus of infected chickens. The immunohistochemistry (IH) of thymus sections using MDV specific anti-pp 38 (H19) mouse monoclonal antibody at 6 days post-injection (PI) was observed. Positive cells are stained brown and counterstaining was performed with hematoxylin. The pp 38 antigen was detected in rMd5, rMd5-CVI Meq and rMd5-CVI-L Meq but not in CVI988/Rispens and uninoculated control.

FIG. 19 shows the incidence of Marek's disease (MD) in chickens inoculated with rMd5, rMd5-CVI Meq, rMd5-CVI-L Meq and CVI988/Rispens. Maternal antibody positive and negative chickens were inoculated with 2,000 plaque-forming units (pfu) of the indicated viruses at 1 day of age and maintained in isolation for 8 weeks. Uninoculated chickens served as negative controls. Weekly mortality was recorded. The numbers shown indicate number of chickens with MD/total numbers tested.

FIG. 21A-E shows representative embodiments of fusion Meq proteins (SEQ ID NOs: 7-11). FIG. 21A shows the sequence for Meq-Fos (MF) protein sequence encoded by rMd5-MF (SEQ ID NO: 7). FIG. 21B shows the sequence for CVI Meq protein sequence encoded by rMd5-CVI Meq (SEQ ID NO: 8). FIG. 21C shows the sequence for CVI-L Meq protein sequence encoded by rMd5-CVI-L Meq (SEQ ID NO: 9). FIG. 21D shows the sequence for Md5/CVI Meq protein sequence encoded by rMd5 Md5/CVI Meq (SEQ ID NO: 10). FIG. 21E shows the sequence for CVI/Md5 Meq protein sequence encoded by rMd CVI/Md5 Meq (SEQ ID NO: 11).

FIG. 22A-G shows representative embodiments of point mutations in Meq proteins (SEQ ID NOs: 12-18). FIG. 22A shows the sequence for Md5 T28A protein sequence encoded by rMd5 T28A Meq (SEQ ID NO: 12). FIG. 22B shows the sequence for Md5 S42A protein sequence encoded by rMd5 S42A Meq (SEQ ID NO: 13). FIG. 22C shows the sequence for Md5 S42D protein sequence encoded by rMd5 S42D Meq (SEQ ID NO: 14). FIG. 22D shows the sequence for Meq A71S protein sequence encoded by rMd5 A71S Meq (SEQ ID NO: 15). FIG. 22E shows the sequence for Meq A71D protein sequence encoded by rMd5 A71D Meq (SEQ ID NO: 16). FIG. 22F shows the sequence for Meq A71E-R72P protein sequence encoded by rMd5 A71E-R72P Meq (SEQ ID NO: 17). FIG. 22G shows the sequence for Meq T79A protein sequence encoded by rMd5 T79A Meq (SEQ ID NO: 18).

FIG. 23 shows representative embodiment of the BamHI DNA sequence, with deletion of the vIL8 gene from ClaI-NcoI (2807-3606) (SEQ ID NO: 19).

FIG. 24 shows representative embodiment of the MDV DNA sequences (896-5084) with deletion of the BamHI region (1451-4544), that results in the deletion of vTR and vIL8 genes (SEQ ID NO: 20).

FIG. 25 shows representative embodiment of the EcoQ fragment DNA sequence from the CVI988 strain coding for the long form of Meq gene (SEQ ID NO: 21).

FIG. 26 shows representative embodiment of the EcoQ fragment DNA sequence from the CVI988 strain coding for the regular form of Meq gene (SEQ ID NO: 22).

DEFINITIONS

Figure 1:
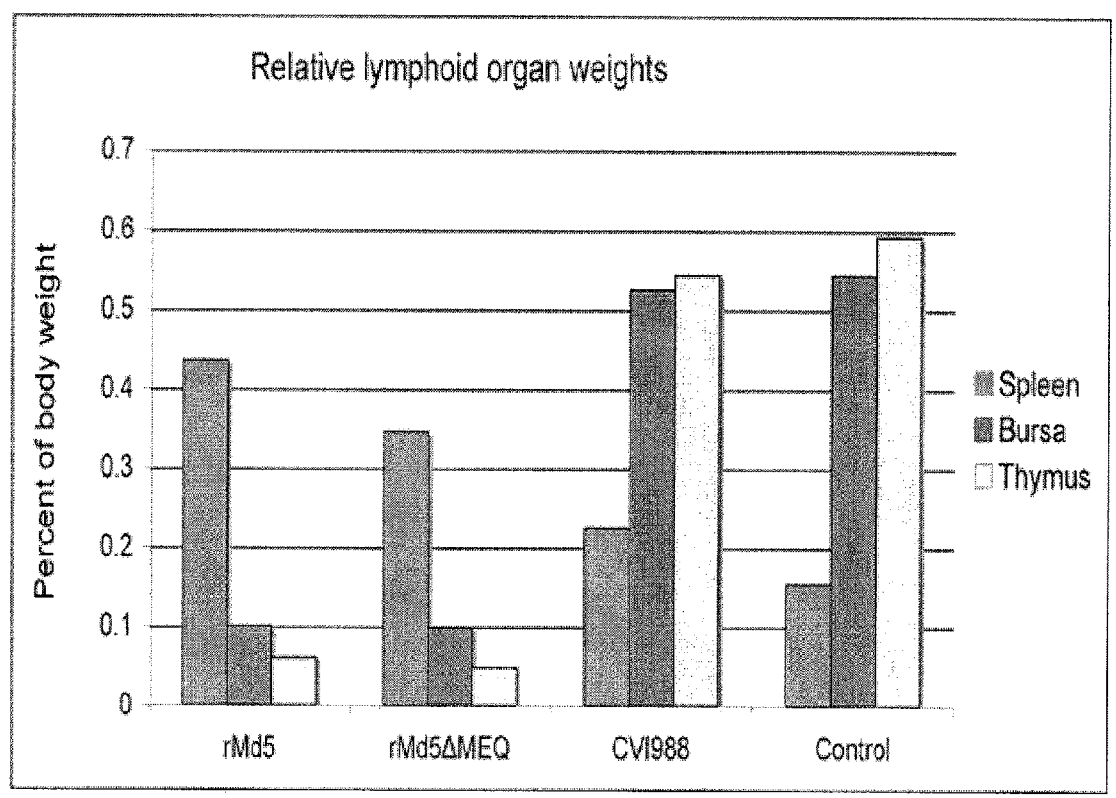
FIG. 1 shows relative weights of spleen, bursa of Fabricius, thymus. Maternal antibody negative (15×7) chickens were infected with 2000 pfu of rMd5, rMd5ΔMeq or CVI988. The bars represent the mean lymphoid organ weights (calculated as a percentage of whole body weight) from 5 chickens.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, "Marek's disease" refers to any disease caused by an α-herpesvirus known as Marek's disease virus (MDV). Generally, Marek's disease occurs in chickens. While not limiting the invention to any particular symptoms or course of pathology, the disease is often characterized by the presence of T cell lymphoma as well as the infiltration of nerves and organs by lymphocytes. The virus may be spread, for example, in dander from feather follicles and transmitted via inhalation.

The term "vaccine" refers to any composition that is used to improve immunity to a particular disease (e.g. by generating an immune response to a virus, or portion thereof, which causes the disease). The term "vaccine" includes, but is not limited to a "cell-associated" or "live" vaccine.

As used herein, the term "recombinant DNA molecule" as used herein refers to any DNA molecule that is comprised of segments of DNA joined together by means of molecular biological techniques.

"Nucleic acid sequence" as used herein refers to an oligonucleotide, nucleotide or polynucleotide, and fragments or portions thereof, and to DNA or RNA of genomic or synthetic origin that may be either single- or double-stranded, and represent the sense or antisense strand.

"Amino acid sequence" as used herein refers to peptide or protein sequence.

"Peptide nucleic acid" as used herein refers to an oligomeric molecule in which nucleosides are joined by peptide, rather than phosphodiester, linkages. These small molecules, also designated anti-gene agents, stop transcript elongation by binding to their complementary (template) strand of nucleic acid as provided for in Nielsen et al., *Anticancer Drug Des.* 8, 53-63 (1993), incorporated herein by reference.

As used herein, the terms "prevent" and "preventing" include the prevention of the recurrence, spread or onset of a disease or disorder. It is not intended that the present invention be limited to complete prevention. In some embodiments, the onset is delayed, or the severity of the disease or disorder is reduced.

As used herein, the terms "treat" and "treating" are not limited to the case where the subject (e.g. patient) is cured and the disease is eradicated. Rather, the present invention also contemplates treatment that merely reduces symptoms, improves (to some degree) and/or delays disease progression. It is not intended that the present invention be limited to instances wherein a disease or affliction is cured. It is sufficient that symptoms are reduced.

"Subject" refers to any animal, but preferably a poultry species, and most preferably a chicken.

The term "pharmaceutically acceptable" as used herein, refers to compounds and/or compositions that are approved by a regulatory agency of the federal or a state government or listed in the U.S. (i.e., for example, the Food & Drug Agency).

The term "carrier" refers to any diluent, adjuvant, excipient or vehicle with which the active compound is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents can be used. When administered to a subject, the pharmaceutically acceptable vehicles are preferably sterile. Water can be the vehicle when the active compound is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The present compositions, if desired, can also contain minor amounts of wetting or emulsifying agents, or pH buffering agents.

15I5×7 chickens (15×7 chickens): These are genetically defined chicken lines that were obtained from USDA, ARS, Avian Disease and Oncology Laboratory, East Lansing Mich. They are progeny of two distinct lines of chickens maintained at the laboratory in Michigan lab Md5 is a very virulent strain of MDV. The rMd5 is a recombinant version of the same virus, that was engineered in the lab. The r stands for recombinant, but genetically they are the same.

SPF (Ab−) chickens: SPF stands for specific pathogen free, Ab− means that the chickens do not have any maternal MDV specific antibodies.

Hyline (Ab+): These are commercial egg laying breed of white leghorn, these chickens are not SPF and will have maternal antibodies to MDV.

Meq is a 339 amino acid nuclear phosphoprotein, is a b-ZIP (basic-region leucine zipper) protein, which shares significant homology in the bZIP domain with the protooncogene c-jun a transcription factor of the AP-1 (activating protein) complex. It can be encoded by DNA sequences found in two forms: LMeq and Meq. LMeq refers to the long form of the Meq gene. The EcoQ fragment from the CVI988 strain coding for the long form of Meq gene of which one embodiment is disclosed in (SEQ ID NO:21). Meq refers to the regular form of the meq. The EcoQ fragment from the CVI988 strain coding for the long form of Meq gene of which one embodiment is disclosed in (SEQ ID NO:22).

DETAILED DESCRIPTION OF THE INVENTION

The present invention relates to the field of poultry health. In particular, the present invention relates to methods and compositions for the treatment of Marek's disease. In some embodiments, the invention relates to the prevention and treatment of Marek's disease by administering vaccine compounds as disclosed herein. In further embodiments, the invention relates to methods and compositions comprising the synthesis and use of vaccines that are generated by introducing mutations into the Meq gene of the Marek's disease virus.

I. Marek's Disease Virus

Marek's disease virus (MDV), the etiologic agent of Marek's disease (MD), is a potent oncogenic herpesvirus which elicits a rapid onset of malignant T-cell lymphomas in chickens within several weeks of infection, resulting in mortality. MDV is classified as an alpha-herpesvirus based on analysis of the viral genome but shares characteristics with gammaherpesviruses due to its tropism and transformation of T-cells. Of the previously described serotypes of MDV, now classified as Gallid herpesvirus 2 (GaHV-2) or Marek's disease virus type 1; Gallid herpesvirus 3 (GaHV-3) or Marek's disease virus type 2 and the Meleagrid herpesvirus 1 (MeHV-1) or turkey herpesvirus only GaHV-2 is oncogenic. In addition, a number of different pathotypes exist within GaHV-2 ranging from mild to very virulent plus.

The search for candidate viral oncogenes in the MDV genome led to the discovery of meq, which is abundantly expressed in MDV transformed cells, and is encoded only by the genome of the oncogenic Marek's disease virus type 1. The meq gene is named after the EcoQ fragment where the gene is located, "Marek's EcoQ", and is found in two copies in the viral genome within the terminal repeat long (TRL) and internal repeat long (IRL) regions. Meq a 339 amino acid nuclear phosphoprotein, is a b-ZIP (basic-region leucine zipper) protein, which shares significant homology in the bZIP domain with the protooncogene c-jun a transcription factor of the AP-1 (activating protein) complex. AP-1 transcription factors are a group of well-characterized transcription factors that are characterized by their ability to bind and regulate sequence specific gene elements, AP-1 sites, which are found in many genes associated with cell proliferation. Transformation by deregulated expression of c-Jun or its viral counterpart v-Jun, is well documented and therefore the shared homology between Meq and Jun is intriguing. In vitro data support the oncogenic nature of Meq, which has been shown to promote anchorage-independent growth, cell-cycle progression, and anti-apoptosis. Recently, in vitro expression of Meq was shown to upregulate similar genes as v-Jun and therefore suggested that Meq transforms via a v-Jun transforming pathway. In addition, knockdown of c-jun diminishes Meq's transforming ability in vitro, strongly suggesting that Meq/jun partnership plays a key role in Meq's oncogenic potential. Yet the most convincing evidence for Meq's oncogenic property was the characterization of a Meq null recombinant MDV virus (rMd5ΔMeq) which replicated in chickens and did not induce tumors. Significantly, the Meq null virus have provided best protectivity in chickens, upon challenging with the most virulent strains of MDV. This points to a potential strategy for further vaccine improvement, where more subtle mutation(s) of Meq is engineered, which abolishes its transforming ability, but retains its ability of establishing infection in vivo and associated antigenicity. One problem to be solved in the art involves a further understanding of the transforming and replication functions of Meq.

II. Marek's Disease Vaccines

In some embodiments, the invention relates to methods and compositions for the prevention of Marek's disease. As disclosed in U.S. Pat. No. 7,214,524 to Reddy et al., hereby incorporated by reference, Marek's disease (MD) is believed to be a highly prevalent and important lymphoproliferative disease of chickens. Control of in commercial chickens has been attempted by using live virus vaccines consisting of attenuated or naturally avirulent MD-related herpesviruses. Although vaccination programs have been considered highly effective overall, the poultry industry continues to experience monetary losses due to MD. Given the tendency of MD virus to become more virulent with time, coupled with the economic pressures confronting the poultry industry, there is still a strong incentive to develop even more efficacious products that will protect better in the face of early challenge with very virulent field strains without causing adverse side effects. In one embodiment, the present invention contemplates at least one vaccine to protect a subject (i.e., for example, a chicken) against MD comprising superior protection and improved safety as compared to certain existing commercial vaccines.

Several serotypes of MD virus have been found in chickens: (1) serotype 1, the oncogenic form responsible for the disease, including high- and low-virulence MD virus and their attenuated variants; (2) serotype 2, a nononcogenic MD virus; and (3) serotype 3, herpesvirus of turkeys (HVT). The prototype MD vaccine comprises the serotype 3 virus originally isolated from turkeys as disclosed in Witter et al., Am. J. Vet. Res. 31, 525-538 (1970) and U.S. Pat. No. 3,642,574 to Okazaki et al., both of which are hereby incorporated by reference. HVT lacks oncogenicity, is a self-limiting infection, has good replication in vivo and in vitro, is available as a cell-free and/or cell-associated preparations, and has high protective efficacy. A commonly used strain of HVT is FC126.

Vaccines produced from the naturally avirulent SB-1 strain as disclosed in Schat et al., J. Natl. Cancer Inst. 60, 1075-1082 (1978) and U.S. Pat. No. 4,160,024 to Schat et al., both of which are hereby incorporated by reference, have been available in the United States since 1984. The SB-1 strain is poorly protective against the highly virulent MDV strains. SB-1 vaccines are usually used in combination with HVT as a bivalent vaccine since it has been reported that the two viruses together produce greater protection than does either one alone as disclosed in Schat et al., Avian Pathol. 11, 593-606 (1982) and Witter, Avian Pathol. 11, 49-62 (1982), both of which are incorporated in their entirety by reference. This phenomenon has been termed "protective synergism". The SB-1+HVT bivalent vaccine represents about 18% of the United States market for MD vaccines at present and is considered to be among the most efficacious of the various MD products available. However, sporadic losses occur despite its use.

Another MD vaccine produced from strain CVI988 clone C (CVI988/C) has been licensed for commercial use in the United States. This vaccine was derived from a mildly virulent serotype 1 MD virus attenuated by serial passage in tissue culture as disclosed by deBoer et al. Avian Dis. 30, 276-283 (1986), hereby incorporated by reference. Another derivative of CVI988/C, identified as CVI988/C/R6, has further been described by de Boer et al., Advances in Marek's Disease Research, pp. 405-413 (1988), incorporated in its entirety by reference. More recently, the original low-passage strain, designated CVI988/Rispens, which has been in commercial use in other countries for a number of years, was found to be highly effective against challenge with several very virulent MD virus strains by Witter et al., The Fourth International Symposium on Marek's Disease, pp. 315-319 (1992), incorporated in its entirety by reference.

An experimental vaccine derived from Md11, a very virulent serotype 1 MD field isolate, was further reported by Witter et al., The Fourth International Symposium on Marek's Disease, pp. 315-319 (1992), incorporated in its entirety by reference. Md11 was attenuated by 75 serial passages in cell culture, and the resultant vaccine designated Md11/75C. This vaccine has been shown to provide good protection against challenge with Md5 and most other highly virulent MD viruses tested; but it was less efficacious against challenge with the JM/102W strain, a prototype MD virus effectively protected against by HVT and SB-1 vaccines. Furthermore, its efficacy was consistently lower in chicks with HVT antibody.

As disclosed in U.S. Pat. No. 4,895,717 to Witter et al., incorporated herein by reference, a revertant-derivative of Md11/75C, referred to as Md11/75C/R2, was shown to be superior to several other monovalent vaccines and was the equal of a bivalent (HVT+SB-1) vaccine as disclosed in Witter, Avian Dis. 31, 752-765 (1987), incorporated herein by reference However, the inherent pathogenicity of serotype 1 viruses and the potential of attenuated strains to revert to greater pathogenicity as provided for in Witter et al., Avian Pathol. 13, 75-92 (1984), incorporated in its entirety by reference, are factors to be considered in the licensing of such products. A clone derived from further passages of the Md11/75C/R2 strain, designated Md11/75C/R2/23 (or R2/23), was found by Witter et al., Avian Dis. 35, 877-891 (1991), hereby incorporated by reference, to possess the highly protective nature of the parent strain without its residual pathogenicity.

U.S. Pat. No. 4,895,718 to Witter et al., incorporated in its entirety by reference, describes an MD vaccine derived from 301B/1, a nonpathogenic serotype 2 field isolate. Strain 301B/1 possessed superior replicative ability to SB-1, as well as greater protectivity against challenge to viruses. Still other concerns have arisen over the use of some MD vaccines. As indicated, bivalent vaccines composed of MD virus serotypes 2 and 3 are currently widely used in the U.S. and have provided excellent protection against certain MD strains. However, use of such vaccines containing serotype 2 MD virus may lead to increased mortality from another disease, lymphoid leukosis. This enhancement of lymphoid leukosis in avian leukosis virus infected chickens resulting from vaccination with products containing serotype 2 MD virus has been an unfortunate deterrent to their expanded use.

Meq Protein Plays an Important Role in Lymphoid Organ Atrophy in Chickens.

We have earlier described the successful construction of overlapping cosmid clones from the very virulent Md5 strain of MDV (*Proc Natl Acad Sci USA* 99, 7054-70595). Using this technology we have generated a recombinant virus, rMd5ΔMeq, in which the meq gene was deleted (*Proc Natl Acad Sci USA* 101, 11815-11820). Pathogenesis experiments showed that the rMd5ΔMeq was fully attenuated, unable to transform T-lymphocytes and defective in latency in chickens. Since the rMd5ΔMeq virus was apathogenic in chickens, we evaluated its potential use as a vaccine after challenge with 648A, a highly pathogenic vv+ strain. Results showed that rMd5ΔMeq conferred 100% protection compared to 60% protection by commercial CVI988 vaccine (*Vaccine* 26, 1887-1892).

As Meq plays an important role in latency, we evaluated the effect of rMd5ΔMeq on lymphoid organ atrophy. Groups of 5 MDV maternal antibody negative $15I_5X7_1$ chickens were inoculated with 2000 pfu of rMd5, rMd5ΔMeq or CVI988. Five chickens served as negative controls. Thirteen days post infection, all chickens were euthanized and body, spleen, thymus and bursa weights measured and the lymphoid organ to body weight ratios were calculated. As suspected, rMd5ΔMeq infection resulted in increased spleen/body weight ratio and decreased bursa/body and thymus/body weight ratio (FIG. 1). This splenomegaly and atrophy of thymus and bursa may have a detrimental effect on commercial use of this candidate vaccine because it may negatively impact the ability of the chickens to respond immunologically to other pathogens or vaccines. On the other hand, CVI988 had very little effect on lymphoid organ/body weight ratios probably because it was able to enter into latency more readily and/or had a defect in replication gene/s preventing robust early cytolytic infection. Without intending to be limited in any way to any particular mechanism, these results indicate that Meq plays an important role in latency, and absence of Meq in vaccine candidates may negatively affect lymphoid organ atrophy due to its role in latency.

Generation of Mutant rMd5-CVI-LMeq and rMd5-CVI-Meq Viruses.

Since Meq plays an important role in T-cell transformation and latency, we examined the role of Meq of CVI988 vaccine in the context of the very virulent rMd5 strain.

Figure 2:
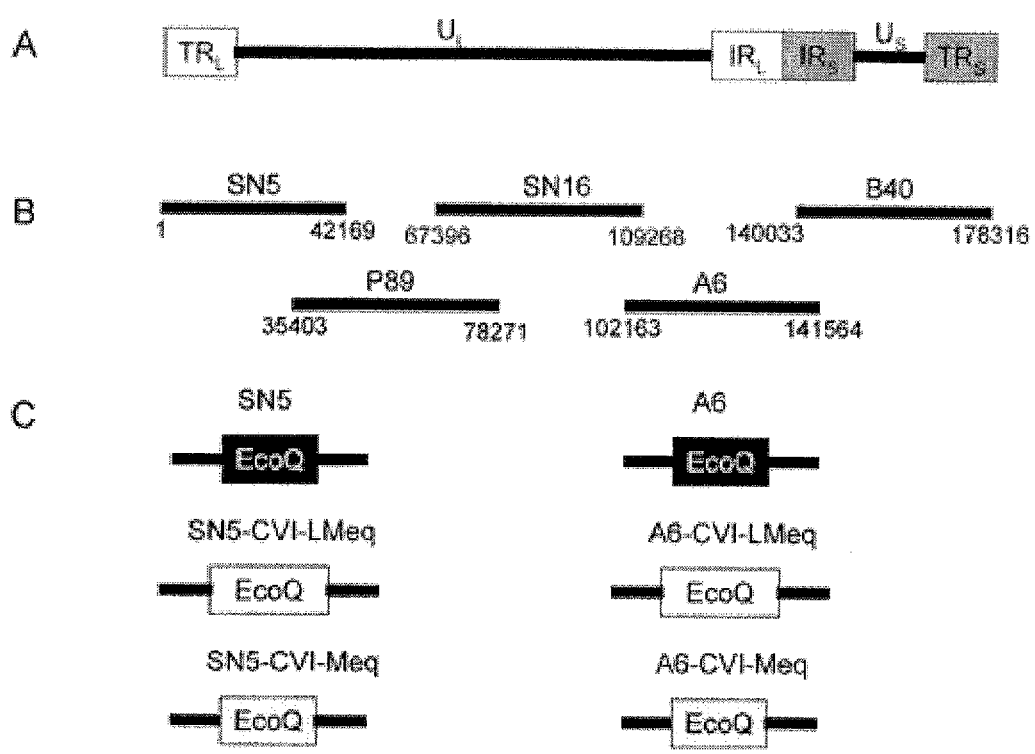
FIG. 2 shows the genomic organization of serotype 1 MDV genome. (A) The MDV genome consists of a unique long (UL) region flanked by inverted repeats, terminal repeat long (TRL), internal repeat long (IRL), and a unique short region (US) also flanked by inverted repeats, internal repeat short (IRS) and terminal repeat short (TRS). (B) Schematic representation of the overlapping cosmid clones generated to reconstitute an infectious virus from a very virulent (vv) strain of MDV (Md5). The positions of the cosmids are. (C) Location of EcoQ fragments are shown in SN5 and A6, which were used to generate SN5-CVI-LMeq, SN5-CVI-Meq, AC-CVI-LMeq and A6-CVI-Meq.
Figure 3:
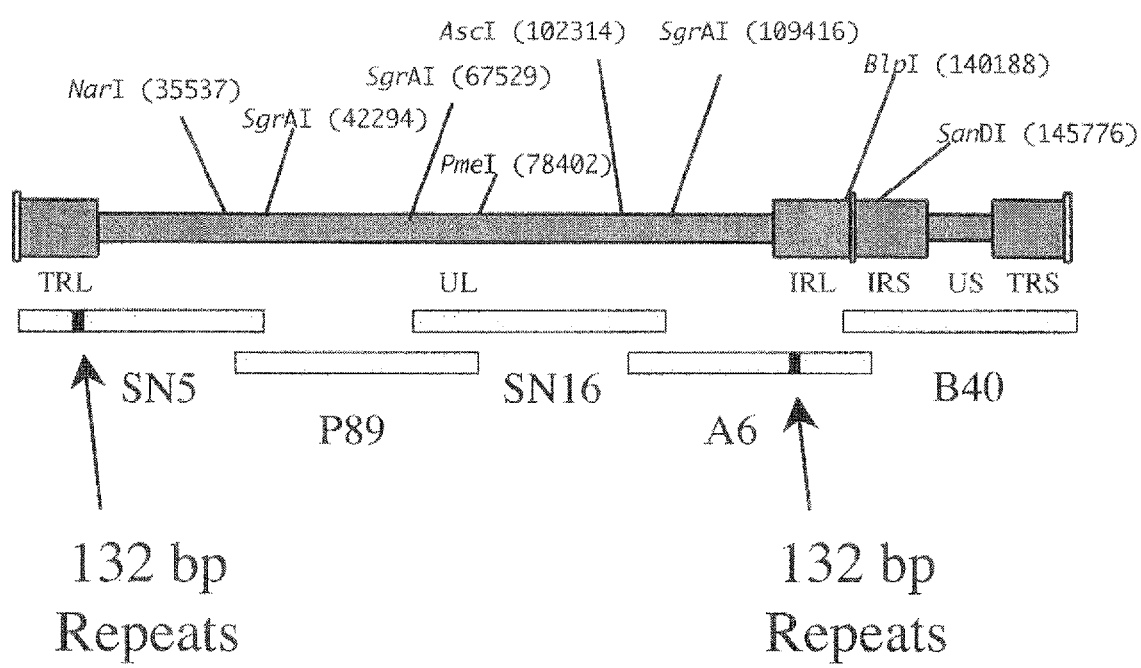
FIG. 3 shows overlapping cosmid clones of Md5. The MDV-1 viruses contain two copies of a 132-bp repeat, located in two separate parts of the genome. One pair of repeats is in the terminal repeat region (TRL) adjacent to the unique long region (UL). The other pair of repeats is inverted and located in the internal repeat (IRL) at the other end of the UL. The five overlapping cosmid clones are shown below the MDV genome and are aligned with the regions of the MDV genome from which they were cloned. The small bar in SN5 and A6 represents the location of the 132-bp repeats in these cosmids and their corresponding location in the TRL and IRL.
Figure 4:
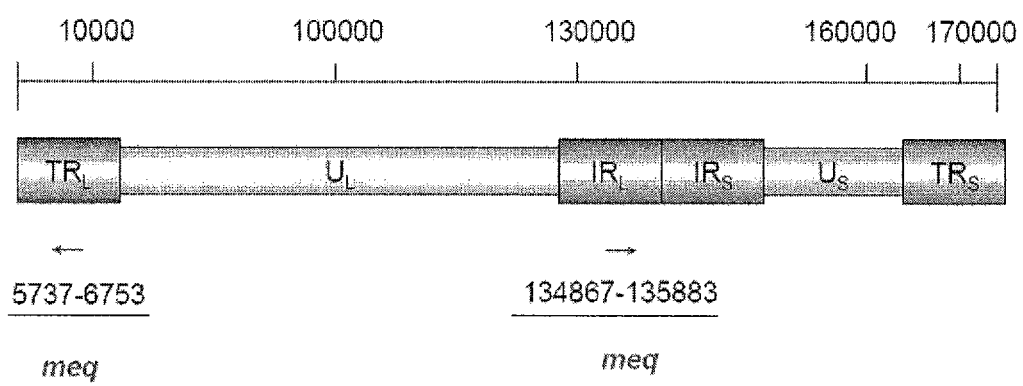
FIG. 4 shows the genomic organization of the Marek's disease virus (MDV), consisting of a unique long region ($U_L$) flanked by terminal and internal repeat long regions ($TR_L$ and $IR_L$, respectively) and a unique short region ($U_S$) flanked by internal and terminal repeat regions ($IR_S$ and $TR_S$, respectively). The meq gene is located within the $TR_L$ and $IR_L$ regions, i.e. the gene is present in two copies in the MDV genome.
Figure 13:
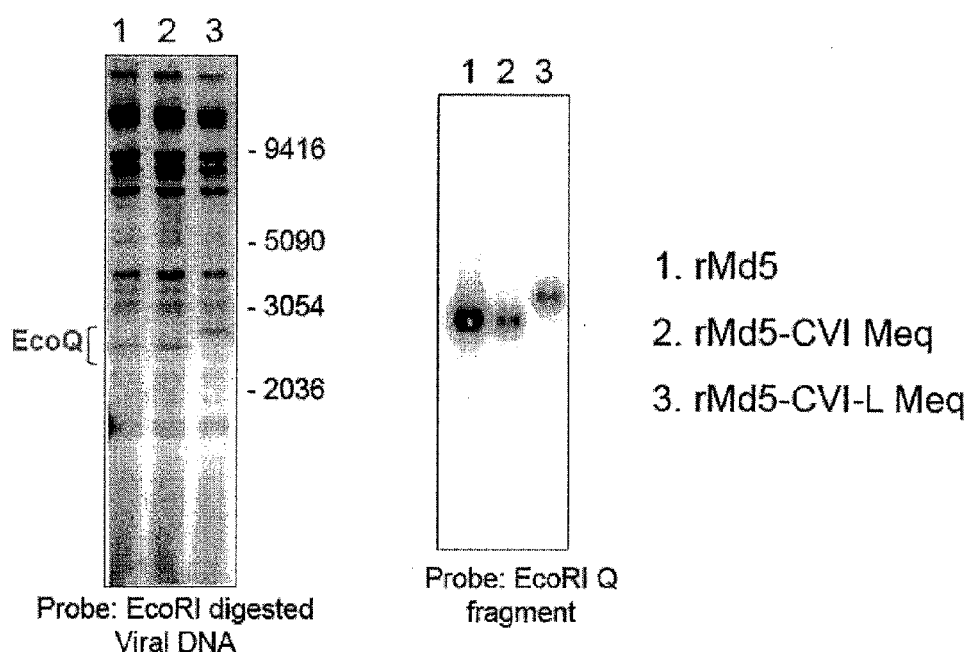
FIG. 13 shows a Southern blot analysis of rMd5, rMd5-CVI Meq and rMd5-CVI-L Meq genomic DNA. Dna from rMd5, rMd5-CVI Meq and rMd5-CVI-L Meq infected DEF was isolated by proteinase K digestion followed by phenol-chloroform extraction and ethanol precipitation. Three micrograms of each DNA sample was digested with EcoRI, separated on a 1% agarose gel, and transferred to nylon membranes. $^{32}$P-dCTP-labeled probes representing the complete MDV genome (cosmids SN5, P89, SN16, A6 and B40) or EcoQ fragment (2,456-bp fragment) were generated by random priming using high prime DNA labeling kit (Roche, Mannheim, Germany) and were used to hybridize to viral DNA, using standard protocols. Left panel: DNA was digested with EcoRI and probed with total viral MDV DNA. The restriction profile of rMd5-CVI Meq and rMd5-CVI-L Meq is similar to rMd5, indicating no gross genome rearrangements incurred. The only exception is the presence of a larger EcoQ fragment in rMd5-CVI-L Meq due to the insertion in the CVI-L gene. Right panel: viral DNA was digested with EcoRI and probed with EcoQ fragment DNA. Hybridization with the EcoQ probe demonstrates the equal size of the EcoQ fragment for rMd5 and rMd5-CVI Meq and the larger size fragment for rMd5-CVI-L Meq.
Figure 18:
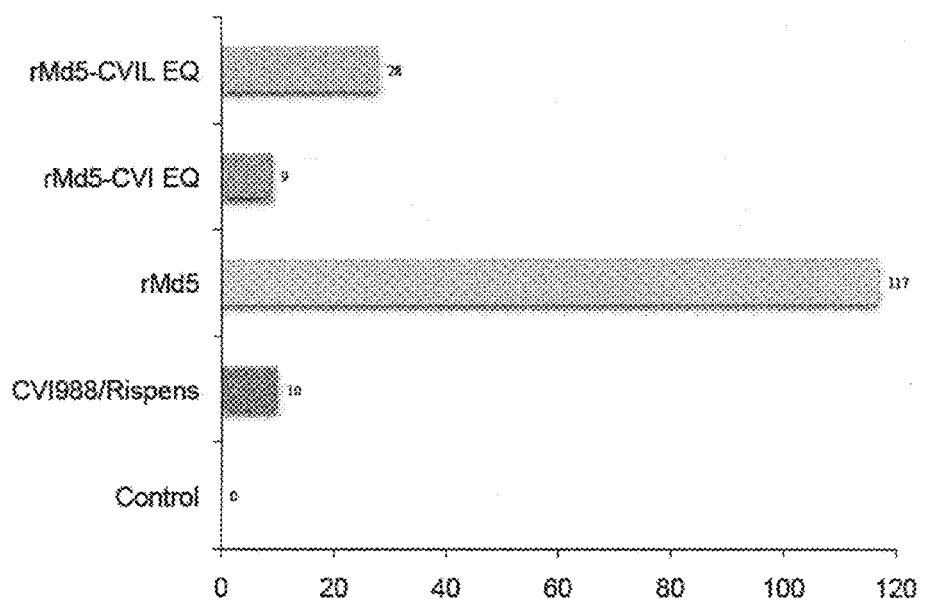
FIG. 18 shows the re-activation of recombinant rMDV viruses from peripheral blood lymphocytes from infected chickens. Buffy coats were collected obtained from heparinized blood by centrifugation at 500×g at 38 days post-injection (PI). Duck embryonic fibroblasts (DEF) monolayers were seeded in 35 mm plates and inoculated with $10^6$ lymphocytes in duplicate and viral plaques counted 7 days post inoculation. Significant differences were observed in the level of virus reactivation between rMd5 and rMd5-CVI Meq, rMd5-CVI-L Meq and CVI988/Rispens suggesting that the CVI Meq proteins play a role in virus reactivation.
Figure 20:
FIG. 20 shows the protection efficacy of rMd5-CVI Meq, rMd5-CVI-L Meq viruses in maternal antibody positive chickens. To study the protection efficacy of rMd5-CVI Meq, rMd5-CVI-L Meq in the laboratory setting, 17 day-old maternal antibody positive $15I_5 \times 7_1$ chicks were vaccinated with 2000 plaque forming units (pfu) of rMd5-CVI Meq, rMd5-CVI-L Meq or CVI/988/Rispens vaccine virus by the subcutaneous route. Five days later, groups of vaccinated and unvaccinated control chickens were challenged by subcutaneous inoculation with 500 PFU of the very virulent plus 648A MDV. Mortality during the course of the experiment was recorded and chickens were examined for gross MD lesions. At about 56 days post-challenge, all surviving chickens were euthanized and examined for gross MD lesions.

Using overlapping cosmid clones, we generated two mutant viruses in which the Md5 EcoQ fragment, which contains the meq gene, was replaced with the EcoQ fragments containing the Lmeq or meq genes encoded by the vaccine strain of CVI988 strain (FIG. 2). Briefly, the EcoQ fragment spanning the meq gene was deleted from cosmids, SN5 and A6 using the RecA-assisted restriction endonuclease cleavage method (RARE) to generate SN5ΔEcoQ and A6ΔEcoQ. The SN5-CVI-LMeq, SN5-CVI-Meq cosmids were generated by inserting the EcoQ fragments containing CVI-LMeq or CVI-Meq into SN5ΔEcoQ. Similarly, A6-CVI-LMeq, A6-CVI-Meq were generated by inserting the EcoQ fragments containing CVI-LMeq or CVI-Meq into A6ΔEcoQ. rMd5-CVI-LMeq was generated by transfecting SN5-CVI-LMeq and A6-CVI-LMeq and parental P89, SN16, and B40 cosmid DNA fragments into DEF cells by the calcium phosphate method. Similarly, rMd5-CVI-Meq was generated by transfecting SN5-CVI-Meq and A6-CVI-Meq and parental P89, SN16, and B40 DNA fragment clones. Plaques from recombinant viruses were evident 10-11 days post-transfection. The recombinant viruses were examined by Southern blot analysis (FIG. 13) to confirm that no major rearrangements had occurred during the recombination process and by indirect immunofluorescence assay (IFA) to confirm the expression of Meq.

Biological Characterization of rMd5-CVI-LMeq and rMd5-CVI-Meq.

Figure 10:
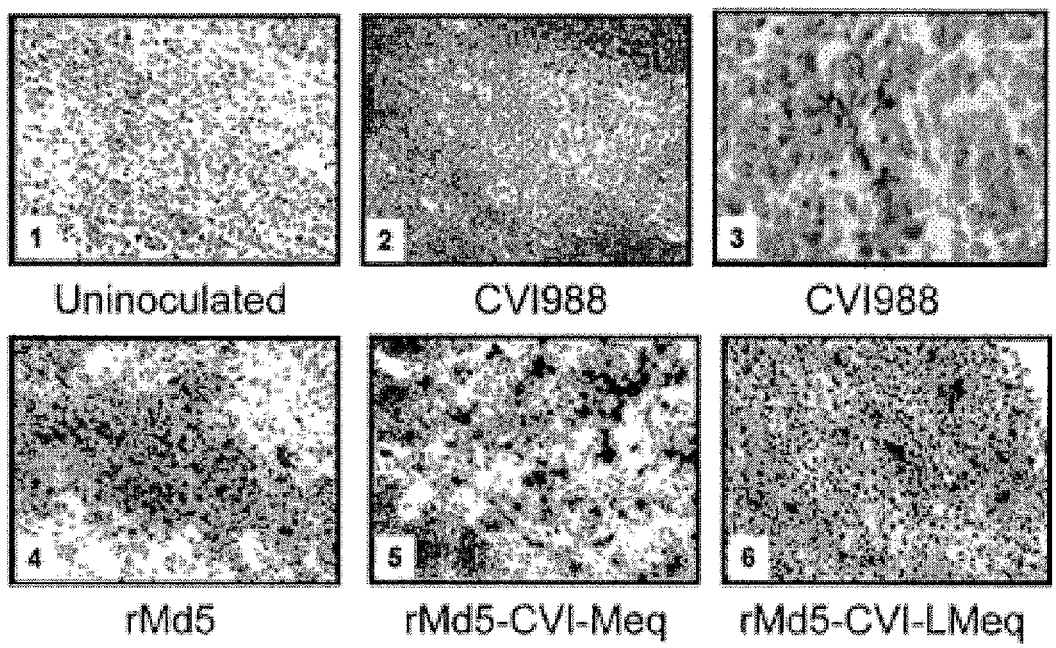
FIG. 10 shows an immunohistochemical analysis of lymphoid organs (6 days post-inoculation) of rMd5, CVI988, rMd5-CVI-LMeq, rMd5-CVI-Meq and control chickens. Frozen sections were stained with pp 38 specific monoclonal antibody except for panels 2 and 3 in which gB monoclonal antibody was used. There is comparable level of antigen expression in rMd5, rMd5-CVI-LMeq, rMd5-CVI-Meq infected chickens, while antigen expression in CVI988 is significantly reduced (panel 2 and panel 3, higher magnification), suggesting that early cytolytic infection is defective.
Figure 11:
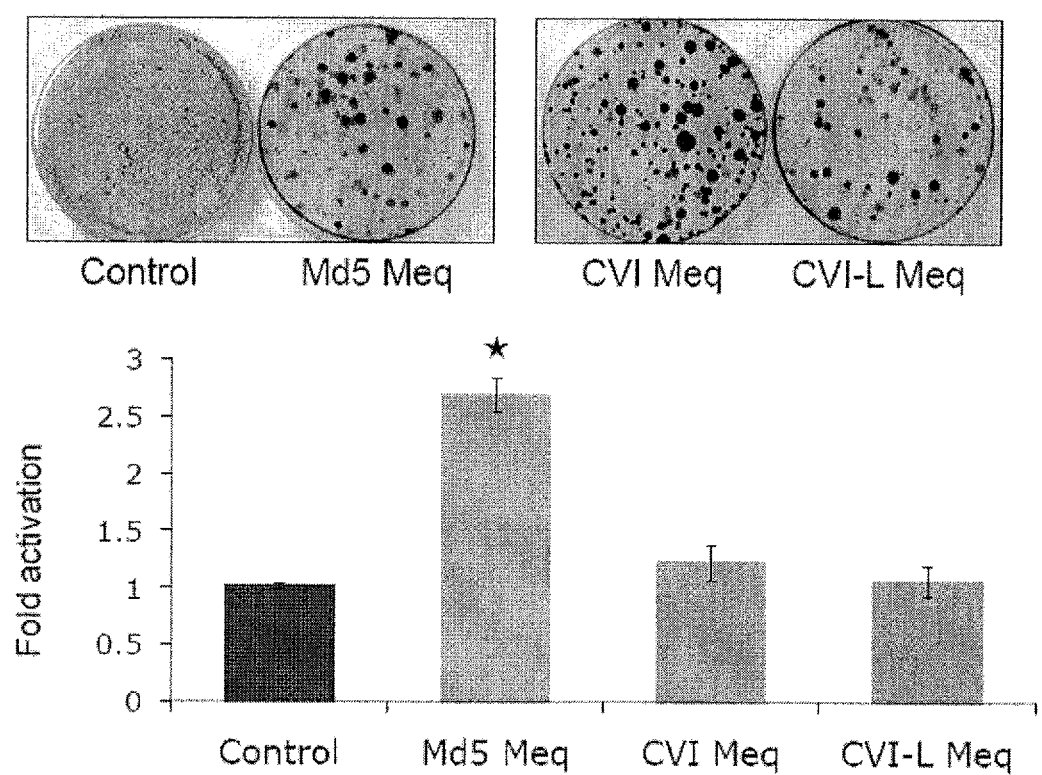
FIG. 11 shows a graph representing the in vitro characterization of the transforming and transactivating activities of the Meq protein of the very virulent strain of MDV, Md5, and vaccine strain, CVI988/Rispens. The Meq genes of Md5 (Md5 meq) and CVI988 (CVI meq and CVI-L meq) were cloned into a replicating defective murine retrovirus vector (pBABE) and their transformation activity evaluated in Rat-2 and NIH3T3 (top panel) fibroblast cell lines by focus formation assay. As seen, all three Meq proteins were able to transform foci when compared to the control empty pBABE vector. The visualization of transformed foci was carried out by crystal violet staining. The transactivation activity of Md5 and CVI Meq proteins on their own promoter, Md5 meq, CVI meq and CVI-L meq genes were cloned into the mammalian expression vector pCDNA 3.1 under the control of the CVM promoter. Expression plasmids were co-transfected with a luciferase reporter vector containing the meq promoter into DF-1 cells (an immortalized chicken fibroblast cell line). 24 h post-transfection luciferase activity in the transfected cells was determined using a luminometer and results were normalized based on total protein content with a value of 1 given to the control transfection lacking a meq gene. As seen in the lower panel, only Md5 Meq was able to transactivate its own promoter.

To determine whether expression of Meq from CVI988 vaccine strain had any effect on in vitro growth replication, the growth rate of rMd5-CVI-LMeq and rMd5-CVI-Meq viruses were compared with that of rMd5 by multi-step growth kinetics. Our results show that the growth characteristics of these viruses was similar indicating that expression of Meq from vaccine strain in pathogenic MDV did not alter its in vitro growth properties. Characterization of the role of Meq in in vivo replication, was carried out by inoculating MDV maternal antibody-negative, chickens with rMd5, rMd5-CVI-LMeq, rMd5-CVI-Meq or CVI988 viruses at day of age. At day 6 post-inoculation, 3 chickens from each group were euthanized and lymphoid organs (thymus, bursa of Fabricius and spleen) were collected and examined for viral antigen expression (pp 38 or gB) by immunohistochemistry. No difference in the expression of pp 38 protein in the lymphoid organs of rMd5, rMd5-CVI-LMeq or rMd5-CVI-Meq-inoculated chickens was observed, indicating that expression of Meq proteins from CVI988 vaccine strain in the background of pathogenic rMd5, did not affect early cytolytic infection in lymphocytes (FIG. 10).

To compare the pathogenic properties of rMd5, rMd5-CVI-LMeq and rMd5-CVI-Meq, 10-17 1-day-old MDV maternal antibody-negative chickens were inoculated with 2,000 pfu of viruses or mock infected and raised in isolation for 8 weeks. All the rMd5 inoculated chickens either had MD specific lesions or succumbed prior to the development of MD specific lesions, whereas only 2 chicken inoculated with rMd5-CVI-LMeq or rMd5-CVI-Meq, had MD specific gross nerve lesions at termination (FIG. 6). Comparison of mortality rates showed that none of the chickens inoculated with rMd5-CVI-LMeq or rMd5-CVI-Meq died during the 8-week long experiment, however all rMd5 inoculated chickens died between 3-5 weeks post infection. We also conducted the same experiment in antibody-positive chickens, which are moderately resistant. All the rMd5 inoculated chickens had MD specific lesions but none of the chickens inoculated with rMd5-CVI-LMeq or rMd5-CVI-Meq had any MD lesions (FIG. 6). While not intending in any manner to limit the invention to any particular mechanism, these results indicate that Meq from vaccine strain CVI988 is responsible for attenuation; however, virus replication during early cytolytic infection in lymphocytes and transmission through the feather follicular epithelium is not affected when compared to rMd5.

Since the recombinant viruses with meq gene from vaccine strains (rMd5-CVI-LMeq and rMd5-CVI-Meq) did not induce any MD lesions in MDV maternal antibody positive chickens, we tested their potential to protect against challenge with a highly virulent vv+ field strain, 648A. Protection experiments were conducted in MDV maternal antibody-positive chickens, to mimic field challenge conditions. Groups of 17 chickens were vaccinated with 2000 pfu of rMd5-CVI-LMeq, rMd5-CVI-Meq or commercial vaccine CVI988 strain at 1-day of age. Five days later (day 6 of age), the chickens were challenged with 648A a vv+ MDV strain and raised in isolation for 8 weeks. All the chickens that died during the experiment or at the termination were examined for MD specific lesions. Both rMd5-CVI-LMeq and rMd5-CVI-Meq viruses conferred 100% protection while the commercial CVI988 vaccine only protected 64% (5/17 and 7/17)

of the challenged chickens (FIG. 7). Taken together these results indicate that meq from CVI988 vaccine virus could be utilized to generate the next generation of recombinant MDV vaccines that could protect from highly virulent vv+ field strains.

Generation of a Meq Revertant rMd5-CVI-LMeq-R Virus.

In order to confirm that the attenuated phenotype of rMd5-CVI-LMeq virus was due to CVI-Meq, and not due to unforeseen mutations, we generated a revertant virus (rMd5-CVI-LMeq-R) in which the parental Md5 meq gene was restored. rMd5-CVI-LMeq-R was generated by co-transfection of viral DNA isolated from rMd5-CVI-LMeq virus along with Md5 EcoQ genomic DNA fragment into CEF. Individual viral plaques were isolated and the presence of meq revertant viruses (rMd5-CVI-LMeq-R) identified by PCR (based on PCR fragment size). The pathogenicity of rMd5-CVI-LMeq-R was fully restored to that of parental virus. This data confirms that expression of CVI-Meq protein is responsible for attenuated phenotype observed in the recombinant viruses.

Genomic Sequences of Cosmid Clones Used to Generate Recombinant Viruses.

We have determined the complete genomic sequence of cosmid clones, SN5 (42,159 bp), P89 (42,859 bp), SN16 (41,869 bp), A6 (39,159 bp) and B40 (38,293 bp). The EcoQ region spanning the CVI-LMeq (2,637 bp) and CVI-Meq (2,460 bp), which were used to generate rMd5-CVI-LMeq and rMd5-CVI-Meq viruses, were also sequenced. The total genome lengths were as follows: rMd5 (178,316 bp), rMd5-CVI-LMeq (178,498 bp) and rMd5-CVI-Meq (178,321 bp) (FIG. 8) while the parental (wild-type) sequence of Md5 earlier published was shown to be 177,874 bp (Tulman, E. R., Afonso, C. L., Lu, Z., Zsak, L., Rock, D. L., and Kutish, G. F. (2000) The genome of a very virulent Marek's disease virus, J Virol 74, 7980-7988.)

Figure 5:
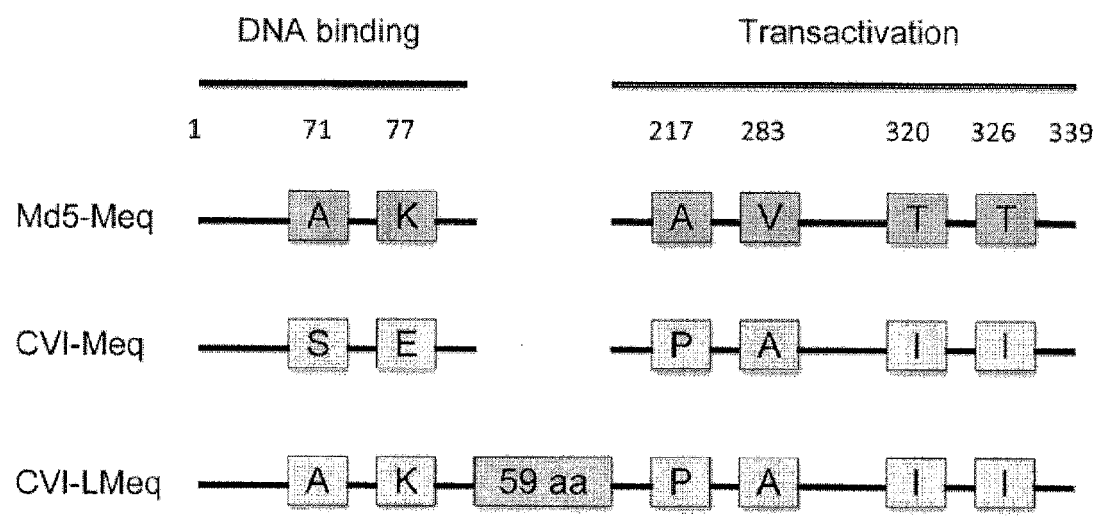
FIG. 5 shows the structure of the Meq proteins of Md5 and CVI988/Rispens strains. Meq contains an amino-terminal DNA binding domain and a carboxy-terminal transactivation domain. CVI-Meq proteins have 2 amino acid differences in the DNA binding domain and 4 amino acids differences in the transactivation domain when compared to Md5-Meq. As noted above, the present invention contemplates in one embodiment, mutated nucleic acid encodes an Meq CVI/Md5 protein mutant having point mutations selected from the group comprising A71S and K77E. In addition, CVI-LMeq has a 59 amino acid insertion that is rich in proline.

The only difference observed at the protein level between the published Md5 sequence and that from the cosmids was restricted to the large tegument protein (UL36). There was a deletion of 18 bp, which resulted in the loss of 6 amino acids in the repeat region at the carboxy-half of the protein. As expected, CVI-LMeq and CVI-Meq presented 6 amino acid differences compared to oncogenic Md5-Meq at positions 71, 77, 217, 283, 320 and 326. In addition, CVI-LMeq had an extra 59 amino acid repeat region in the transactivation domain (FIG. 5).

At the nucleotide level the majority of the differences were observed in the number of repeat regions in the "a" like sequence found at the termini of both TRL and TRS, and junction between IRL and IRS (FIG. 8). In addition, thirteen single nucleotide insertions or deletions were observed in the non-coding regions. Interestingly, the A6 cosmid spanned from 102,163-141,564, and the overlap between the B40 and A6 cosmid was only 1,288 bp, instead of the 5,588 bp reported earlier (Reddy, S. M., Lupiani, B., Gimeno, I. M., Silva, R. F., Lee, L. F., and Witter, R. L. (2002) Rescue of a pathogenic Marek's disease virus with overlapping cosmid DNAs: use of a pp 38 mutant to validate the technology for the study of gene function, Proc Natl Acad Sci USA 99, 7054-7059.).

Pharmaceutical Formulations

In some embodiments, the present invention contemplates a composition comprising an Meq MDV vaccine and a pharmaceutical formulation. In one embodiment, the formulation comprises a cell-associated virus preparation. In one embodiment, the cell-associated preparation further comprises dimethylsufoxide. In one embodiment, the cell-associated formulation is frozen, for example, by liquid nitrogen. In one embodiment, the formulation comprises a cell-free virus preparation. In one embodiment, the cell-free preparation is lyophilized. In one embodiment, the composition is administered by routes including, but not limited to, subcutaneous injection, and/or intramuscular injection. In one embodiment, the vaccine is administered to chicks, wherein the chicks are between 0.5-2 days old. Preferably, the vaccine in administered in chicks 1 day old. Alternatively, the vaccine may be administered in ovo on or about Day 18 of embryonation.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155).

In a preferred embodiment, the active compound and optionally another therapeutic or prophylactic agent are formulated in accordance with routine procedures as pharmaceutical compositions adapted for intravenous administration to human beings. Typically, the active compounds for intravenous administration are solutions in sterile isotonic aqueous buffer. Where necessary, the compositions can also include a solubilizing agent. Compositions for intravenous administration can optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the active compound is to be administered by infusion, it can be dispensed, for example, with an infusion bottle containing sterile pharmaceutical grade water or saline. Where the active compound is administered by injection, an ampoule of sterile water for injection or saline can be provided so that the ingredients can be mixed prior to administration.

Compositions for oral delivery can be in the form of tablets, lozenges, aqueous or oily suspensions, granules, powders, emulsions, capsules, syrups, or elixirs, for example. Orally administered compositions can contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for an orally administered of the active compound. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate can also be used. Oral compositions can include standard vehicles such as mannitol, lactose, starch, magnesium stearate, sodium saccharine, cellulose, magnesium carbonate, and the like. Such vehicles are preferably of pharmaceutical grade.

Further, the effect of the active compound can be delayed or prolonged by proper formulation. For example, a slowly soluble pellet of the active compound can be prepared and incorporated in a tablet or capsule. The technique can be improved by making pellets of several different dissolution rates and filling capsules with a mixture of the pellets. Tablets or capsules can be coated with a film that resists dissolution for a predictable period of time. Even the parenteral preparations can be made long acting, by dissolving or suspending the compound in oily or emulsified vehicles, which allow it to disperse only slowly in the serum.

Compositions for use in accordance with the present invention can be formulated in conventional manner using one or more physiologically acceptable carriers or excipients.

Thus, the compound and optionally another therapeutic or prophylactic agent and their physiologically acceptable salts and solvates can be formulated into pharmaceutical compositions for administration by inhalation or insufflation (either through the mouth or the nose) or oral, parenteral or mucosol (such as buccal, vaginal, rectal, sublingual) administration. In some embodiments, the administration is optical (e.g. eyes drops applied directly to the eye). In one embodiment, local or systemic parenteral administration is used.

For oral administration, the compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active compound.

For buccal administration the compositions can take the form of tablets or lozenges formulated in conventional manner.

For administration by inhalation, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the compound and a suitable powder base such as lactose or starch.

The compositions can be formulated for parenteral administration by injection, e.g., by bolus injection or continuous infusion. Formulations for injection can be presented in unit dosage form, e.g., in ampoules or in multi-dose containers, with an added preservative. The pharmaceutical compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

In addition to the formulations described previously, the compositions can also be formulated as a depot preparation. Such long acting formulations can be administered by implantation (for example subcutaneously or intramuscularly) or by intramuscular injection. Thus, for example, the pharmaceutical compositions can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can for example comprise metal or plastic foil, such as a blister pack. The pack or dispenser device can be accompanied by instructions for administration.

In certain preferred embodiments, the pack or dispenser contains one or more unit dosage forms containing no more than the recommended dosage formulation as determined in the Physician's Desk Reference ($62^{nd}$ ed. 2008, herein incorporated by reference in its entirety).

Methods of administering the active compound and optionally another therapeutic or prophylactic agent include, but are not limited to, parenteral administration (e.g., intradermal, intramuscular, intraperitoneal, intravenous and subcutaneous), epidural, and mucosal (e.g., intranasal, rectal, vaginal, sublingual, buccal or oral routes). In a specific embodiment, the active compound and optionally another prophylactic or therapeutic agents are administered intramuscularly, intravenously, or subcutaneously. The active compound and optionally another prophylactic or therapeutic agent can also be administered by infusion or bolus injection and can be administered together with other biologically active agents. Administration can be local or systemic. The active compound and optionally the prophylactic or therapeutic agent and their physiologically acceptable salts and solvates can also be administered by inhalation or insufflation (either through the mouth or the nose). In a preferred embodiment, local or systemic parenteral administration is used.

In specific embodiments, it can be desirable to administer the active compound locally to the area in need of treatment. This can be achieved, for example, and not by way of limitation, by local infusion during surgery or topical application, e.g., in conjunction with a wound dressing after surgery, by injection, by means of a catheter, by means of a suppository, or by means of an implant, said implant being of a porous, non-porous, or gelatinous material, including membranes, such as silastic membranes, or fibers. In one embodiment, administration can be by direct injection at the site (or former site) of an atherosclerotic plaque tissue.

Pulmonary administration can also be employed, e.g., by use of an inhaler or nebulizer, and formulation with an aerosolizing agent, or via perfusion in a fluorocarbon or synthetic pulmonary surfactant. In certain embodiments, the active compound can be formulated as a suppository, with traditional binders and vehicles such as triglycerides.

The amount of the active compound that is effective in the treatment or prevention of macular degeneration or angiogenesis can be determined by standard research techniques. For example, the dosage of the active compound which are effective in the treatment or prevention of age-related macular degeneration can be determined by administering the active compound to an animal in a model such as, e.g., the animal models known to those skilled in the art. In addition, in vitro assays can optionally be employed to help identify optimal dosage ranges.

Selection of a particular effective dose can be determined (e.g., via clinical trials) by a skilled artisan based upon the consideration of several factors, which are known to one skilled in the art. Such factors include the disease to be treated or prevented, the symptoms involved, the subject's body mass, the subject's immune status and other factors known by the skilled artisan.

The dose of the active compound to be administered to a subject, such as a human, is rather widely variable and can be subject to independent judgment. It is often practical to administer the daily dose of the active compound at various hours of the day. However, in any given case, the amount of the active compound administered will depend on such factors as the solubility of the active component, the formulation used, subject condition (such as weight), and/or the route of administration.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl; (microliters); cm (centimeters); mm (millimeters); μm (micrometers); nm (nanometers); C (degrees Centigrade); miR or miRNA (microRNA); BSA (bovine serum albumin); BCS (bovine calf serum); DEF (duck embryo fibroblasts); PCR (polymerase chain reaction).

Example I

Construction of Attenuated MPV Meq Vaccines

Methods and Materials
Cells and Viruses.

Primary duck embryonic fibroblasts (DEF) were used for virus propagation, virus reactivation assay, growth curves and DNA transfections. Recombinant viruses were generated from cosmids derived from a very virulent MDV strain, Md5. DEF and CEF were maintained in Leibowitz-McCoy (LM) media supplemented with 5% bovine calf serum (BCS) and penicillin-streptomycin at 37° C.
Cosmids.

As described in Lupiani et al., *Proceedings of the National Academy of Sciences USA* 101, 11815-11820 (2004), incorporated herein by reference, SN5, P89, SN16, A6 and B40 cosmids encompass the entire genome of the very virulent strain Md5 and were used to generate a recombinant Md5 (rMd5) virus and recombinant Md5 viruses with mutations in phosphorylation sites, basic region, leucine zipper region and transactivation domains of the Meq protein as shown in FIG. 5.

The EcoQ fragment was released from previously described cosmids A6 and SN5 using recA assisted restriction endonuclease (RARE) method. Briefly, recA and primers SR1116 (5'-GAA TCG GAT TTG GAA TAA CCG AAT TCG GTG ATA TAA AGA C-3') (SEQ ID NO: 1) and SR1117 (5'-GAC ATT ACA AGA ATA GTT TGA ATT CTC GGG ATA ATC TCC C-3') (SEQ ID NO: 2) were used to protect the flanking EcoRI sites of the EcoQ fragment during the EcoRI methylation reaction. The unmethylated EcoRI sites were digested with EcoRI releasing the EcoQ fragment, which was subsequently cloned into pCR2.1 (Invitrogen, Carlsbad, Calif.). The digested A6 and SN5 cosmids were self-ligated generating A6ΔEcoQ and SN5ΔEcoQ and HB101 competent bacteria transduced using Gigapack III (Stratagene, La Jolla, Calif.) according to manufacturer's recommendations.

To generate Md5-CVI chimeric Meq proteins, two forms of the EcoQ fragments from CVI988 called EcoQ-CVIL, and EcoQ-CVI were cloned into pLIT29 (NEB). Meq CVI/Md5 mutant (A71S, and K77E) was generated by cloning the EcoRI/KpnI fragment (nucleotides 134515-135251) from EcoQ-CVI into the corresponding region of the Md5-EcoQ clone. Meq Md5/CVI (A217P, V283A, T320I and T326I) and Md5-CVIL (194-253 Insertion, A217P, V283A, T320I and T326I) mutants were generated by transferring the KpnI/EcoRI fragment (nucleotides 135251-136972) of EcoQ-CVI and EcoQ-CVIL into the corresponding region of the Md5-EcoQ plasmid, respectively.

To generate recombinant Md5 viruses with point mutations in the DNA binding domain of Meq: A71S, A71S, A71D and R72P, standard site directed mutagenesis was carried out using the EcoQ-Md5 fragment as template and the presence of the mutations confirmed by sequence analysis.

To generate phosphorylation mutant viruses, site directed mutations were introduced into the phosphorylations sites found at position 28, 42 and 79 in the Meq gene of Md5: T28A, S42A, S42D and T79A, and the presence of the mutations confirmed by sequence analysis.

To generate a recombinant Md5 virus in which the leucine zipper of Meq-Md5 was replaced with the leucine zipper found in the Fos gene, overlapping PCR, in a combination of three PCR reactions, was performed to replace the leucine zipper region of meq with the leucine zipper region of Fos. Two primary PCR reactions were performed to generate the 5' and 3' ends of meq-KpnI fragment. Both amplicons were gel purified, mixed together and used as templates in a third PCR reaction, generating a full meq-KpnI fragment containing the Fos leucine zipper in place of the meq leucine zipper (meq-Fos-KpnI). The meq-Fos-KpnI fragment was subsequently introduced into the EcoQ-Md5 fragment generating EcoQ-MF.

To generate recombinant Md5-Meq viruses, these mutant EcoQ fragments were introduced into cosmids A6ΔEcoQ and SN5ΔEcoQ using RARE. Briefly, the EcoRI site of cosmids A6ΔEcoQ and SN5ΔEcoQ was protected during the methylation reaction using recA and primer SR1130 (5'-GAA TCG GAT TTG GAA TAA CCG AAT TCT CGG GAT AAT CTC CCG ATG G-3') (SEQ ID NO: 3) then subjected to EcoRI restriction digestion to linearize the cosmids and subsequently ligated to the mutant EcoQ fragments. Following ligation and transduction, clones containing the mutant EcoQ fragments in the correct orientation were identified by PCR and selected positive colonies sequenced across the junction regions. The integrity of the mutant cosmids was confirmed by evaluation of restriction digestion pattern.
Transfections.

Parental and mutant cosmids DNA were digested with NotI, to release the viral insert, and purified by phenol chloroform extraction and ethanol precipitation before transfection. To generate rMd5 and rMd5-Meq-Mutants, 500 μg of cosmids P89, SN16, B40, SN5 and A6 or P89, SN16, B40, SN5-Mutant and A6-Muatnt, respectively, were used to transfect $1.2 \times 10^6$ DEF in 60 mm dishes by the calcium phosphate procedure. Five days after transfection, cells were trypsinized and seeded onto a 100 mm dish and monitored for cytopathic effects. Viral stocks of recovered viruses were subsequently made in DEF for further analysis.

The same procedure was used to generate the following recombinant viruses (rMd5-CVIL, rMd5-CVI, rMd5-CVI/Md5, rMd5-Md5/CVI, rMd5-MF, rMd5-MeqT29A, rMd5-MeqS42A, rMd5-MeqS42D, rMd5-MeqT79A, rMd5-MeqA71S, rMd5-MeqA71D, rMd5-MeqA71E/R72P) using the corresponding mutated cosmid clones.

Passaging Cells.

Early Adaptation of rMd5-CVI-LMeq and rMd-CVI-Meq Viruses in Fibroblasts.

We have shown that rMd5-CVI-LMeq and rMd5-CVI-Meq are non-pathogenic in MDV maternal antibody positive chickens but are mildly pathogenic in highly susceptible antibody negative chickens (FIG. 6 and FIG. 7). rMd5-CVI-Meq and rMd5-CVI-LMeq viruses are subjected to serial passage in CEF and DEF cells. rMd5-CVI-LMeq and rMd5-CVI-Meq viruses were able to establish robust cytolytic infection in the lymphoid organs. Likewise, the original CVI988 seed stock that was isolated in The Netherlands was able to induce mild lesion in commercial chickens that possibly had MDV maternal antibodies (Rispens, B. H., van Vloten, H., Mastenbroek, N., Maas, J. L., and Schat, K. A. (1972) Control of Marek's disease in the Netherlands. II. Field trials on vaccination with an avirulent strain (CVI 988) of Marek's disease virus, Avian Dis 16, 126-138.). This mildly virulent virus was adapted by serial cell culture passage in DEF prior to its use as an effective vaccine to control MD (Rispens, B. H., van Vloten, H., Mastenbroek, N., Maas, J. L., and Schat, K. A. (1972) Control of Marek's disease in the Netherlands. II. Field trials on vaccination with an avirulent strain (CVI 988) of Marek's disease virus, Avian Dis 16, 126-138. and Rispens, B. H., van Vloten, H., Mastenbroek, N., Maas, H. J., and Schat, K. A. (1972) Control of Marek's disease in the Netherlands. I. Isolation of an avirulent Marek's disease virus (strain CVI 988) and its use in laboratory vaccination trials, Avian Dis 16, 108-125.). We believe that during cell culture passage the original mildly virulent CVI988 may have accumulated mutations in gene/s responsible for replication in lymphcytes and thus may have lost its ability to cause lymphoid organ atrophy.

The adaptation of rMd5-CVI-LMeq and rMd5-CVI-Meq viruses are carried out by inoculating confluent monolayers of CEF and DEF cells in 150 mm tissue culture dishes at high multiplicity of infection for 40 rounds. Briefly, viral passage are carried out every 4-7 days post-inoculation when there is approximately 80% cytopathic effect in the monolayer. During early adaptation (1-15 passage level), we expect to pass 20% of the infected cells to infect fresh monolayers. It is our expectation that as the recombinant viruses are adapted to in vitro propagation, they replicate with faster kinetics. Thus during later passage level (16-40 passage level) we expect to use 2-5% of the infected cells to infect fresh monolayers. Viral stocks generated from both rMd5-CVI-Meq and rMd5-CVI-LMeq, in two cell types (DEF and CEF) are frozen in liquid nitrogen every fifth passage for 40 rounds.

We have generated 4 series of cell culture adapted viruses from rMd5CVI-LMeq and rMd5CVI-Meq prepared in CEF and DEF. A total of 9 viral stocks of rMd5-CVI-LMeq passed in CEF (rMd5CVI-LMeq-CP0, -CP5, -CP10, -CP15, CP20, -CP25, -CP30, -CP35 and -CP40); 9 viral stocks of rMd5-CVI-LMeq passed in DEF (rMd5-CVI-LMeq-DP0, -DP5, -DP15, -DP20, -DP25, -DP30, -DP35 and -DP40); 9 viral stocks of rMd5-CVI-Meq passed in CEF (rMd5-CVI-Meq-CP0, -CP5, -CP10-CP15, -CP20, -CP25, -CP30, -CP35 and -CP40); and 9 viral stocks of rMd5CVI-Meq passed in DEF (rMd5-CVI-Meq-DP0, -DP5, -DP10, -DP15, -DP20, -DP25, -DP30, -DP35 and -DP40). These 36 viral stocks have been tested for their in vitro growth properties and also tested for in vivo pathogenicity and replication in maternal antibody negative chickens.

Cloning of rMd5-CVI-Meq and rMd5-CVI-LMeq Passed in CEF and DEF.

Cloning of the cell culture adapted viruses is performed by isolating individual plaques using agar overlay method. Briefly, viruses to be cloned are plated in 60 mm dishes and once CPE is evident, media is removed and replaced with 0.6% agar in growth medium. After the agar solidifies, agar on top of each plaque are removed using a wide-bore pipette tip and trypsin added. Trypsin is neutralized with growth media and trypsinized plaques are added to a fresh cell monolayer in 35 mm dishes. The cloning procedure allows the isolation of genotypically distinct viruses from a heterogenous population. The cloning of the adapted series is performed at passage level when the majority of the quasispecies have achieved the attenuated phenotype that have resulted in loss of lymphoid organ atrophy but has retained high level of protection. Since the cloned viruses are genotypically distinct, it allows the identification of mutations (based on sequence comparison and by generation of chimeric viruses). The cloned viruses are also be subjected to in vitro and in vivo characterization to confirm the presence of desired phenotype.

Cloned viruses from attenuated viruses generated have the desired phenotype of no lymphoid organ atrophy and superior protection. It is our expectation that we have generated 4 clones each from rMd5-CVI-LMeq passed in CEF, rMd5-CVI-LMeq passed in DEF, rMd5-CVI-Meq passed in CEF, rMd5-CVI-Meq passed in DEF. These 16 cloned viruses are examined for the desired phenotype of loss of lymphoid organ atrophy and superior protection.

In Vitro Growth Properties of Cloned Viruses.

In vitro characterization of the passaged and cloned viruses are performed by multi-step growth kinetics in DEF and CEF and compared to the growth properties to parental rMd5-CVI-Meq and rMd5-CVI-LMeq. Briefly, 100 pfu of each virus are used to infect 10, 35-mm cell culture dishes seeded with DEF or CEF. On days 1, 2, 3, 4 and 5 post infection, cells from two dishes are trypsinized and titrated in freshly seeded DEF monolayers. When the viruses become adapted in vitro, they replicate more rapidly.

In Vivo Characterization of Clone Viruses.

In vivo characterization of passage and cloned viruses are carried out in chickens to evaluate specific biological properties: (1) The oncogenic potential of the passage and cloned viruses are measured by determining tumor incidence in maternal antibody negative chickens. (2) Establishment of latency are examined by reactivation of virus from peripheral blood lymphocytes at 2 and 8 weeks post inoculation. (3) Horizontal transmission are determined by testing the ability of the mutant viruses to spread to contact chickens and by virus replication in the feather follicular epithelium. (4) Early cytolytic infection are examined by determining virus replication in lymphoid organs (bursa of Fabricius, spleen and thymus) on 6 days post-infection and by determining lymphoid organ/total body weight ratio on 13 days post-inoculation. Protection studies evaluated the ability of candidate vaccines to protect against challenge with 648A, a vv+ strain of MDV. The in vivo characterization of viruses are carried out in F1 progeny (15×7) of ADOL line $15I_5$ male and line $7_1$ female chickens.

(a) Pathogenesis Studies:

Fifteen maternal antibody negative (15×7) chickens are inoculated subcutaneously with 2000 pfu of each virus and held in isolation units for 8 weeks. All chickens that die or are euthanized at the end of the experiment are examined for the presence of MD specific lesions. At 2 and 8 weeks post inoculation, 3 chickens from each group are bled, buffy coat cells collected and virus reactivation evaluated by adding $10^6$ lymphocytes to DEF monolayers in 35-mm dishes in duplicate. Virus reactivation are measured by counting the number of plaques on day 7. Transmission of passage and cloned viruses are determined by detecting the presence of virus in contact chickens held in the same isolation unit.

(b) Early Cytolytic Infection:

To study early cytolytic infection, 3 chickens (15×7 maternal antibody negative) infected with 2000 pfu of each virus are euthanized 6 days post-infection and the lymphoid organs are collected and examined for virus replication by immunohistochemistry. Briefly, lymphoid organs are embedded in optimal cutting temperature compound (Tissue-Tek OCT; Sakura Finetek, Torrance, Calif.) and tissue blocks immediately frozen in liquid nitrogen, and stored at −80° C. until processed for staining. Eight μm thick sections are prepared from the frozen tissue blocks, fixed with cold acetone at −20° C. for 5 min, and air-dried. Immunostaining are carried out with monoclonal antibodies to pp 38 and gB using Vectastain ABC kit (Burlingame, Calif.).

To determine if the mutant viruses generated are attenuated with regards to lymphoid organ atrophy, lymphoid organ/body weight ratios are determined for 5 chickens (15×7 maternal antibody negative) infected with 2000 pfu of each virus and euthanized 13 days post-infection.

(c) Protection Studies of Passage Cloned Viruses

These studies are carried in F1 progeny of both maternal antibody positive and negative 15×7 chickens. Briefly, 2000 pfu of candidate vaccine viruses are inoculated subcutaneously into 15 day-old chickens and challenged 5 days post vaccination (day 6 of age) with 500 pfu of 648A strain, a vv+ strain, and observed daily for 8 weeks. The protection efficacy of the candidate vaccines are compared to commercial CVI988 vaccine. Unvaccinated chickens inoculated with 648A virus and unvaccinated and uninoculated chickens serve as positive and negative controls, respectively. All chickens that die or are euthanized at the end of the experiment are examined for the presence of MD specific lesions.

Adaptation of rMd5-CVI-LMeq and rMd-CVI-Meq Viruses in Fibroblasts

We have shown that rMd5-CVI-LMeq and rMd5-CVI-Meq are non-pathogenic in MDV maternal antibody positive chickens but are mildly pathogenic in highly susceptible antibody negative chickens (FIG. 9). To further reduce their virulence, rMd5-CVI-Meq and rMd5-CVI-LMeq viruses were subjected to serial passage in CEF and DEF cells. The adaptation of rMd5-CVI-LMeq and rMd5-CVI-Meq viruses was carried out by inoculating confluent monolayers of CEF and DEF cells in 150 mm tissue culture dishes at high multiplicity of infection for 40 rounds. Briefly, viral passage was carried out every 4-7 days post-inoculation when there was approximately 80% cytopathic effect in the monolayer. During early adaptation (1-15 passage level), 20% of the infected cells were used to infect fresh monolayers. As the recombinant viruses adapted to in vitro propagation, they replicated with faster kinetics in CEFs but no in DEFs. Viral stocks generated from both rMd5-CVI-Meq and rMd5-CVI-LMeq, in two cell types (DEF and CEF) were frozen in liquid nitrogen every fifth passage for 40 rounds.

Pathogenesis Experiments

Pathogenesis studies were carried out in MDV maternal antibody negative (Ab−) SPF chickens. Day-old chickens were randomly sorted into experimental groups (13 chickens per test group and 8-10 per control group), held in modified Horsfall-Bauer isolators and provided with water and food ad libitum. One group remained as uninoculated control, and the others were inoculated subcutaneously with 2,000 PFU of rMd5, rMd5-CVI-Meq, rMd5-CVI-LMeq and their cell culture adapted derivatives [rMd5/CVI-LMeq: P20D (passage 20 in DEF), P30D (passage 30 in DEF), P20C (passage 20 in CEF), P30C (passage 30 in CEF); rMd5/CVI-Meq: P20D (passage 20 in DEF), P30D (passage 30 in DEF), P20C (passage 20 in CEF), P30C (passage 30 in CEF)] at 1 day of age. And raised in isolation for up to 8 weeks. Weekly mortality was recorded, and all chickens that died during the experiment or were euthanized at the completion of the experiment were necropsied and evaluated for MDV-specific tumors in the viscera and nerves.

Protection Studies

To study the protection efficacy of rMd5-CVI-Meq, rMd5-CVI-LMeq and their cell culture adapted derivatives (passage 20 and 30 in CEF and DEF), day-old commercial Hyline chicks (15 per group) were vaccinated with 2,000 PFU of rMd5-CVI-Meq, rMd5-CVI-LMeq, their cell culture adapted derivatives (passage 20 and 30) or CVI988 vaccine virus by the subcutaneous route. Five days later, groups of vaccinated and unvaccinated control chickens were challenged by subcutaneous inoculation with 500 PFU of vv+648A MDV. Mortality during the course of the experiment was recorded daily and chickens were examined for gross MD lesions. At 8 weeks post-challenge, all surviving chickens were euthanized and examined for gross MD lesions. The percentage of MD was calculated for each test group as the number of chickens with MD lesions divided by number at risk (survivors+MD deaths)×100. Vaccinal immunity to MD was expressed as protective index (PI) calculated as the percent MD in non-vaccinated challenged control chickens minus the percentage of MD in vaccinated and challenged chickens divided by the percentage of MD in non-vaccinated challenged control chickens×100. Results for the protection studies are shown in FIG. 9.

Generation of Recombinant MDV Containing the Meq Gene from CVI988 and Deletion in the vIL8 and vTR Genes.

MDV cosmid clones SN5-CVIMeq, P89, SN16, A6-CVIMeq, and B40 derived from the very virulent strain, Md5, encompassing the entire MDV genome, were used to generate recombinant Md5 viruses. Cosmid clones A6-CVIMeq and SN5-CVIMeq, containing a copy of the complete coding sequence of the MDV unique gene vIL-8 and telomerase RNA (vTR) in the opposite orientation, are used to introduce deletions in vIL-8 and vTR genes.

The RecA-assisted restriction endonuclease (RARE) cleavage method was used to delete the vIL-8 and vTR genes from the SN5-CVIMeq and A6-CVIMeq cosmid DNAs. Briefly, the SN5-CVIMeq and A6-CVIMeq cosmids were incubated with RecA protein, ADP/ATPs, and two oligonucleotides, vIL-8F (5'-GCC CGC ATC TCG CAG CCC CCG GAT CCG ATC CCG CAG ACC C-3') (SEQ ID NO: 4) and vIL-8R (5'-TCC CCT GCT AGC CCT GCC CTA GGT AAT GCA TTT TAA ATC T-3') (SEQ ID NO: 5), overlapping the two BamHI sites flanking the vIL-8 and vTR sequence (MDV nucleotides 1451 to 4543) to protect these sites from methylation. The protected cosmid DNAs were methylated with BamHI methylase, denatured, and digested with BamHI to generate SN5-CVIMeqΔBamHI and A6-CVIMeqΔBamHI.

To generate rMd5-CVIMeqΔBamHI, DEF were transfected with cosmids SN5-CVIMeqΔBamHI, A6-CVIMeqΔBamHI, P89, SN16 and B40. The resulting virus contained the Meq gene (either long or regular form) from the CVI988 vaccine strain, and deletions in MDV nucleotides 1451-4543 resulting in the loss of vIL8 and vTR genes (SEQ ID NO: 20) (FIG. 24).

Generation of Recombinant MDV Containing the Meq Gene from CVI988 and Deletion in the vIL8 Gene.

To introduce the vIL-8 deletion into the SN5-CVIMeq and A6-CVIMeq cosmids, a 3.1-kb fragment (MDV nucleotides 1451 to 4543) containing the entire sequence of the vIL-8 gene was obtained by digesting the SN5 cosmid with BamHI. This BamHI fragment was cloned into the same site of pUC19, generating the transfer vector pUC19/SN5BamHI. Subsequently, pUC19/SN5BamHI wasbe digested with ClaI (MDV nucleotide 2808) and NcoI (MDV nucleotide 3605), blunt ended, and religated to generate the vIL-8 deletion transfer vector, pUC19/SN5BamHI/ΔvIL-8. The BamHI/ΔvIL8 fragment was cloned into the SN5-CVIMeqΔBamHI and A6-CVIMeqΔBamHI, using RARE cleavage method as described above. Briefly, the BamHI site spanning the deletion site was protected by an oligonucleotide, BamHI-Block 5'-GCT CAG CCC GCA TCT CGC AGC CCC CGG ATC CCG TCC CGA TCG TCC CCT CAC ACG TGG CAC-3' (SEQ ID NO: 6). The protected cosmid DNAs were methylated with BamHI methylase, digested with BamHI, treated with calf intestinal phosphatase and ligated to the BamHI/ΔvIL8 fragment to generate cosmids SN5-CVIMeqΔvIL8 and A6-CVIMeqΔvIL8.

To generate rMd5-CVIMeqΔvIL8, DEF were transfected with cosmids SN5-CVIMeqΔvIL8, A6-CVIMeqΔvIL8, P89, SN16 and B40. The resulting virus had the Meq gene (either long or regular form) from the CVI988 vaccine strain, and deletion in the vIL8 gene (MDV nucleotide 2808-3605) resulting in the loss of vIL8 (SEQ ID NO: 19) (FIG. 23).

Cloning of rMd5-CVI-Meq and rMd5-CVI-LMeq Passed in CEF and DEF.

Cloning of the cell culture adapted viruses is performed by isolating individual plaques using agar overlay method. Briefly, viruses to be cloned is plated in 60 mm dishes and once CPE is evident, media is removed and replaced with 0.6% agar in growth medium. After the agar solidifies, agar on top of each plaque is removed using a wide-bore pipette tip and trypsin added. Trypsin is neutralized with growth media and trypsinized plaques is added to a fresh cell monolayer in 35 mm dishes. The cloning procedure allow the isolation of genotypically distinct viruses from a heterogenous population. The cloning of the adapted series is performed at passage level when the majority of the quasispecies have achieved the attenuated phenotype that result in loss of lymphoid organ atrophy but has retained high level of protection. Since the cloned viruses are genotypically distinct, it allow the identification of mutations (based on sequence comparison and by generation of chimeric viruses). The cloned viruses are subjected to in vitro and in vivo characterization to confirm the presence of desired phenotype.

We claim:

1. A method of immunizing subjects against Marek's disease comprising: a) providing: i) a subject at risk for or exhibiting symptoms associated with Marek's disease, and ii) a composition comprising a modified Md5 strain of Marek's disease virus, said modified strain comprising two mutated Meq genes, said mutated Meq genes having mutations selected from the group consisting of A71S, K77E, T79A, A217P, V283A, T320I, T326I, and combinations thereof, and b) administering said composition to said subject.

2. The method of claim 1, wherein said composition further comprises a pharmaceutically acceptable carrier.

3. The method of claim 1, wherein said subject is a chicken.

4. The method of claim 1, wherein the mode of said administration is selected from the group consisting of optical, oral, parenteral, mucosal, in ovo, buccal, vaginal, rectal, sublingual, inhalation, insufflation, intravenous, intrathecal, subcutaneous and intramuscular.

5. A vaccine comprising: a) at least one modified Md5 strain of Marek's disease virus comprising two mutated Meq genes, said mutated Meq genes having mutations selected from the group consisting of A71 S, K77E, T79A, A217P, V283A, T320I, T326I, A71D, A71 S, and A71E/R72P and combinations thereof; and b) a pharmaceutically acceptable carrier.

6. The vaccine of claim 5, wherein said mutated Meq genes are selected from the group consisting of a Long Meq gene from CVI988, and a regular Meq gene from CVI988.

7. The vaccine of claim 5, wherein said virus further comprises a mutation in at least one gene involved in replication in lymphocytes.

8. The vaccine of claim 5, wherein said virus comprises two inserted nucleic acid sequences comprising a Meq gene from CVI988.

9. The vaccine of claim 7, wherein said mutation in at least one gene involved in replication in lymphocytes is selected from a deletion in the vIL8 gene and a deletion in the vTR gene.

10. A vaccine comprising a modified recombinant Md5 strain of Marek's disease virus with a long or regular Meq gene from CVI988, wherein said virus further comprises a mutation in the vIL8 gene.

11. The method of claim 1, wherein the mode of said administration is in ovo.

* * * * *

SEQUENCE LISTING

```
<160> NUMBER OF SEQ ID NOS: 22

<210> SEQ ID NO 1
<211> LENGTH: 40
<212> TYPE: DNA
<213> ORGANISM: Artificial sequence
<220> FEATURE:
<223> OTHER INFORMATION: synthetic

<400> SEQUENCE: 1
gaatcggatt tggaataacc gaattcggtg atataaagac                    40

<210> SEQ ID NO 2
<211> LENGTH: 40
<212> TYPE: DNA
<213> ORGANISM: Artificial sequence
<220> FEATURE:
<223> OTHER INFORMATION: synthetic

<400> SEQUENCE: 2
gacattacaa gaatagtttg aattctcggg ataatctccc                    40

<210> SEQ ID NO 3
<211> LENGTH: 46
<212> TYPE: DNA
<213> ORGANISM: Artificial sequence
<220> FEATURE:
<223> OTHER INFORMATION: synthetic

<400> SEQUENCE: 3
gaatcggatt tggaataacc gaattctcgg gataatctcc cgatgg             46

<210> SEQ ID NO 4
<211> LENGTH: 40
<212> TYPE: DNA
<213> ORGANISM: Artificial sequence
<220> FEATURE:
<223> OTHER INFORMATION: synthetic
```

<400> SEQUENCE: 4
gcccgcatct cgcagccccc ggatccgatc ccgcagaccc                40

<210> SEQ ID NO 5
<211> LENGTH: 40
<212> TYPE: DNA
<213> ORGANISM: Artificial sequence
<220> FEATURE:
<223> OTHER INFORMATION: synthetic

<400> SEQUENCE: 5
tcccctgcta gccctgccct aggtaatgca ttttaaatct                40

<210> SEQ ID NO 6
<211> LENGTH: 60
<212> TYPE: DNA
<213> ORGANISM: Artificial Sequence
<220> FEATURE:
<223> OTHER INFORMATION: Synthetic

<400> SEQUENCE: 6
gctcagcccg catctcgcag ccccggatc cgtcccgat cgtcccctca cacgtggcac    60

<210> SEQ ID NO 7
<211> LENGTH: 338
<212> TYPE: PRT
<213> ORGANISM: Artificial Sequence
<220> FEATURE:
<223> OTHER INFORMATION: Synthetic

<400> SEQUENCE: 7

Met Ser Gln Glu Pro Glu Pro Gly Ala Met Pro Tyr Ser Pro Ala Asp
1               5                   10                  15

Asp Pro Ser Pro Leu Asp Leu Ser Leu Gly Ser Thr Ser Arg Arg Lys
                20                  25                  30

Lys Arg Lys Ser His Asp Ile Pro Asn Ser Pro Ser Lys His Pro Phe
            35                  40                  45

Pro Asp Gly Leu Ser Glu Glu Glu Lys Gln Lys Leu Glu Arg Arg Arg
        50                  55                  60

Lys Arg Asn Arg Asp Ala Ser Arg Arg Arg Arg Glu Gln Thr Asp
65                  70                  75                  80

Tyr Val Asp Lys Leu His Glu Ala Cys Glu Glu Leu Gln Arg Ala Asn
                85                  90                  95

Glu His Leu Arg Lys Glu Ile Arg Asp Leu Arg Thr Glu Cys Thr Ser
                100                 105                 110

Leu Arg Val Gln Leu Ala Cys His Glu Pro Val Cys Pro Met Ala Val
            115                 120                 125

Pro Leu Thr Val Thr Leu Gly Leu Leu Thr Thr Pro His Asp Pro Val
        130                 135                 140

Pro Glu Pro Pro Ile Cys Thr Pro Pro Pro Ser Pro Asp Glu Pro
145                 150                 155                 160

Asn Ala Pro His Cys Ser Gly Ser Gln Pro Pro Ile Cys Thr Pro Pro
                165                 170                 175

Pro Pro Asp Thr Glu Glu Leu Cys Ala Gln Leu Cys Ser Thr Pro Pro
            180                 185                 190

Pro Ile Ser Thr Pro His Ile Ile Tyr Ala Pro Gly Pro Ser Pro Leu
        195                 200                 205

Gln Pro Pro Ile Cys Thr Pro Pro Pro Pro Asp Ala Glu Glu Leu Cys

```
            210                 215                 220
Ala Gln Leu Cys Ser Thr Pro Pro Pro Ile Cys Thr Pro His Ser
225                 230                 235                 240

Leu Phe Cys Pro Pro Gln Pro Ser Pro Glu Gly Ile Phe Pro Ala
                245                 250                 255

Leu Cys Pro Val Thr Glu Pro Cys Thr Pro Ser Pro Gly Thr Val
                260                 265                 270

Tyr Ala Gln Leu Cys Pro Val Gly Gln Ala Pro Leu Phe Thr Pro Ser
                275                 280                 285

Pro Pro His Pro Ala Pro Glu Pro Glu Arg Leu Tyr Ala Arg Leu Thr
                290                 295                 300

Glu Asp Pro Glu Gln Asp Ser Leu Tyr Ser Gly Gln Ile Tyr Ile Gln
305                 310                 315                 320

Phe Pro Ser Asp Ile Gln Ser Thr Val Trp Trp Phe Pro Gly Asp Gly
                325                 330                 335

Arg Pro

<210> SEQ ID NO 8
<211> LENGTH: 338
<212> TYPE: PRT
<213> ORGANISM: Artificial Sequence
<220> FEATURE:
<223> OTHER INFORMATION: Synthetic

<400> SEQUENCE: 8

Met Ser Gln Glu Pro Glu Pro Gly Ala Met Pro Tyr Ser Pro Ala Asp
1               5                  10                  15

Asp Pro Ser Pro Leu Asp Leu Ser Leu Gly Ser Thr Ser Arg Arg Lys
                20                  25                  30

Lys Arg Lys Ser His Asp Ile Pro Asn Ser Pro Ser Lys His Pro Phe
                35                  40                  45

Pro Asp Gly Leu Ser Glu Glu Lys Gln Lys Leu Glu Arg Arg Arg
                50                  55                  60

Lys Arg Asn Arg Asp Ala Ser Arg Arg Arg Arg Glu Gln Thr Asp
65                  70                  75                  80

Tyr Val Asp Lys Leu His Glu Ala Cys Glu Glu Leu Gln Arg Ala Asn
                85                  90                  95

Glu His Leu Arg Lys Glu Ile Arg Asp Leu Arg Thr Glu Cys Thr Ser
                100                 105                 110

Leu Arg Val Gln Leu Ala Cys His Glu Pro Val Cys Pro Met Ala Val
                115                 120                 125

Pro Leu Thr Val Thr Leu Gly Leu Leu Thr Thr Pro His Asp Pro Val
                130                 135                 140

Pro Glu Pro Pro Ile Cys Thr Pro Pro Pro Ser Pro Asp Glu Pro
145                 150                 155                 160

Asn Ala Pro His Cys Ser Gly Ser Gln Pro Ile Cys Thr Pro Pro
                165                 170                 175

Pro Pro Asp Thr Glu Glu Leu Cys Ala Gln Leu Cys Ser Thr Pro Pro
                180                 185                 190

Pro Ile Ser Thr Pro His Ile Ile Tyr Ala Pro Gly Pro Ser Pro Leu
                195                 200                 205

Gln Pro Pro Ile Cys Thr Pro Pro Pro Asp Ala Glu Glu Leu Cys
                210                 215                 220

Ala Gln Leu Cys Ser Thr Pro Pro Pro Ile Cys Thr Pro His Ser
225                 230                 235                 240
```

```
Leu Phe Cys Pro Pro Gln Pro Pro Ser Pro Glu Gly Ile Phe Pro Ala
                245                 250                 255

Leu Cys Pro Val Thr Glu Pro Cys Thr Pro Ser Pro Gly Thr Val
            260                 265                 270

Tyr Ala Gln Leu Cys Pro Val Gly Gln Ala Pro Leu Phe Thr Pro Ser
            275                 280                 285

Pro Pro His Pro Ala Pro Glu Pro Glu Arg Leu Tyr Ala Arg Leu Thr
            290                 295                 300

Glu Asp Pro Glu Gln Asp Ser Leu Tyr Ser Gly Gln Ile Tyr Ile Gln
305                 310                 315                 320

Phe Pro Ser Asp Ile Gln Ser Thr Val Trp Trp Phe Pro Gly Asp Gly
                325                 330                 335

Arg Pro

<210> SEQ ID NO 9
<211> LENGTH: 398
<212> TYPE: PRT
<213> ORGANISM: Artificial Sequence
<220> FEATURE:
<223> OTHER INFORMATION: Synthetic

<400> SEQUENCE: 9

Met Ser Gln Glu Pro Glu Pro Gly Ala Met Pro Tyr Ser Pro Ala Asp
1               5                   10                  15

Asp Pro Ser Pro Leu Asp Leu Ser Leu Gly Ser Thr Ser Arg Arg Lys
                20                  25                  30

Lys Arg Lys Ser His Asp Ile Pro Asn Ser Pro Ser Lys His Pro Phe
            35                  40                  45

Pro Asp Gly Leu Ser Glu Glu Lys Gln Lys Leu Glu Arg Arg Arg Arg
50                  55                  60

Lys Arg Asn Arg Asp Ala Ser Arg Arg Arg Arg Glu Gln Thr Asp
65                  70                  75                  80

Tyr Val Asp Lys Leu His Glu Ala Cys Glu Glu Leu Gln Arg Ala Asn
                85                  90                  95

Glu His Leu Arg Lys Glu Ile Arg Asp Leu Arg Thr Glu Cys Thr Ser
            100                 105                 110

Leu Arg Val Gln Leu Ala Cys His Glu Pro Val Cys Pro Met Ala Val
            115                 120                 125

Pro Leu Thr Val Thr Leu Gly Leu Leu Thr Thr Pro His Asp Pro Val
130                 135                 140

Pro Glu Pro Pro Ile Cys Thr Pro Pro Pro Ser Pro Asp Glu Pro
145                 150                 155                 160

Asn Ala Pro His Cys Ser Gly Ser Gln Pro Pro Ile Cys Thr Pro Pro
                165                 170                 175

Pro Pro Asp Thr Glu Glu Leu Cys Ala Gln Leu Cys Ser Thr Pro Pro
            180                 185                 190

Pro Ile Ser Thr Pro His Ile Ile Tyr Ala Pro Gly Pro Ser Pro Leu
            195                 200                 205

Gln Pro Pro Ile Cys Thr Pro Pro Pro Asp Ala Glu Glu Leu Cys
210                 215                 220

Ala Gln Leu Cys Ser Thr Pro Pro Pro Ile Ser Thr Pro His Ile
225                 230                 235                 240

Phe Tyr Ala Pro Gly Leu Cys Ser Thr Pro Pro Pro Ile Ser Thr
                245                 250                 255
```

```
Pro His Ile Ile Tyr Ala Pro Gly Pro Ser Pro Leu Gln Pro Pro Ile
            260                 265                 270

Cys Thr Pro Pro Pro Asp Ala Glu Glu Leu Cys Ala Gln Leu Cys
        275                 280                 285

Ser Thr Pro Pro Pro Ile Cys Thr Pro His Ser Leu Phe Cys Pro
    290                 295                 300

Pro Gln Pro Pro Ser Pro Glu Gly Ile Phe Pro Ala Leu Cys Pro Val
305                 310                 315                 320

Thr Glu Pro Cys Thr Pro Pro Ser Pro Gly Thr Val Tyr Ala Gln Leu
            325                 330                 335

Cys Pro Val Gly Gln Ala Pro Leu Phe Thr Pro Ser Pro Pro His Pro
        340                 345                 350

Ala Pro Glu Pro Glu Arg Leu Tyr Ala Arg Leu Thr Glu Asp Pro Glu
        355                 360                 365

Gln Asp Ser Leu Tyr Ser Gly Gln Ile Tyr Ile Gln Phe Pro Ser Asp
        370                 375                 380

Ile Gln Ser Thr Val Trp Trp Phe Pro Gly Asp Gly Arg Pro
385                 390                 395

<210> SEQ ID NO 10
<211> LENGTH: 339
<212> TYPE: PRT
<213> ORGANISM: Artificial Sequence
<220> FEATURE:
<223> OTHER INFORMATION: Synthetic

<400> SEQUENCE: 10

Met Ser Gln Glu Pro Glu Pro Gly Ala Met Pro Tyr Ser Pro Ala Asp
1               5                   10                  15

Asp Pro Ser Pro Leu Asp Leu Ser Leu Gly Ser Thr Ser Arg Arg Lys
            20                  25                  30

Lys Arg Lys Ser His Asp Ile Pro Asn Ser Pro Ser Lys His Pro Phe
        35                  40                  45

Pro Asp Gly Leu Ser Glu Glu Glu Lys Gln Lys Leu Glu Arg Arg Arg
50                  55                  60

Lys Arg Asn Arg Asp Ala Ala Arg Arg Arg Arg Lys Gln Thr Asp
65                  70                  75                  80

Tyr Val Asp Lys Leu His Glu Ala Cys Glu Glu Leu Gln Arg Ala Asn
                85                  90                  95

Glu His Leu Arg Lys Glu Ile Arg Asp Leu Arg Thr Glu Cys Thr Ser
            100                 105                 110

Leu Arg Val Gln Leu Ala Cys His Glu Pro Val Cys Pro Met Ala Val
        115                 120                 125

Pro Leu Thr Val Thr Leu Gly Leu Leu Thr Thr Pro His Asp Pro Val
130                 135                 140

Pro Glu Pro Pro Ile Cys Thr Pro Pro Ser Pro Asp Glu Pro
145                 150                 155                 160

Asn Ala Pro His Cys Ser Gly Ser Gln Pro Ile Cys Thr Pro Pro
                165                 170                 175

Pro Pro Asp Thr Glu Glu Leu Cys Ala Gln Leu Cys Ser Thr Pro Pro
            180                 185                 190

Pro Pro Ile Ser Thr Pro His Ile Ile Tyr Ala Pro Gly Pro Ser Pro
        195                 200                 205

Leu Gln Pro Pro Ile Cys Thr Pro Pro Pro Asp Ala Glu Glu Leu
    210                 215                 220
```

```
Cys Ala Gln Leu Cys Ser Thr Pro Pro Pro Ile Cys Thr Pro His
225                 230                 235                 240

Ser Leu Phe Cys Pro Pro Gln Pro Pro Ser Pro Glu Gly Ile Phe Pro
                245                 250                 255

Ala Leu Cys Pro Val Thr Glu Pro Cys Thr Pro Pro Ser Pro Gly Thr
            260                 265                 270

Val Tyr Ala Gln Leu Cys Pro Val Gly Gln Ala Pro Leu Phe Thr Pro
        275                 280                 285

Ser Pro Pro His Pro Ala Pro Glu Pro Glu Arg Leu Tyr Ala Arg Leu
    290                 295                 300

Thr Glu Asp Pro Glu Gln Asp Ser Leu Tyr Ser Gly Gln Ile Tyr Ile
305                 310                 315                 320

Gln Phe Pro Ser Asp Ile Gln Ser Thr Val Trp Trp Phe Pro Gly Asp
                325                 330                 335

Gly Arg Pro

<210> SEQ ID NO 11
<211> LENGTH: 339
<212> TYPE: PRT
<213> ORGANISM: Artificial Sequence
<220> FEATURE:
<223> OTHER INFORMATION: Synthetic

<400> SEQUENCE: 11

Met Ser Gln Glu Pro Glu Pro Gly Ala Met Pro Tyr Ser Pro Ala Asp
1               5                   10                  15

Asp Pro Ser Pro Leu Asp Leu Ser Leu Gly Ser Thr Ser Arg Arg Lys
            20                  25                  30

Lys Arg Lys Ser His Asp Ile Pro Asn Ser Pro Ser Lys His Pro Phe
        35                  40                  45

Pro Asp Gly Leu Ser Glu Glu Glu Lys Gln Lys Leu Glu Arg Arg Arg
    50                  55                  60

Lys Arg Asn Arg Asp Ala Ser Arg Arg Arg Arg Glu Gln Thr Asp
65                  70                  75                  80

Tyr Val Asp Lys Leu His Glu Ala Cys Glu Glu Leu Gln Arg Ala Asn
                85                  90                  95

Glu His Leu Arg Lys Glu Ile Arg Asp Leu Arg Thr Glu Cys Thr Ser
            100                 105                 110

Leu Arg Val Gln Leu Ala Cys His Glu Pro Val Cys Pro Met Ala Val
        115                 120                 125

Pro Leu Thr Val Thr Leu Gly Leu Leu Thr Thr Pro His Asp Pro Val
130                 135                 140

Pro Glu Pro Pro Ile Cys Thr Pro Pro Pro Ser Pro Asp Glu Pro
145                 150                 155                 160

Asn Ala Pro His Cys Ser Gly Ser Gln Pro Pro Ile Cys Thr Pro Pro
                165                 170                 175

Pro Pro Asp Thr Glu Glu Leu Cys Ala Gln Leu Cys Ser Thr Pro Pro
            180                 185                 190

Pro Pro Ile Ser Thr Pro His Ile Ile Tyr Ala Pro Gly Pro Ser Pro
        195                 200                 205

Leu Gln Pro Pro Ile Cys Thr Pro Ala Pro Pro Asp Ala Glu Glu Leu
    210                 215                 220

Cys Ala Gln Leu Cys Ser Thr Pro Pro Pro Ile Cys Thr Pro His
225                 230                 235                 240

Ser Leu Phe Cys Pro Pro Gln Pro Pro Ser Pro Glu Gly Ile Phe Pro
```

```
                    245                 250                 255
Ala Leu Cys Pro Val Thr Glu Pro Cys Thr Pro Ser Pro Gly Thr
                260                 265                 270

Val Tyr Ala Gln Leu Cys Pro Gly Gln Val Pro Leu Phe Thr Pro
            275                 280                 285

Ser Pro Pro His Pro Ala Pro Glu Pro Glu Arg Leu Tyr Ala Arg Leu
        290                 295                 300

Thr Glu Asp Pro Glu Gln Asp Ser Leu Tyr Ser Gly Gln Ile Tyr Thr
305                 310                 315                 320

Gln Phe Pro Ser Asp Thr Gln Ser Thr Val Trp Trp Phe Pro Gly Asp
                325                 330                 335

Gly Arg Pro

<210> SEQ ID NO 12
<211> LENGTH: 339
<212> TYPE: PRT
<213> ORGANISM: Artificial Sequence
<220> FEATURE:
<223> OTHER INFORMATION: Synthetic

<400> SEQUENCE: 12

Met Ser Gln Glu Pro Glu Pro Gly Ala Met Pro Tyr Ser Pro Ala Asp
1               5                   10                  15

Asp Pro Ser Pro Leu Asp Leu Ser Leu Gly Ser Ala Ser Arg Arg Lys
                20                  25                  30

Lys Arg Lys Ser His Asp Ile Pro Asn Ser Pro Ser Lys His Pro Phe
            35                  40                  45

Pro Asp Gly Leu Ser Glu Glu Glu Lys Gln Lys Leu Glu Arg Arg Arg
50                  55                  60

Lys Arg Asn Arg Asp Ala Ala Arg Arg Arg Arg Lys Gln Thr Asp
65                  70                  75                  80

Tyr Val Asp Lys Leu His Glu Ala Cys Glu Glu Leu Gln Arg Ala Asn
                85                  90                  95

Glu His Leu Arg Lys Glu Ile Arg Asp Leu Arg Thr Glu Cys Thr Ser
            100                 105                 110

Leu Arg Val Gln Leu Ala Cys His Glu Pro Val Cys Pro Met Ala Val
        115                 120                 125

Pro Leu Thr Val Thr Leu Gly Leu Leu Thr Thr Pro His Asp Pro Val
    130                 135                 140

Pro Glu Pro Pro Ile Cys Thr Pro Pro Pro Ser Pro Asp Glu Pro
145                 150                 155                 160

Asn Ala Pro His Cys Ser Gly Ser Gln Pro Pro Ile Cys Thr Pro Pro
                165                 170                 175

Pro Pro Asp Thr Glu Glu Leu Cys Ala Gln Leu Cys Ser Thr Pro Pro
            180                 185                 190

Pro Pro Ile Ser Thr Pro His Ile Ile Tyr Ala Pro Gly Pro Ser Pro
        195                 200                 205

Leu Gln Pro Pro Ile Cys Thr Pro Ala Pro Pro Asp Ala Glu Glu Leu
    210                 215                 220

Cys Ala Gln Leu Cys Ser Thr Pro Pro Pro Ile Cys Thr Pro His
225                 230                 235                 240

Ser Leu Phe Cys Pro Pro Gln Pro Pro Ser Pro Glu Gly Ile Phe Pro
                245                 250                 255

Ala Leu Cys Pro Val Thr Glu Pro Cys Thr Pro Pro Ser Pro Gly Thr
            260                 265                 270
```

```
Val Tyr Ala Gln Leu Cys Pro Val Gly Gln Val Pro Leu Phe Thr Pro
        275                 280                 285

Ser Pro Pro His Pro Ala Pro Glu Pro Glu Arg Leu Tyr Ala Arg Leu
        290                 295                 300

Thr Glu Asp Pro Glu Gln Asp Ser Leu Tyr Ser Gly Gln Ile Tyr Thr
305                 310                 315                 320

Gln Phe Pro Ser Asp Thr Gln Ser Thr Val Trp Trp Phe Pro Gly Asp
                325                 330                 335

Gly Arg Pro

<210> SEQ ID NO 13
<211> LENGTH: 339
<212> TYPE: PRT
<213> ORGANISM: Artificial Sequence
<220> FEATURE:
<223> OTHER INFORMATION: Synthetic

<400> SEQUENCE: 13

Met Ser Gln Glu Pro Glu Pro Gly Ala Met Pro Tyr Ser Pro Ala Asp
1               5                   10                  15

Asp Pro Ser Pro Leu Asp Leu Ser Leu Gly Ser Thr Ser Arg Arg Lys
            20                  25                  30

Lys Arg Lys Ser His Asp Ile Pro Asn Ala Pro Ser Lys His Pro Phe
        35                  40                  45

Pro Asp Gly Leu Ser Glu Glu Lys Gln Lys Leu Glu Arg Arg Arg
    50                  55                  60

Lys Arg Asn Arg Asp Ala Arg Arg Arg Arg Lys Gln Thr Asp
65                  70                  75                  80

Tyr Val Asp Lys Leu His Glu Ala Cys Glu Glu Leu Gln Arg Ala Asn
                85                  90                  95

Glu His Leu Arg Lys Glu Ile Arg Asp Leu Arg Thr Glu Cys Thr Ser
            100                 105                 110

Leu Arg Val Gln Leu Ala Cys His Glu Pro Val Cys Pro Met Ala Val
        115                 120                 125

Pro Leu Thr Val Thr Leu Gly Leu Leu Thr Thr Pro His Asp Pro Val
    130                 135                 140

Pro Glu Pro Pro Ile Cys Thr Pro Pro Ser Pro Asp Glu Pro
145                 150                 155                 160

Asn Ala Pro His Cys Ser Gly Ser Gln Pro Ile Cys Thr Pro
                165                 170                 175

Pro Pro Asp Thr Glu Glu Leu Cys Ala Gln Leu Cys Ser Thr Pro Pro
            180                 185                 190

Pro Pro Ile Ser Thr Pro His Ile Ile Tyr Ala Pro Gly Pro Ser Pro
        195                 200                 205

Leu Gln Pro Pro Ile Cys Thr Pro Ala Pro Asp Ala Glu Glu Leu
    210                 215                 220

Cys Ala Gln Leu Cys Ser Thr Pro Pro Pro Ile Cys Thr Pro His
225                 230                 235                 240

Ser Leu Phe Cys Pro Pro Gln Pro Pro Ser Glu Gly Ile Phe Pro
                245                 250                 255

Ala Leu Cys Pro Val Thr Glu Pro Cys Thr Pro Ser Pro Gly Thr
            260                 265                 270

Val Tyr Ala Gln Leu Cys Pro Val Gly Gln Val Pro Leu Phe Thr Pro
        275                 280                 285
```

```
Ser Pro Pro His Pro Ala Pro Glu Pro Glu Arg Leu Tyr Ala Arg Leu
    290                 295                 300

Thr Glu Asp Pro Glu Gln Asp Ser Leu Tyr Ser Gly Gln Ile Tyr Thr
305                 310                 315                 320

Gln Phe Pro Ser Asp Thr Gln Ser Thr Val Trp Trp Phe Pro Gly Asp
                325                 330                 335

Gly Arg Pro

<210> SEQ ID NO 14
<211> LENGTH: 339
<212> TYPE: PRT
<213> ORGANISM: Artificial Sequence
<220> FEATURE:
<223> OTHER INFORMATION: Synthetic

<400> SEQUENCE: 14

Met Ser Gln Glu Pro Glu Pro Gly Ala Met Pro Tyr Ser Pro Ala Asp
1               5                   10                  15

Asp Pro Ser Pro Leu Asp Leu Ser Leu Gly Ser Thr Ser Arg Arg Lys
                20                  25                  30

Lys Arg Lys Ser His Asp Ile Pro Asn Asp Pro Ser Lys His Pro Phe
            35                  40                  45

Pro Asp Gly Leu Ser Glu Glu Lys Gln Lys Leu Glu Arg Arg Arg
50                  55                  60

Lys Arg Asn Arg Asp Ala Ala Arg Arg Arg Arg Lys Gln Thr Asp
65                  70                  75                  80

Tyr Val Asp Lys Leu His Glu Ala Cys Glu Glu Leu Gln Arg Ala Asn
                85                  90                  95

Glu His Leu Arg Lys Glu Ile Arg Asp Leu Arg Thr Glu Cys Thr Ser
            100                 105                 110

Leu Arg Val Gln Leu Ala Cys His Glu Pro Val Cys Pro Met Ala Val
        115                 120                 125

Pro Leu Thr Val Thr Leu Gly Leu Leu Thr Thr Pro His Asp Pro Val
    130                 135                 140

Pro Glu Pro Pro Ile Cys Thr Pro Pro Pro Ser Pro Asp Glu Pro
145                 150                 155                 160

Asn Ala Pro His Cys Ser Gly Ser Gln Pro Pro Ile Cys Thr Pro Pro
                165                 170                 175

Pro Pro Asp Thr Glu Glu Leu Cys Ala Gln Leu Cys Ser Thr Pro Pro
            180                 185                 190

Pro Pro Ile Ser Thr Pro His Ile Ile Tyr Ala Pro Gly Pro Ser Pro
        195                 200                 205

Leu Gln Pro Pro Ile Cys Thr Pro Ala Pro Pro Asp Ala Glu Glu Leu
    210                 215                 220

Cys Ala Gln Leu Cys Ser Thr Pro Pro Pro Ile Cys Thr Pro His
225                 230                 235                 240

Ser Leu Phe Cys Pro Pro Gln Pro Pro Ser Pro Glu Gly Ile Phe Pro
                245                 250                 255

Ala Leu Cys Pro Val Thr Glu Pro Cys Thr Pro Pro Ser Pro Gly Thr
            260                 265                 270

Val Tyr Ala Gln Leu Cys Pro Val Gly Gln Val Pro Leu Phe Thr Pro
        275                 280                 285

Ser Pro Pro His Pro Ala Pro Glu Pro Glu Arg Leu Tyr Ala Arg Leu
    290                 295                 300

Thr Glu Asp Pro Glu Gln Asp Ser Leu Tyr Ser Gly Gln Ile Tyr Thr
```

Gln Phe Pro Ser Asp Thr Gln Ser Thr Val Trp Trp Phe Pro Gly Asp
            325                 330                 335

Gly Arg Pro

<210> SEQ ID NO 15
<211> LENGTH: 339
<212> TYPE: PRT
<213> ORGANISM: Artificial Sequence
<220> FEATURE:
<223> OTHER INFORMATION: Synthetic

<400> SEQUENCE: 15

Met Ser Gln Glu Pro Glu Pro Gly Ala Met Pro Tyr Ser Pro Ala Asp
1               5                   10                  15

Asp Pro Ser Pro Leu Asp Leu Ser Leu Gly Ser Thr Ser Arg Arg Lys
            20                  25                  30

Lys Arg Lys Ser His Asp Ile Pro Asn Ser Pro Lys His Pro Phe
        35                  40                  45

Pro Asp Gly Leu Ser Glu Glu Lys Gln Lys Leu Glu Arg Arg Arg
    50                  55                  60

Lys Arg Asn Arg Asp Ala Ser Arg Arg Arg Arg Lys Gln Thr Asp
65                  70                  75                  80

Tyr Val Asp Lys Leu His Glu Ala Cys Glu Glu Leu Gln Arg Ala Asn
                85                  90                  95

Glu His Leu Arg Lys Glu Ile Arg Asp Leu Arg Thr Glu Cys Thr Ser
            100                 105                 110

Leu Arg Val Gln Leu Ala Cys His Glu Pro Val Cys Pro Met Ala Val
        115                 120                 125

Pro Leu Thr Val Thr Leu Gly Leu Leu Thr Thr Pro His Asp Pro Val
    130                 135                 140

Pro Glu Pro Pro Ile Cys Thr Pro Pro Pro Ser Pro Asp Glu Pro
145                 150                 155                 160

Asn Ala Pro His Cys Ser Gly Ser Gln Pro Pro Ile Cys Thr Pro Pro
                165                 170                 175

Pro Pro Asp Thr Glu Glu Leu Cys Ala Gln Leu Cys Ser Thr Pro Pro
            180                 185                 190

Pro Pro Ile Ser Thr Pro His Ile Ile Tyr Ala Pro Gly Pro Ser Pro
        195                 200                 205

Leu Gln Pro Pro Ile Cys Thr Pro Ala Pro Pro Asp Ala Glu Glu Leu
    210                 215                 220

Cys Ala Gln Leu Cys Ser Thr Pro Pro Pro Ile Cys Thr Pro His
225                 230                 235                 240

Ser Leu Phe Cys Pro Pro Gln Pro Pro Ser Pro Glu Gly Ile Phe Pro
                245                 250                 255

Ala Leu Cys Pro Val Thr Glu Pro Cys Thr Pro Pro Ser Pro Gly Thr
            260                 265                 270

Val Tyr Ala Gln Leu Cys Pro Val Gly Gln Val Pro Leu Phe Thr Pro
        275                 280                 285

Ser Pro Pro His Pro Ala Pro Glu Pro Glu Arg Leu Tyr Ala Arg Leu
    290                 295                 300

Thr Glu Asp Pro Glu Gln Asp Ser Leu Tyr Ser Gly Gln Ile Tyr Thr
305                 310                 315                 320

Gln Phe Pro Ser Asp Thr Gln Ser Thr Val Trp Trp Phe Pro Gly Asp
                325                 330                 335

Gly Arg Pro

<210> SEQ ID NO 16
<211> LENGTH: 339
<212> TYPE: PRT
<213> ORGANISM: Artificial Sequence
<220> FEATURE:
<223> OTHER INFORMATION: Synthetic

<400> SEQUENCE: 16

```
Met Ser Gln Glu Pro Glu Pro Gly Ala Met Pro Tyr Ser Pro Ala Asp
1               5                   10                  15

Asp Pro Ser Pro Leu Asp Leu Ser Leu Gly Ser Thr Ser Arg Arg Lys
            20                  25                  30

Lys Arg Lys Ser His Asp Ile Pro Asn Ser Pro Ser Lys His Pro Phe
        35                  40                  45

Pro Asp Gly Leu Ser Glu Glu Lys Gln Lys Leu Glu Arg Arg Arg
    50                  55                  60

Lys Arg Asn Arg Asp Ala Asp Arg Arg Arg Arg Lys Gln Thr Asp
65                  70                  75                  80

Tyr Val Asp Lys Leu His Glu Ala Cys Glu Glu Leu Gln Arg Ala Asn
                85                  90                  95

Glu His Leu Arg Lys Glu Ile Arg Asp Leu Arg Thr Glu Cys Thr Ser
            100                 105                 110

Leu Arg Val Gln Leu Ala Cys His Glu Pro Val Cys Pro Met Ala Val
        115                 120                 125

Pro Leu Thr Val Thr Leu Gly Leu Leu Thr Thr Pro His Asp Pro Val
    130                 135                 140

Pro Glu Pro Pro Ile Cys Thr Pro Pro Pro Ser Pro Asp Glu Pro
145                 150                 155                 160

Asn Ala Pro His Cys Ser Gly Ser Gln Pro Pro Ile Cys Thr Pro Pro
                165                 170                 175

Pro Pro Asp Thr Glu Glu Leu Cys Ala Gln Leu Cys Ser Thr Pro Pro
            180                 185                 190

Pro Pro Ile Ser Thr Pro His Ile Ile Tyr Ala Pro Gly Pro Ser Pro
        195                 200                 205

Leu Gln Pro Pro Ile Cys Thr Pro Ala Pro Pro Asp Ala Glu Glu Leu
    210                 215                 220

Cys Ala Gln Leu Cys Ser Thr Pro Pro Pro Ile Cys Thr Pro His
225                 230                 235                 240

Ser Leu Phe Cys Pro Pro Gln Pro Pro Ser Pro Glu Gly Ile Phe Pro
                245                 250                 255

Ala Leu Cys Pro Val Thr Glu Pro Cys Thr Pro Pro Ser Pro Gly Thr
            260                 265                 270

Val Tyr Ala Gln Leu Cys Pro Val Gly Gln Val Pro Leu Phe Thr Pro
        275                 280                 285

Ser Pro Pro His Pro Ala Pro Glu Pro Glu Arg Leu Tyr Ala Arg Leu
    290                 295                 300

Thr Glu Asp Pro Glu Gln Asp Ser Leu Tyr Ser Gly Gln Ile Tyr Thr
305                 310                 315                 320

Gln Phe Pro Ser Asp Thr Gln Ser Thr Val Trp Trp Phe Pro Gly Asp
                325                 330                 335

Gly Arg Pro
```

<210> SEQ ID NO 17
<211> LENGTH: 339
<212> TYPE: PRT
<213> ORGANISM: Artificial Sequence
<220> FEATURE:
<223> OTHER INFORMATION: Synthetic

<400> SEQUENCE: 17

Met Ser Gln Glu Pro Glu Pro Gly Ala Met Pro Tyr Ser Pro Ala Asp
1               5                   10                  15

Asp Pro Ser Pro Leu Asp Leu Ser Leu Gly Ser Thr Ser Arg Arg Lys
            20                  25                  30

Lys Arg Lys Ser His Asp Ile Pro Asn Ser Pro Ser Lys His Pro Phe
        35                  40                  45

Pro Asp Gly Leu Ser Glu Glu Lys Gln Lys Leu Glu Arg Arg Arg
    50                  55                  60

Lys Arg Asn Arg Asp Ala Glu Pro Arg Arg Arg Lys Gln Thr Asp
65                  70                  75                  80

Tyr Val Asp Lys Leu His Glu Ala Cys Glu Glu Leu Gln Arg Ala Asn
                85                  90                  95

Glu His Leu Arg Lys Glu Ile Arg Asp Leu Arg Thr Glu Cys Thr Ser
            100                 105                 110

Leu Arg Val Gln Leu Ala Cys His Glu Pro Val Cys Pro Met Ala Val
        115                 120                 125

Pro Leu Thr Val Thr Leu Gly Leu Leu Thr Thr Pro His Asp Pro Val
    130                 135                 140

Pro Glu Pro Pro Ile Cys Thr Pro Pro Pro Ser Pro Asp Glu Pro
145                 150                 155                 160

Asn Ala Pro His Cys Ser Gly Ser Gln Pro Pro Ile Cys Thr Pro Pro
                165                 170                 175

Pro Pro Asp Thr Glu Glu Leu Cys Ala Gln Leu Cys Ser Thr Pro Pro
            180                 185                 190

Pro Pro Ile Ser Thr Pro His Ile Ile Tyr Ala Pro Gly Pro Ser Pro
        195                 200                 205

Leu Gln Pro Pro Ile Cys Thr Pro Ala Pro Pro Asp Ala Glu Glu Leu
    210                 215                 220

Cys Ala Gln Leu Cys Ser Thr Pro Pro Pro Ile Cys Thr Pro His
225                 230                 235                 240

Ser Leu Phe Cys Pro Pro Gln Pro Pro Ser Pro Glu Gly Ile Phe Pro
                245                 250                 255

Ala Leu Cys Pro Val Thr Glu Pro Cys Thr Pro Pro Ser Pro Gly Thr
            260                 265                 270

Val Tyr Ala Gln Leu Cys Pro Val Gly Gln Val Pro Leu Phe Thr Pro
        275                 280                 285

Ser Pro Pro His Pro Ala Pro Glu Pro Glu Arg Leu Tyr Ala Arg Leu
    290                 295                 300

Thr Glu Asp Pro Glu Gln Asp Ser Leu Tyr Ser Gly Gln Ile Tyr Thr
305                 310                 315                 320

Gln Phe Pro Ser Asp Thr Gln Ser Thr Val Trp Trp Phe Pro Gly Asp
                325                 330                 335

Gly Arg Pro

<210> SEQ ID NO 18
<211> LENGTH: 339
<212> TYPE: PRT
<213> ORGANISM: Artificial Sequence
<220> FEATURE:
<223> OTHER INFORMATION: Synthetic

<400> SEQUENCE: 18

Met Ser Gln Glu Pro Glu Pro Gly Ala Met Pro Tyr Ser Pro Ala Asp
1               5                   10                  15

Asp Pro Ser Pro Leu Asp Leu Ser Leu Gly Ser Thr Ser Arg Arg Lys
            20                  25                  30

Lys Arg Lys Ser His Asp Ile Pro Asn Ser Pro Ser Lys His Pro Phe
        35                  40                  45

Pro Asp Gly Leu Ser Glu Glu Lys Gln Lys Leu Glu Arg Arg Arg
    50                  55                  60

Lys Arg Asn Arg Asp Ala Ala Arg Arg Arg Arg Lys Gln Ala Asp
65                  70                  75                  80

Tyr Val Asp Lys Leu His Glu Ala Cys Glu Glu Leu Gln Arg Ala Asn
                85                  90                  95

Glu His Leu Arg Lys Glu Ile Arg Asp Leu Arg Thr Glu Cys Thr Ser
            100                 105                 110

Leu Arg Val Gln Leu Ala Cys His Glu Pro Val Cys Pro Met Ala Val
        115                 120                 125

Pro Leu Thr Val Thr Leu Gly Leu Leu Thr Thr Pro His Asp Pro Val
    130                 135                 140

Pro Glu Pro Pro Ile Cys Thr Pro Pro Pro Ser Pro Asp Glu Pro
145                 150                 155                 160

Asn Ala Pro His Cys Ser Gly Ser Gln Pro Pro Ile Cys Thr Pro Pro
                165                 170                 175

Pro Pro Asp Thr Glu Glu Leu Cys Ala Gln Leu Cys Ser Thr Pro Pro
            180                 185                 190

Pro Pro Ile Ser Thr Pro His Ile Ile Tyr Ala Pro Gly Pro Ser Pro
        195                 200                 205

Leu Gln Pro Pro Ile Cys Thr Pro Ala Pro Pro Asp Ala Glu Glu Leu
    210                 215                 220

Cys Ala Gln Leu Cys Ser Thr Pro Pro Pro Ile Cys Thr Pro His
225                 230                 235                 240

Ser Leu Phe Cys Pro Pro Gln Pro Pro Ser Pro Glu Gly Ile Phe Pro
                245                 250                 255

Ala Leu Cys Pro Val Thr Glu Pro Cys Thr Pro Ser Pro Gly Thr
            260                 265                 270

Val Tyr Ala Gln Leu Cys Pro Val Gly Gln Val Pro Leu Phe Thr Pro
        275                 280                 285

Ser Pro Pro His Pro Ala Pro Glu Pro Glu Arg Leu Tyr Ala Arg Leu
    290                 295                 300

Thr Glu Asp Pro Glu Gln Asp Ser Leu Tyr Ser Gly Gln Ile Tyr Thr
305                 310                 315                 320

Gln Phe Pro Ser Asp Thr Gln Ser Thr Val Trp Trp Phe Pro Gly Asp
                325                 330                 335

Gly Arg Pro

<210> SEQ ID NO 19
<211> LENGTH: 2300
<212> TYPE: DNA
<213> ORGANISM: Artificial Sequence
<220> FEATURE:
<223> OTHER INFORMATION: Synthetic

<400> SEQUENCE: 19

-continued

```
gatccgatcc cgcagacccc ggcccacagg aaggggcggg gcacgtgcat ggggcgtggc      60
gggagatgaa tgaccgcgga gttccaaact cccgcaccgg cccctctctg ctcgctctcc     120
tccccgccgc caatagctac gcggcagcgt acagcccggc caataggcgc gcggtgggcg     180
taggcggagg aagctacaag agccccacgc ggggttcccc cggcacacgt ggcgggtgga     240
aggctccgct gtgtctaacc ctaatcggag gtattgatgg tactgtcgcc gcgctccctc     300
cgcccgctgt ttactcgctg actttcagcg ggctagggga gccgcccag ggggcgccgc      360 ggcggggagg gggtggggcg gacgcggag aaaggaccga aagggctcc acggcaaaca      420 aaaaaaaacg tcagcgaggg gtcctctcgc ccccatccgc cctggggtcc tcgcccgcag     480
gccgcggtcg gccggcaccc gccattgccg ccgcgaagag ttcgcctctg tcagcctcgg     540
cggcgcccgg gagatgcggc gcgcggcccc gcgcccccag cagagcaaca cgggagcggc     600
gccccggggg caaccccgc gccccctgc gccgtggggc gcgcggacgg cgtcgctccc       660
acacgcgcgg ccccgcgcgc acgaccgttg gagccgttga gccgcgcgcg gggctctgtg     720
agtagaccga acgggccccc cgcggaggtg ggcgctcgag cccggtccct gcgcaggtgg     780
tgcccgctgg gcgccgctcg gggctaccgg ggtccgtccg cggccgtgcc gggcgcccag     840
gcgccgagtc ctggcctgga cgtgtggcgg tgcgcagcgc ggagccctgt cccggcagga     900
gccgtcctct gcctcggcac gctccgcaat aagcgtgggc aaacgtgtgg gccgtgcagg     960
gcatgagcgt gcacaaagac gtggccctgg ggcttgggct gagcgcagtg cgatgccccc    1020
gggtcatcac ccgtcccgca gatccccgtg cacggggtca gtgccatctt gtggtctcgg    1080
cttctttttt tcccccttt gcacgaagag tcagtgaact tggggtactt aatcgtgctt     1140
taattgcgcg atggagaacc gttgctagaa tatgtgggga tagagaagtc cgataccctc    1200
agaaatgtgc gagtcctgcg ggtagaatcg gcgcagcact gaataaaccc gcggggccct    1260
aaaacctctc gcggccgaca gacagttgta cacctgcctg cattactaca tccagttcgt    1320
agaccgtatc cctgctccat ccaatagcta cattatcgca tggaaccgta cccgtaatgc    1380
ctcgggcgat ttccctgtta ttgggtctcc accaacacgt gatattggag accccccaact   1440 taaaattcca cgaccgtgag atgcattttg tttattgaaa atttccattc gatggggcat    1500
aaactatagc atcgaaacac taaaatgaac aggagtttgc atcaaaaggt gataatactg    1560
gaacacaaga ctatgaggac ccttaaatgt atatgagaaa attcccacga cccctgcata    1620
gcagaaaacc aggaccacaa taaattttgc agtacgcatg cgccctctac acacgacccg    1680
catgcgctga ccacttactg cagtacgcat gcgccctcta cacacaaaac gcatgcgcag    1740
tccaaaacgc atgcgcagac cgcttacggc agtacgcatg cgccctctac acacaaaacg    1800
catgcgcaga ccaattaccc aaaacaagca tgcgccgtaa gtatggttat ctgcgcatgc    1860
ctggttttcg acacacgcgc atgcgcagat acactccacc gtacgcatgc gcgtcatgca    1920
taactggcgc atgcgtgaac gccttacccg aaccagccct gcgcgcttgc gctatatacg    1980
ccctgcgcac tcatcgcgca tgcgcacaga cgttcaaata atggcggaca tttccgtcaa    2040
caaacgcact aaggtaaaaa aaaaaaccac gaaccgttag tttttaggag ctacgattta    2100
attttcatgc tctgctttat caagactcga aatgcgttac agcttccccc cgtaccggca    2160
ccgacagttc tttacgtaag cccttcccgt tcactctttc acgcgcggca ctatcggtac    2220
aacagtggca cacatcaaac aaagtaaaag gggaagggaa ttgaatttct acaaagagatc   2280 taaattttac gtaatggatc                                                2300
```

<210> SEQ ID NO 20
<211> LENGTH: 1097
<212> TYPE: DNA
<213> ORGANISM: Artificial Sequence
<220> FEATURE:
<223> OTHER INFORMATION: Synthetic

<400> SEQUENCE: 20

| | | | | | | |
|---|---|---|---|---|---|---|
| tgaaccctaa | ccctaaccct | aaccctaacc | ctaaccctaa | ccctaaccct | aaccctaacc | 60 |
| ctaaccccccc | aaattttcac | ccccccctcac | ccccatccaa | aataagccaa | atataatgta | 120 |
| gaggatggga | gaatccgggg | gcgataagac | actttcccac | tcatactgaa | gatgtcttaa | 180 |
| ccgtgaacct | agtctcgatc | ccgagctcaa | agcacggaaa | tccacactgg | aaccggcaca | 240 |
| taccacctgt | gatgtgacgc | aaacttggat | tatgcaagtg | gtgactccgt | ggtgtgaaat | 300 |
| tagaccccccc | ctgtttctcg | accccccacc | ctaaccctaa | ccctaaccct | aaccctaacc | 360 |
| ctaaccccca | aaaacctctc | gcggccgaca | ggcagttgta | cacctgcctg | cactactaca | 420 |
| tccggtccgt | agaccacatc | cctgctccat | ccaataactc | gaacgctctt | cctataggta | 480 |
| gatacaggac | atgttttaac | gaggttctgc | gctaaatcca | gggcgggaaa | gctcagcccg | 540 |
| catctcgcag | cccccggatc | ccgtcccgat | cgtcccctca | cacgtggcac | tgccgcgtaa | 600 |
| acaatgccac | atcgtagaga | aagcataagg | gggaggccat | cgggagatta | tcccgagaat | 660 |
| tcaaactatt | cttgtaatgt | cgtacgagcc | tcgttccgtt | cgctctttca | tgcgcagcat | 720 |
| taccggtgta | aatgtaataa | tgccgcacag | tgaacaagca | aaaggggaag | agagtctccg | 780 |
| gatagccgtt | acaatccagt | aacgacttaa | cgcagattac | tcctgcataa | gcgtctctgc | 840 |
| gatgaggtat | tttccatatg | ttcctggagg | tccgtgcctg | tatattcgtt | aatgtcgaca | 900 |
| tctgcctatg | tgcctgtgta | tcggtgcata | ggagtatgtc | tgtgcatccc | tgtatatatt | 960 |
| atctgtgcat | atttgcataa | ttcataaacg | aatatttaat | tacagtagtg | ttgcgcgagc | 1020 |
| cccgatccat | tgatctgctc | acgactgtag | cacttagaat | cgcacagtgc | acagccagtg | 1080 |
| agctggccac | aggagag | | | | | 1097 |

<210> SEQ ID NO 21
<211> LENGTH: 2639
<212> TYPE: DNA
<213> ORGANISM: Artificial Sequence
<220> FEATURE:
<223> OTHER INFORMATION: synthetic

<400> SEQUENCE: 21

| | | | | | | |
|---|---|---|---|---|---|---|
| aattcaaact | attcttgtaa | tgtcgtacga | gcctcgttcc | gttcgctctt | tcatgcgcag | 60 |
| cattaccggt | gtaaatgtaa | taatgccgca | cagtgaacaa | gcaaaagggg | aagagagtct | 120 |
| ccggatagcc | gttacaatcc | agtaacgact | taacgcagat | tactcctgca | taagcgtctc | 180 |
| tgcgatgagg | tattttccat | atgttcctgg | aggtccgtgc | ctgtatattc | gttaatgtcg | 240 |
| acatctgcct | atgtgcctgt | gtatcggtgc | ataggagtat | gtctgtgcat | ccctgtatat | 300 |
| attatctgtg | catatttgca | taattcataa | acgaatattt | aattacagta | gtgttgcgcg | 360 |
| agcccccgatc | cattgatctg | ctcacgactg | tagcacttag | aatcgcacag | tgcacagcca | 420 |
| gtgagctggc | cacaggagag | ggacataggc | ctgattgctg | ggacgcggat | gagagatcaa | 480 |
| tcgtgttgtt | ccttacgata | acctaatcag | caccaccgaa | ttatacgaga | ctgcattaac | 540 |
| tcacatctgc | taaaggtttc | gcttattcct | tttacatccg | aatgtccatc | ctgttatctt | 600 |
| taatattcct | taatgtgcga | tgtccatatc | ccttctaaaa | aaaaaaacag | ccaggcatag | 660 |

```
ttttgagcc tggaaaactt accgcaggct tcatagaagc catatcccga ataatactcc      720
atataccccc ccccttccc caaccgttct gtatagaacg agaatttgcc atttaagcag      780
tctggggccg agagatgttg ccccagaagt tttccacata gctaagttta tctcatactt    840
cggaactcct ggagccaaca atcccctga ccatgtaact caaatagtt cttccgagtc      900
taagctacac ggtaaggaaa atttgttacc ccagaggatt ttttatgtc agtaaatcga     960
taaataatgc ctttaacct ttcctttatg ttgatcttcc cgaaactatg aaaactatta    1020
tatataacta ggggagaaga aacatgggc atagacgatg tgctgctgag agtcacaatg    1080
cggatcatca gggtctcccg tcacctggaa accaccagac cgtagactga atatccgagg   1140
gaaactgaat ataaatctgg cccgaataca aggaatcctg ttcgggatcc tcggtaagac   1200
gagcataaag cctctccggc tccggagccg atgtgggggg agatggggta aaagggggag   1260
cctggccaac aggacaaagc tgagcgtaaa ccgtccccgg cgatggaggg gtacacggct   1320
cggtaacagg acacaatgca gggaagatgc cctccggaga tggaggctgg ggagggcaga   1380
agagggaatg gggagtacag atgggaggtg gtggggtcga gcagagctgg gcgcaaagct   1440
cctccgcatc gggaggaggg ggggtacaga taggaggttg gaggggggaa ggccccggag   1500
cgtagataat atgggagta gagatgggag gtggtggggt cgagcagagc cccggagcgt   1560
agaaaatatg gggagtagag atgggaggtg gtggggtcga gcagagctgg gcgcaaagct   1620
cctccgcatc gggaggaggg ggggtacaga taggaggttg gaggggggaa ggccccggag   1680
cgtagataat atgggagta gagatgggag gtggggtcga gcagagctgg gcgcaaagtt   1740
cctccgtatc gggaggaggg ggggtacaga taggaggttg ggaaccggag caatgtggag   1800
cgttaggttc atccggtgag ggaggtggag gagtgcaaat gggaggttca ggaacgggat   1860
cgtgcgggt ggtaagcagt ccaagggtca ccgttagggg taccgccata gggcaaactg    1920
gctcatgaca agccaactgt acacgcaggg acgtgcactc agtccttaga tctcgaattt   1980
ccttacgtag gtgttcattg gccctctgca gctcttcaca tgcttcatgg agtttgtcta   2040
catagtccgt ctgctccctg cgtcttctcc gagaggcgtc acgattcctt tttctcctcc   2100
tttccagctt ctgtttctcc tcctcagata ggccgtcagg gaagggtgt ttggagggggc   2160
tgttggggat gtcgtgactt ttccttttt tccgtctcga agtcgacccg agagaaagat   2220
cgaggggga cggatcgtca gcgggactgt agggcatagc gcccggctct ggctcctgag   2280
acatctcttt acacctgtac cgtgcccgcc ttctccctgg tatacacctg caagagacgc   2340
ctgcctagga atcagtgtgc ggaatttatt cttaacattc cagcaccaac ctccccgaac   2400
caaataata attaaaaaag caacacccac agacccgaaa gtattgaaga attacacgtt   2460
cgcgaacggt cacaattcac ctgtcatttt ataaggagc aatagtttat ttaagaggta   2520
ggtataaatc gatcatttcc cccccccccc cccgtctccg tatcactccc gaaccattag   2580
atatcagtcg atccagcccc ccacgtcatg catgactatc gtctttatat caccgaatt   2639
```

<210> SEQ ID NO 22
<211> LENGTH: 2458
<212> TYPE: DNA
<213> ORGANISM: Artificial sequence
<220> FEATURE:
<223> OTHER INFORMATION: Synthetic

<400> SEQUENCE: 22

```
aattcaaact attcttgtaa tgtcgtacga gcctcgttcc gttcgctctt tcatgcgcag      60
```

```
cattaccggt gtaaatgtaa taatgccgca cagtgaacaa gcaaaagggg aagagagtct    120
ccggatagcc gttacaatcc agtaacgact taacgcagat tactcctgca taagcgtctc    180
tgcgatgagg tattttccat atgttcctgg aggtccgtgc ctgtatattc gttaatgtcg    240
acatctgcct atgtgcctgt gtatcggtgc ataggagtat gtctgtgcat ccctgtatat    300
attatctgtg catatttgca taattcataa acgaatattt aattacagta gtgttgcgcg    360
agccccgatc cattgatctg ctcacgactg tagcacttag aatcgcacag tgcacagcca    420
gtgagctggc cacaggagag ggacataggc ccgattgctg ggacccggat gagagatcaa    480
tcgtgttgtt ccttacgata acctaatcag caccaccgaa ttatacgaga ctgcattaac    540
tcacatctgc taaaggtttc gcttattcct tttacatccg aatgtccatc ctgttatctt    600
caatattcct taatgtgcga tgtccatatc ccttctaaaa aaaaaaacag ccaggcatag    660
tttttgagcc tggaaaactt accgcaggct tcatagaagc catatcccga ataatactcc    720 ataccccc cccccttcc ccaaccgttc tgtatagaac gagaatttgc catttaagca    780
gtctggggcc gagagatgtt gccccagaag ttttccacat agctaagttt atctcatact    840
tcggaactcc tggagccaac aaatcccctg accatgtaac tcaaaatagt tcttccgagt    900
ctaagctaca cggtaaggaa aatttgttac cccagaggat tttttttatgt cagtaaatcg    960 ataaataatg cctttaaccc tttcctttat gttgatcttc ccgaaactat gaaaactatt    1020
atatataact aggggagaag aaacatgggg catagacgat gtgctgctga gagtcacaat    1080
gcggatcatc agggtctccc gtcacctgga aaccaccaga ccgtagactg aatatccgag    1140
ggaaactgaa tataaatctg gcccgaatac aaggaatcct gttcgggatc ctcggtaaga    1200
cgagcataaa gcctctccgg ctccggagcc ggatgtgggg gagatggggt aaaaagggga    1260
gcctggccaa caggacaaag ctgagcgtaa accgtcccg gcgatggagg ggtacacggc    1320
tcggtaacag gacacaatgc agggaagatg ccctccggag atggaggctg ggagggcag    1380 aagagggaat ggggagtaca gatgggaggt ggtggggtcg agcagagctg ggcgcaaagc    1440
tcctccgcat cgggaggagg gggggtacag ataggaggtt ggagggggga aggccccgga    1500
gcgtagataa tatggggagt agagatggga ggtggggtcg agcagagctg ggcgcaaagt    1560
tcctccgtat cgggaggagg gggggtacag ataggaggtt gggaaccgga gcaatgtgga    1620
gcgttaggtt catccggtga gggaggtgga ggagtgcaaa tgggaggttc aggaacggga    1680
tcgtgcgggg tggtaagcag tccaagggtc accgttaggg gtaccgccat agggcaaact    1740
ggctcatgac aagccaactg tacacgcagg gacgtgcact cagtccttag atctcgaatt    1800
tccttacgta ggtgttcatt ggccctctgc agctcttcac atgcttcatg gagtttgtct    1860
acatagtccg tctgctccct gcgtcttctc cgagaggcgt cacgattcct tttctcctc    1920 ctttccagct tctgtttctc ctcctcagat aggccgtcag ggaagggtg tttggagggg    1980 ctgttgggga tgtcgtgact tttccttttt ttccgtctcg aagtcgaccc gagagaaaga    2040 tcgaggggggg acggatcgtc agcgggactg tagggcatag cgcccggctc tggctcctga    2100
gacatctctt tacacctgta ccgtgcccgc cttctccctg gtatacacct gcaagagacg    2160
cctgcctagg aatcagtgtg cggaatttat tcttaacatt ccagcaccaa cctcccccgaa    2220 ccaaaataat aattaaaaaa gcaacaccca cagacccgaa agtattgaag aattacacgt    2280
tcgcgaacgg tcacaattca cctgtcattt tataaaggag caatagttta tttaagaggt    2340
```

```
aggtataaat cgatcatttc cccccccccc ccgtctccgt atcactcccg aaccattaga    2400
tatcagtcga tccagccccc cacgtcatgc atgactatcg tctttatatc accgaatt     2458
```